(12) United States Patent
Wang et al.

(10) Patent No.: US 9,844,339 B2
(45) Date of Patent: *Dec. 19, 2017

(54) TEXTILE-BASED PRINTABLE ELECTRODES FOR ELECTROCHEMICAL SENSING

(71) Applicant: The Regents of the University of California, Oakland, CA (US)

(72) Inventors: Joseph Wang, San Diego, CA (US); Joshua Ray Windmiller, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,412

(22) Filed: Sep. 4, 2015

(65) Prior Publication Data

US 2016/0095547 A1    Apr. 7, 2016

Related U.S. Application Data

(63) Continuation of application No. 13/703,333, filed as application No. PCT/US2011/037068 on May 18, 2011, now Pat. No. 9,125,625.
(Continued)

(51) Int. Cl.
*A61B 5/145*    (2006.01)
*A61B 5/00*     (2006.01)
(Continued)

(52) U.S. Cl.
CPC .......... *A61B 5/6804* (2013.01); *A61B 5/0002* (2013.01); *A61B 5/021* (2013.01);
(Continued)

(58) Field of Classification Search
None
See application file for complete search history.

(56) References Cited

U.S. PATENT DOCUMENTS 4,969,468 A    11/1990   Byers et al.
5,035,711 A     7/1991   Aoki et al.
(Continued)

FOREIGN PATENT DOCUMENTS

CN    101068591 A    11/2007
EP       1187653     12/2000
(Continued)

OTHER PUBLICATIONS

Adar et al., Stochastic Computing with Biomolecular Automata, Proc. Natl. Acad. USA., 101(27):9960-9965, 2004.
(Continued)

*Primary Examiner* — J. Christopher Ball
(74) *Attorney, Agent, or Firm* — Perkins Coie LLP

(57) ABSTRACT

Techniques and systems are disclosed for implementing textile-based screen-printed amperometric or potentiometric sensors. The chemical sensor can include carbon based electrodes to detect at least one of NADH, hydrogen peroxide, potassium ferrocyanide, TNT or DNT, in liquid or vapor phase. In one application, underwater presence of chemicals such as heavy metals and explosives is detected using the textile-based sensors.

9 Claims, 29 Drawing Sheets

Related U.S. Application Data

(60) Provisional application No. 61/354,157, filed on Jun. 11, 2010, provisional application No. 61/353,581, filed on Jun. 10, 2010.

(51) Int. Cl.

| | | |
|---|---|---|
| *A61B 5/1477* | (2006.01) | |
| *A61B 5/0205* | (2006.01) | |
| *A61B 5/021* | (2006.01) | |
| *A61B 5/024* | (2006.01) | |
| *A61B 5/0245* | (2006.01) | |
| *C12Q 1/00* | (2006.01) | |
| *G01N 27/30* | (2006.01) | |
| *G01N 33/22* | (2006.01) | |
| *A61B 5/1486* | (2006.01) | |
| *A41D 1/00* | (2006.01) | |
| *G01N 27/327* | (2006.01) | |
| *G01N 33/00* | (2006.01) | |
| *H05K 1/03* | (2006.01) | |
| *H05K 3/12* | (2006.01) | |

(52) U.S. Cl.
CPC .......... *A61B 5/0205* (2013.01); *A61B 5/0245* (2013.01); *A61B 5/02444* (2013.01); *A61B 5/1477* (2013.01); *A61B 5/1486* (2013.01); *A61B 5/14517* (2013.01); *A61B 5/14532* (2013.01); *A61B 5/14546* (2013.01); *A61B 5/4266* (2013.01); *A61B 5/4845* (2013.01); *A61B 5/4884* (2013.01); *A61B 5/6802* (2013.01); *A61B 5/6807* (2013.01); *A61B 5/6808* (2013.01); *A61B 5/6831* (2013.01); *A61B 5/742* (2013.01); *C12Q 1/001* (2013.01); *G01N 27/308* (2013.01); *G01N 33/22* (2013.01); *A41D 1/002* (2013.01); *A61B 2560/0214* (2013.01); *G01N 27/3271* (2013.01); *G01N 33/0057* (2013.01); *H05K 1/038* (2013.01); *H05K 3/1216* (2013.01)

(56) References Cited

U.S. PATENT DOCUMENTS

| | | |
|---|---|---|
| 5,869,078 A | 2/1999 | Baudino |
| 6,132,755 A | 10/2000 | Eicher et al. |
| 6,465,091 B1 | 10/2002 | Ou-Yang |
| 6,527,762 B1 | 3/2003 | Santini, Jr. et al. |
| 6,587,705 B1 | 7/2003 | Kim et al. |
| 6,611,707 B1 | 8/2003 | Prausnitz et al. |
| 7,344,499 B1 | 3/2008 | Prausnitz et al. |
| 8,110,079 B2 | 2/2012 | Gooding et al. |
| 8,236,368 B2 | 8/2012 | Jung et al. |
| 8,257,324 B2 | 9/2012 | Prausnitz et al. |
| 8,815,070 B2 | 8/2014 | Wang et al. |
| 2002/0004640 A1 | 1/2002 | Conn et al. |
| 2002/0055704 A1 | 5/2002 | Scott et al. |
| 2002/0072784 A1 | 6/2002 | Sheppard, Jr. et al. |
| 2002/0105080 A1 | 8/2002 | Speakman |
| 2003/0104119 A1 | 6/2003 | Wilson et al. |
| 2003/0135158 A1 | 7/2003 | Gonnelli |
| 2003/0208167 A1 | 11/2003 | Prausnitz et al. |
| 2003/0235817 A1 | 12/2003 | Bartkowiak et al. |
| 2005/0036020 A1 | 2/2005 | Li et al. |
| 2005/0267440 A1 | 12/2005 | Herman et al. |
| 2006/0264716 A1 | 11/2006 | Zander |
| 2006/0281121 A1 | 12/2006 | Unger et al. |
| 2007/0078445 A1 | 4/2007 | Malloy |
| 2007/0170054 A2 | 7/2007 | Wilsey |
| 2008/0009800 A1 | 1/2008 | Nickel |
| 2008/0009801 A1 | 1/2008 | Nickel |
| 2008/0027369 A1 | 1/2008 | Carter et al. |
| 2008/0033269 A1 | 2/2008 | Zhang |
| 2008/0097280 A1 | 4/2008 | Martin et al. |
| 2008/0221408 A1 | 9/2008 | Hoarau et al. |
| 2008/0275327 A1 | 11/2008 | Faarbaek et al. |
| 2008/0311670 A1* | 12/2008 | Zhu .................... A61B 5/14514 436/95 |
| 2009/0084678 A1 | 4/2009 | Joshi et al. |
| 2009/0090623 A1 | 4/2009 | Chuang et al. |
| 2009/0101498 A1 | 4/2009 | Papadimitrakopoulos et al. |
| 2009/0191616 A1 | 7/2009 | Lu et al. |
| 2009/0218239 A1 | 9/2009 | Gooding et al. |
| 2009/0259118 A1 | 10/2009 | Feldman et al. |
| 2010/0021637 A1 | 1/2010 | Revol et al. |
| 2010/0137779 A1 | 6/2010 | Seitz |
| 2011/0105871 A1 | 5/2011 | Zimmermann et al. |
| 2011/0140703 A1 | 6/2011 | Chiao et al. |
| 2011/0230736 A1 | 9/2011 | Tepper et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0277629 A1 | 11/2012 | Bernstein et al. |
| 2013/0065257 A1 | 3/2013 | Wang et al. |
| 2013/0135158 A1 | 5/2013 | Faraone et al. |
| 2013/0158376 A1 | 6/2013 | Hayter et al. |
| 2013/0345597 A1 | 12/2013 | Hagino et al. |
| 2014/0135679 A1 | 5/2014 | Mann et al. |

FOREIGN PATENT DOCUMENTS

| | | |
|---|---|---|
| EP | 1372602 | 4/2007 |
| JP | H0231741 | 2/1990 |
| JP | H07275227 A | 10/1995 |
| JP | 2003038464 A | 2/2003 |
| JP | 2003038465 A | 2/2003 |
| JP | 2005087613 A | 4/2005 |
| JP | 2005510467 A | 4/2005 |
| JP | 2005525141 A | 8/2005 |
| JP | 2005322591 A | 11/2005 |
| JP | 2008512162 A | 4/2008 |
| JP | 2008540013 A | 11/2008 |
| WO | 2006060106 | 6/2006 |
| WO | WO-2006116242 A2 | 11/2006 |
| WO | WO-2007040938 A1 | 4/2007 |
| WO | 2010022252 | 2/2010 |
| WO | WO-2010014959 A2 | 2/2010 |
| WO | WO-2010045247 A1 | 4/2010 |
| WO | WO-2010120364 A2 | 10/2010 |
| WO | 2011156095 | 12/2011 |
| WO | 2012142625 | 10/2012 |

OTHER PUBLICATIONS

Adhikari, B. et al., "Polymers in sensor applications", Progress in Polymer Science, 2004, vol. 29, pp. 699-766.

Albareda-Sirvent, M. et al., "Configurations used in the design of screen-printed enzymatic biosensors. A review", Sensors and Actuators B: Chemical 2000, 69, pp. 153-163.

Almog, J. et al., "Recover and Detection of Urea Nitrate in Traces", J. Forensic Sci., 2007, vol. 52, No. 6, pp. 1284-1290.

Amir et al., Biofuel Cell Controlled by Enzyme Logic Systems, J. Am. Chem. Soc. 131:826-832, 2009.

Amos, A.F. et al., "The Rising Global Burden of Diabetes and its Complications: Estimates and Projections to the Year 2010", Diabetic Med., 1997, 14, pp. S7-S85.

Andreasson et al., A molecule-based 1:2 digital demultiplexer, J. Phys. Chem. C, 111:14274-14278, 2007.

Andréasson et al., All-Photonic Molecular Half-Adder, J. Am. Chem. Soc., 128:16259-16265, 2006.

Andréasson et al., Molecule-Based Photonically Switched Half-Adder, J. Am. Chem. Soc., 126:15926-15927, 2004.

Bakaltcheva, I. B. et al., "Multi-analyte explosive detection using a fiber optic biosensor", Anal. Chim. Acta 1999, 399, pp. 13-20.

Bakker, E. et al., "Electrochemical Sensors", Anal. Chem. 2002, 74, pp. 2781-2800.

(56) References Cited

OTHER PUBLICATIONS

Bandodkar, A. J. et al., "Epidermal tattoo potentiometric sodium sensors with wireless signal transduction for continuous non-invasive sweat monitoring", Biosens. Bioelectron. 2014, 54, pp. 603-609.
Bandodkar, A. J. et al., "Non-invasive wearable electrochemical sensors: a review", Trends Biotechnol. 2014, 32, pp. 363-371.
Bandodkar, A. J. et al., "Tattoo-Based Noninvasive Glucose Monitoring: A Proof-of-Concept Study", Anal. Chem. 2015, 87, 394-398.
Bandodkar, A. J. et al., "Tattoo-based potentiometric ion-selective sensors for epidermal pH monitoring", Analyst, 2013, 138, pp. 123-128.
Bardea et al., $NAD^+$-Dependent enzyme electrodes: Electrical contact of cofactor-dependent enzymes and electrodes, J. Am. Chem. Soc., 119:9114-9119, 1997.
Baron et al., An electrochemical/photochemical information processing system using a monolayer-functionalized electrode, Chem. Commun., 2147-2149, 2006.
Baron et al., Elementary Arithmetic Operations by Enzymes: A Model for Metabolic Pathway Based Computing, Agnew. Chem. Int. Ed., 45:1572-1576, 2006.
Baron et al., Logic Gates and Elementary Computing by Enzymes, J Phys. Chem. A., 110(27):8548-8553, 2006.
Baron et al., Two coupled enzymes perform in parallel the "AND" and "InhibAND" logic gates operations, Org. Biomol. Chem., 4:989-991, 2006.
Baytekin et al., A Molecular NAND Gate Based on Watson-Crick Base Pairing, Org. Lett., 2(12):1725-1727, 2000.
Berzowska, J., "Electronic Textiles: Wearable Computers, Reactive Fashion, and Soft Computation", Textile, 2005, vol. 3, Issue 1, pp. 2-19.
Bit, (2008) In Philip's Encyclopedia 2008. Retrieved from http://www.credoreference.com/entry/philipency/bit.
Brown et al., Molecules That Add Up, Chem. Commun., 2461-2463, 2002.
Cagan, A. et al., "Reliable, rapid and simple voltammetric detection of urea nitrate explosive", Analyst 2008, 133, pp. 585-587.
Cai, J. et al., "Flexible thick-film electrochemical sensors: Impace of mechanical bending and stress on the electrochemical behavior", Sensors and Actuators B: Chemical, vol. 137, Issue 1, 2009, pp. 379-385.
Capua, E. et al., "Detection of triacetone triperoxide (TATP) with an array of sensors based on non-specific interactions", Sensors and Actuators B 140 (2009) pp. 122-127.
Charles, P. T. et al., "On-Site Immunoanalysis of Nitrate and Nitroaromatic Compounds in Groundwater", Environ. Sci. Technol. 2000, 34, pp. 4641-4650.
Cheng, H. et al., "An analytical model of strain isolation for stretchable and flexible electronics", Appl. Phys. Lett. 98, 061902 (2011), 4 pages.
Ching, C. T. S. et al., "A Mediated Glucose Biosensor Incorporated with Reverse Iontophoresis Function for Noninvasive Glucose Monitoring", Annals Biomed. Eng. 2010, vol. 38, No. 4, pp. 1548-1555.
Choleau, C. et al., "Calibration of a subcutaneous amperometric glucose sensor implanted for 7 days in diabetic patients Part 2. Superiority of the one-point calibration method", Biosens. Bioelectron. 2002, 17, pp. 647-654.
Chuang, M. C. et al. Textile-based electrochemical sensing: effect of fabric substrate and detection of nitroaromatic explosives. Electroanal. 22, 2511-2518 (2010).
Chuang, M.C. et al., "Flexible thick-film glucose bionsensor: Influence of mechanical bending on the performance", Talanta, 2010, 81, pp. 15-19.
Coyle, S. et al., "Smart nanotextiles: A review of materials and applications", MRS Bull. 32, May 2007, pp. 434-442.
Credi et al., Logic Operations at the Molecular Level. An XOR Gate Based on a Molecular Machine, J. Am. Chem. Soc., 119:2679-2681, 1997.
Credi et al., Molecules That Make Decisions, Angew. Chem. Int. Ed., 46:5472-5475, 2007.
De Silva et al., 'Off-On' Fluorescent Sensors for Physiological Levels of Magnesium Ions Based on Photoinduced Electron Transfer (PET), Which Also Behave as Photoionic OR Logic Gates, J. Chem. Soc., Chem. Commun., 1213-1214, 1994.
De Silva et al., A Molecular Photoionic AND Gate Based on Fluorescent Signalling, Nature 364: 42-44, 1993.
De Silva et al., A Supramolecular Chemistry Basis for Molecular Logic and Computation, Coord. Chem. Rev., 251:1623-1632, 2007.
De Silva et al., Integration of Logic Functions and Sequential Operation of Gates at the Molecular-Scale, J Am. Chem. Soc., 121:1393-1394, 1999.
De Silva et al., Molecular Logic and Computing, Nature Nanotechnology, 2:399-410, 2007.
De Silva et al., Molecular Photoionic AND Logic Gates with Bright Fluorescence and "Off-On" Digital Action, J. Am. Chem. Soc., 119:7891-7892, 1997.
De Silva et al., Simultaneously Multiply-Configurable or Superposed Molecular Logic Systems Composed of ICT (Internal Charge Transfer) Chromophores and Fluorophores Integrated with One- or Two-Ion Receptors, Chem. Eur. J., 8:4935-4945, 2002.
De Sousa et al., A Molecular Tool Kit for the Variable Design of Logic Operations (NOR, INH, EnNOR), Chem. Commun., 2051-2053, 2006.
Dempsey et al., Electropolymerised o-Phenylenediamine Film as Means of Immobilising Lactate Oxidase for a L-Lactate Biosensor, Talanta, 40(3):445-451, 1993.
Diamond, D. et al., "Wireless sensor networks and chemo-/biosensing", Chem. Rev. 108, 2008, pp. 652-679.
Dungchai, W. et al., "Electrochemical Detection for Paper-Based Microfluidics", Anal. Chem. 2009, 81, pp. 5821-5826.
Ezziane, DNA Computing: Applications and Challenges, Nanotechnology, 17:R27-R39, 2006.
Fedichkin et al., Error Correction and Digitalization Concepts in Biochemical Computing, J. Comput. Theor. Nanosci., 5:36-43, 2008.
Gawalt, E. et al., "Self-Assembly and Bonding of Alkanephosphonic Acids on the Native Oxide Surface of Titanium", Langmuir 2001, 17, pp. 5736-5738.
Ghajar, Traumatic brain injury, Lancet, 356:923-929, 2000.
Gross, T. M. et al., "Performance Evaluation of the MiniMed Continuous Glucose Monitoring System During Patient Home Use", Diabetes Technol. Therapeutics, 2000, 2, pp. 49-56.
Gun et al., Field-effect nanoparticle-based glucose sensor on a chip: Amplification effect of co-immobilized redox species, Electroanalysis 20, 16:1748-1753, 2008.
Gunnlaugsson et al., Lanthanide Macrocyclic Quinolyl Conjugates as Luminescent Molecular-Level Devices, J. Am. Chem. Soc., 123:12866-12876, 2001.
Gunnlaugsson et al., Luminescent Molecular Logic Gates: The Two-Input Inhibit (INH) Function, Chem. Commun., 93-94, 2000.
Gutowski, T. G. et al., "The elastic deformation of lubricated carbon fiber bundles: Comparison of theory and experiments", J. Compos. Mater. vol. 26, No. 16, 1992, pp. 2330-2347.
Hart, J.P. et al., "Screen-Printed Voltammetric and Amperometric Electrochemical Sensors for Decentralized Testing", Electroanalysis 1994, 6, pp. 617-624.
Head, Biomolecular realizations of a parallel architecture for solving combinatorial problems, New Generation Computing, 19:301-312, 2001.
Heller, Integrated Medical Feedback Systems for Drug Delivery, AIChE Journal, 51:1054-1061, 2005.
Jia, W. et al., "Electrochemical Tattoo Biosensors for Real-Time Noninvasive Lactate Monitoring in Human Perspiration", Anal. Chem. 2013, 85, pp. 6553-6560.
Kagie et al., Flexible Rolled Thick-Film Miniaturized Flow-cell for Minimally Invasive Amperometric Sensing, Electroanalysis, 20:1610-1615, 2008.
Karaguzel, B. et al., "Flexible, durable printed electrical circuits", J. Textile Inst. 2009, 100, 1, pp. 1-9.

(56) References Cited

OTHER PUBLICATIONS

Karyakin, A. A., "Prussian Blue and Its Analogues: Electrochemistry and Analytical Applicants", Electroanal. 2001, 13, No. 10, pp. 813-819.

Katakis et al., Catalytic electrooxidation of NADH for dehydrogenase emperometric biosensors, Mikrochim. Acta, 126:11-32, 1997.

Katz et al., A quinone-functionalized electrode in conjunction with hydrophobic magnetic nanoparticles acts as a "Write-Read-Erase" information storage system, Chem. Commun., 5641-5643, 2005.

Katz et al., Biofuel Cells Controlled by Logically Processed Biochemical Signals: Towards Physiologically Regulated Bioelectronic Devices, Chem. Eur. J., 15:12554-12564, 2009.

Katz et al., Biomolecule-functionalized carbon nanotubes: Applications in nanobioelectronics, ChemPhysChem, 5:1194-1104, 2004.

Katz et al., Electroanalytical and bioelectroanalytical systems based on metal and semiconductive nanoparticles, Electroanalysis, 16:19-44, 2004.

Katz et al., Electrocatalytic oxidation of reduced nicotinamide coenzymes at gold and platinum electrode surfaces modified with a monolayer of pyrroloquinoline quinone. Effect of $Ca^{2+}$ cations. J. Electroanal., Chem., 373, 189-200, 1994.

Katz et al., Enzyme-Based Logic Systems for Information Processing, Chem. Soc. Rev., 39:1835-1857, 2010.

Katz et al., Glucose oxidase electrodes via reconstitution of the apo-enzyme: Tailoring of novel glucose biosensors, Anal. Chim. Acta, 385:45-58, 1999.

Katz et al., Integrated nanoparticle-biomolecule hybrid systems: Synthesis, properties and applications, Angew. Chem. Int. Ed., 43:6042-6108, 2004.

Katz et al., Biosensing Strategies Based on Biochemical Logic Systems, The Fourth ICQNM, 2010, 15 pages.

Katz, Electronic biosensors based on biomaterial-nanoparticle hybrid systems, Smart Sensors and MEMS, NATO Science Series, 181(14):447-474, 2005.

Katz, et al., "Towards Biosensing Strategies Based on Biochemical Logic Systems", IEEE, 2010, 9 pages.

Kim, D. H.et al., "Epidermal Electronics", Science 333, 2011, pp. 838-843.

Kim, Jin Ho, Authorized Officer, Korean International Property Office, International Search Report, PCT Application No. PCT/US2013/040671, dated Mar. 7, 2014, 11 pages.

Kline et al., Activation of pyruvate dehydrogenase improves heart function and metabolism after hemorrhagic shock, J Mol Cell Cardio,I 29, 2465-2474 (1997).

Konry et al., Intelligent Medical Diagnostics via Molecular Logic, J. Am. Chem. Soc., 131:13232-13233, 2009.

Krämer et al., Coupling of Biocomputing Systems with Electronic Chips: Electronic Interface for Transduction of Biochemical Information, J. Phys. Chem. C, 113:2573-2579, 2009.

Kuznetz et al., A Novel All Optical Molecular Scale Full Adder, Chem. Phys. Lett., 451:63-67, 2008.

Lavan et al., Small-Scale Systems for In Vivo Drug Delivery, Nature Biotechnolog., 21(10):1184-1191, 2003.

Lawrence et al., Biocatalytic Carbon Paste Sensors Based on a Mediator Pasting Liquid, Anal. Chem., 76:3735-3739, 2004.

Lawrence et al., Chemical Adsorption of Phenothiazine Dyes onto Carbon Nanotubes: Toward the Low Potential Detection of NADH, Electrochemistry Communications, 8:71-76, 2006.

Li et al., Inhibit Logic Gate Based on Spiropyran Sensitized Semiconductor Electrode, Colloids Surf. A, 304:49-53, 2007.

Lin et al.,Carbon nanotubes (CNTs) for the development of electrochemical biosensors, Frontiers in Bioscience, 10:492-505, 2005.

Lindner, E. et al., "Microfabricated Potentiometric Electrodes and Their In Vivo Applications", Anal. Chem. 2000, 72, pp. 336-345.

Liu et al., Enzyme Nanoparticles-Based Electronic Biosensor, Chemical Comm., 27:3481-3483, 2005.

Liu et al., Versatile Apoferritin Nanoparticle Labels for Assay of Protein, Anal. Chem., 78:7417-7423, 2006.

Loaiza et al., Adaptive Orientation of Multifunctional Nanowires for Magnetic Control of Bioelectrocatalytic Processes, Angew. Chem. Int. Ed., 46:1508-1511, 2007.

Lopez et al., A Metallo-Supramolecular Approach to a Half-Subtractor, New J. Chem., 32:1473-1477, 2008.

Lu, D. et al., "Highly sensitive electrochemical detection of trace liquid peroxide explosives at a Prussian-blue 'artificial-peroxidase' modified electrode", Analyst 2006, 131, pp. 1279-1281.

Luxami et al., Molecular Half-Subtractor Based on 3,3'-bis(1H-benzimidazolyl-2-yl)[1,1']-binaphthalenyl-2,2'-diol, New J. Chem., 32:2074-2079, 2008.

Ma, R. et al., A stretchable electrode array for non-invasive, skin-mounted measurement of electrocardiography (ECG), electromyography (EMG) and electroencephalography (EEG), 2nd Annual International Conference of the IEEE EMBS, 2010, pp. 6405-6408.

MacDonald, W.A., "Engineered films for display technologies", J. Mater. Chemistry, 2004, 14, pp. 4-10.

Magri et al., From complexation to computation: Recent progress in molecular logic, Inorg. Chim. Acta., 360:751-764, 2007.

Malzahn, K.. et al., "Wearable electrochemical sensors for in situ analysis in marine environments" Analyst 136, 2011, pp. 2912-2917.

Manesh, K. M., et al., "Enzyme logic gates for the digital analysis of physiological level upon injury," Biosensors and Bioelectronics, vol. 24, 2009, p. 3569-3574.

Margulies et al., A Molecular Full-Adder and Full-Subtractor, an Additional Step Toward a Moleculator, J. Am. Chem. Soc., 128:4865-4871, 2006.

Margulies et al., A molecular keypad lock: A photochemical device capable of authorizing password entries, J. Am. Chem. Soc., 129:347-354, 2007.

Margulies et al., Digital Analysis of Protein Properties by an Ensemble of DNA Quadruplexes, J. Am. Chem. Soc., 131:9142-9143, 2009.

Martinez, A.W. et al., "Diagnositcs for the Developing World: Microfluidic Paper-Based Analytical Devices", Anal. Chem. 2010, 82, pp. 3-10.

Matsuyama, H. et al., "Analysis of solute diffusion in poly(vinyl alcohol) hydrogel membrane",.J. Membrane Sci. 126, 1997, pp. 151-160.

May et al., Towards De Novo Design of Deoxyribozyme Biosensors for GMO Detection, IEEE Sensors Journal, 8(6):1011-1019, 2008.

McCormick, C. et al., "Towards blood free measurement of glucose and potassium in humans using reverse iontophoresis", Sensors and Actuators B 166-167, 2012, pp. 593-600.

McGarraugh, G., "The Chemistry of Commercial Continuous Glucose Monitors", Diabetes Technol. Therapeutics 2009, 11, S17-S24.

Melnikov et al., Analog Noise Reduction in Enzymatic Logic Gates, J. Phys. Chem. B, 113:10472-10479, 2009.

Merritt, C.R. et al., "Textile-Based Capacitive Sensors for Respiration Monitoring", IEEE Sensors Journal 2009,9, pp. 71-78.

Motornov et al., "Chemical Transformers" from Nanoparticle Ensembles Operated with Logic, Nano Lett, 8(9):2993-2997, 2008.

Motornov et al., An Integrated Multifunctional Nanosystem from Command Nanoparticles and Enzymes, Small, 5(7):817-820, 2009.

Motornov et al., Chemical gating with nanostructured responsive polymer brushes: mixed brush versus homopolymer brush, ACS Nano, 2:41-52, 2008.

Mukherjee et al., Write-once-read-many-times (WORM) memory applications in a monolayer of donor/acceptor supramolecule, Chem. Mater., 19:1382-1387, 2007.

Musameh et al., Low potential stable NADH detection at carbon nanotube modified glassy carbon electrodes, Electrochem. Comm., 4:743-748, 2002.

Najmabadi et al., Systems Perspective to Digital Structures in Molecular Analysis, Org. Biomol. Chem., 5:214-222, 2007.

Newman, J. D. et al., "Home blood glucose biosensors: a commercial perspective", Biosensors and Bioelectronics, 20, 2005, pp. 2435-2453.

Niazov et al., Concatenated Logic Gates Using Four Coupled Biocatalysts Operating in Series, Proc. Natl. Acad. USA, 103:17160-17163, 2006.

(56) References Cited

OTHER PUBLICATIONS

Nie, Z. et al., "Electrochemical sensing in paper-based microfluidic devices", Lab on a Chip, 2010, 10, pp. 477-483.

Oliver, N. S. et al., "Glucose sensors: a review of current and emerging technology", Diabetic Medicine, 2009, 26, pp. 197-210.

Pandian, P.S. et al., "Smart Vest: Wearable multi-parameter remote physiological monitoring system", Medical Engineering & Physics, 30, 2008, pp. 466-477.

Pedrosa et al., "Nanofingers" based on Binary Gold-Polypyrrole Nanowires, Small, 4:738-741, 2008.

Pischel et al., Molecular logic devices (half-subtractor, comparator, complementary output circuit) by controlling photoinduced charge transfer processes, New J. Chem., 32:395-400, 2008.

Pischel, Chemical Approaches to Molecular Logic Elements for Addition and Subtraction, Chem. Int. Ed., 46:4026-4040, 2007.

Pita et al., Optoelectronic Properties of Nanostructured Ensembles Controlled by Biomolecular Logic Systems, ACS Nano, 2(10):2160-2166, 2008.

Pita et al., Enzyme logic gates for assessing physiological conditions during an injury: Towards digital sensors and actuators, Sensors and Actuators B: Chemical, 139 (2009) 631-636.

Pita et al., Enzyme-Based Logic Systems and Their Applications for Novel Multi-Signal-Responsive Materials, J. Mater. Sci.: Mater. Med., 20:457-462, 2009.

Pita et al., Multiple Logic Gates Based on Electrically Wired Surface-Reconstituted Enzymes, J. Am. Chem. Soc., 2008, 130, 36-37.

Pita et al., Set-Reset Flip-Flop Memory Based on Enzyme Reactions: Toward Memory Systems Controlled by Biochemical Pathways, J. Phys. Chem. B, 113:16071-16076, 2009.

Prasad, Regional Levels of Lactate and Norepinephrine After Experimental Brain Injury, Journal of Neurochemistry, 63(3), 1994.

Privman et al., Enzymatic AND-gate based on electrode-immobilized glucose-6-phosphate dehydrogenase: Towards digital biosensors and biochemical logic systems with low noise, Biosens. Bioelectron., 25:695-701, 2009.

Privman et al., Network Analysis of Biochemical Logic for Noise Reduction and Stability: A System of Three Coupled Enzymatic AND Gates, J. Phys. Chem. B, 113:5301-5310, 2009.

Privman et al., Optimization of Enzymatic Biochemical Logic for Noise Reduction and Scalability: How Many Biocomputing Gates Can Be Interconnected in a Circuit?, J. Phys. Chem. B, 112:11777-11784, 2008.

Privman, M., et al., "Switchable electrode controlled by enzyme logic network system: Approaching physiologically regulated bioelectronics," J. Am. Chem. Soc., vol. 131, No. 3, 2009, p. 1314-1321.

Qian et al., Multiple Molecular Logic Functions and Molecular Calculations Facilitated by Surfactant's Versatility, Chem. Commun., 2008, pp. 4141-4143.

Qu et al., A Half Adder Based on a Photochemically Driven [2]Rotaxane, Angew, Chem. Int. Ed., 44, 2005, pp. 5296-5299.

Raitman et al., Electrical contacting of glucose dehydrogenase by the reconstitution of a pyrroloquinoline quinone-functionalized polyaniline film associated with an Au-electrode: An in situ SPR-electrochemical study, Chem. Commun., 2002, pp. 1936-1937.

Rebrin, K. et al., "Can Interstitial Glucose Assessment Replace Blood Glucose Measurements", Diabetes Technology & Therapeutics, vol. 2, No. 3, 2000, pp. 461-472.

Ro K. S. et al., "Solubility of 2,4,6-Trinitrotoluene (TNT) in Water", J. Chem. Eng. Data, 1996, 41, pp. 758-761.

Rogers, J.A. et al., "A curvy, stretchy future for electronics", PNAS, Jul. 7, 2009, vol. 106, No. 27, pp. 10875-10876.

Romolo, F. S. et al., "Identification of gunshot residue: A critical review", Forensic Sci. Int.119, 2001, pp. 195-211.

Rosenberg et al., Studies on Hemorrhagic and Endotoxin Shock in Relation to Vasomotor Changes and Endogenous Circulating Epinephrine, Norepinephrine and Serotonin, Ann. Surgery, 154:611-627, 1961.

Scheller et al., Coupling of Immunoassays with Enzymatic Recycling Electrodes, Anal. Lett., 34(8) 2001, pp. 1233-1245.

Sivan et al., A Biochemical Logic Gate Using an Enzyme and its Inhibitor, Biosystems, 70:21-33, 2003.

Stojanovic et al., Computing with Nucleic Acids, Bioelectronics: From Theory to Applications, Willner I, Katz E, pp. 427-455, Wiley-VCH Weinheim, 2005.

Stout, P. J. et al., "A Novel Approach to Mitigating the Physiological Lag Between Blood and Interstitial Fluid Glucose Measurements", Diabetes Technology & Therapeutics, vol. 6, No. 5, 2004, pp. 635-644.

Strack et al., Biocomputing Security System: Concatenated Enzyme-Based Logic Gates Operating as a Biomolecular Keypad Lock, J. Am. Chem. Soc., 130:4234-4235, 2008.

Strack et al., Boolean Logic Gates that Use Enzymes as Input Signals, ChemBioChem 9:1260-1266, 2008.

Straight et al. All-Photonic Molecular XOR and NOR Logic Gates Based on Photochemical Control of Fluorescence in a Fulgimide-Porphyrin-Dithienylethene Triad, Adv. Funct. Mater., 17:777-785, 2007.

Sun, T.P.et al. "Carbon nanotube composites for glucose biosensor incorporated with reverse iontophoresis function for noninvasive glucose monitoring", Inter. J. Nanomed. 2010, 20, pp. 343-349.

Sylvia, J. M. et al., "Surface-Enhanced Raman Detection of 2,4-Dinitrotoluene Impurity Vapor as a Marker to Locate Landmines", Anal. Chem. 2000, 72, pp. 5834-5840.

Szacilowski et al., Digital Information Processing in Molecular Systems, Chem. Rev., 108:3481-3548, 2008.

Szacilowski, Biomedical Implications of Information Processing in Chemical Systems: Non-Classical Approach to Photochemistry of Coordination Compounds, Biosystems, 90:738-749, 2007.

Tam et al., Biofuel Cell Controlled by Enzyme Logic Network—Approaching Physiologically Regulated Devices, Bioelectrochemistry, 76:4-9, 2009.

Tam et al., Enzymelogic Network Analyzing Combinations of Biochemical Inputs and Producing Fluorescent Output Signals, Sens. Actuat. B, 140:1-4, 2009.

Tanenberg, R. et al., "Use of the Continuous Glucose Monitoring System to Guide Thereapy in Patients with Insulin-Treated Diabetes: A Randomized Controlled Trial", Mayo Clin. Proc. 2004, 79, pp. 1521-1526.

Tang, S.L., "Recent developments in flexible wearable electronics for monitoring applications", Transd. Institute Measurement and Control, 2007, 29, pp. 283-300.

Tangkuaram et al., Highly Stable Amplified Low-Potential Electrocatlytic Detection of $NAD^+$ at Azure-Chitosan Modified Carbon Electrodes, Sensors and Actuators B., 121:277-281, 2007.

Tibbetts, G. C. et al., .Mechanical properties of vapor-grown carbon fiber composites with thermoplastic matrices, J. Mater. Res. 14, 1999, pp. 2871-2880.

Tierney, M. J. et al., "Electroanalysis of Glucose in Transcutaneously Extrated Samples", Electroanal. 2000, 12, pp. 666-671.

Tokarev et al., An electrochemical gate based on a stimuli-responsive membrane associated with an electrode surface, J. Phys. Chem. B, 111:12141-12145, 2007.

Tokarev et al., Stimuli-Responsive Hydrogel Membranes Coupled with Biocatalytic Processes, ACS Appl. Mater. Interfaces, 1(3):532-536, 2009.

Tomizaki et al., Phosphate-Mediated Molecular Memory Driven by Two Different Protein Kinases as Information Input Elements, J. Am. Chem. Soc., 129:8345-8352, 2007.

Turfan et al., Modulation of Boradiazaindacene Emission by Cation-Mediated Oxidative PET, Org. Lett., 4(17):2857-2859, 2002.

Unger et al., Towards Computing with Proteins, Proteins, 63:53-64, 2006.

Urbanski, T., "Chemistry and technology of explosives", v 4. Oxford, New York, Pergamon Press, 1964-1985.

Vashist, S. K.., "Non-invasive glucose monitoring technology in diabetes management: A review", Anal. Chim. Acta 2012, 750, pp. 16-27.

Vasilyev et al., Logic Gates Based on Magnetic Nanoparticles Functionalized with a Bioelectrocatalytic System, Electroanalysis, 20(1):22-29, 2008.

(56) References Cited

OTHER PUBLICATIONS

Von Maltzahn et al., Nanoparticle Self-Assembly Gated by Logical Proteolytic Triggers, J. Am. Chem. Soc., 129:6064-6065, 2007.
Wagner et al., Systems Chemistry: Logic Gates, Arithmetic Units, and Network Motifs in Small Networks, Chem. Eur. J., 15:1765-1775, 2009.
Walia et al., The relationship between blood glucose, mean arterial pressure and outcome after severe head injury: an observational study, Injury Int. J. Care Injured, 33:339-344, 2002.
Wang et al., 9-(Cycloheptatrienylidene)-fluorene Derivative: Remarkable Ratiometric pH Sensor and Computing Switch with NOR Logic Gate, Org. Lett., 7(17):3669-3672, 2005.
Wang et al., Biocatalytically Induced Formation of Cupric Ferrocyanide Nanoparticles and Their Application for Electrochemical and Optical Biosensing of Glucose, Small, 2(1):129-134, 2006.
Wang et al., Biomaterial-nanoparticle hybrid systems for sensing and electronic devices. In: *Bioelectronics: From Theory to Applications,* I. Willner, E. Katz (Eds.), Wiley-VCH, Weinheim, Germany, Chapter 8, pp. 231-264, 2005.
Wang et al., Catheter Microelectrode Assembly for In-Vivo and In-Vitro Voltammetric Analysis of Body Fluids, Talanta, 30(2):121-123, 1983.
Wang et al., Enzyme-dispersed carbon nanotube electrodes: A needle electrode for monitoring glucose, Analyst, 128:1382-1385, 2003.
Wang et al., Highly stable voltammetric detection of nitroaromatic explosives in the presence of organic surfactants at a polyphenol-coated carbon electrode, Electroanalysis, 16(15):1232-1235, 2004.
Wang et al., Needle-Type Dual Microsensor for the Simultaneous Monitoring of Glucose and Insulin, Anal. Chem., 73:844-848, 2001.
Wang et al., One-step Electropolymeric Coimmobilization of Glucose Oxidase and Heparin for Amperometric Biosensing of Glucose, Analyst, 125:1431-1434, 2000.
Wang et al., Overoxidized Poly {pyrrole-co[3-(pyrrol-1-yl)propanesulfunate]} coated Platinum Electrodes for Selective Detection of Catecholamine Neurotransmitters, Analyst, 122:981-984, 1997.
Wang et al., Permselective Lipid/PPD Coatings for Amperometric Biosensing of Glucose, Anal. Chim. Acta., 283:683-687, 1993.
Wang et al., "Thermal Stabilization of Enzymes Immobilized within Carbon Paste Electrodes", Anal. Chem., 69:3124-3127, 1997.
Wang et al., Remarkably Selective Metalized Carbon Amperometric Biosensors, Anal. Chim. Acta., 305:3-7, 1995.
Wang et al., Sol-gel-derived thick-film amperometric immunosensors, Anal. Chem., 70:1171-1175, 1998.
Wang et al., Switchable Electrode Controlled by Boolean Logic Gates Using Enzymes as Input Signals, Bioelectrochemistry, 77:69-73, 2009.
Wang, Carbon-Nanotube based electrochemical biosensors: A Review, Electroanalysis, 17(1):7-16, 2005.
Wang, Electrochemical Biosensors: Towards Point-of-Care Cancer Diagnostics, Biosensors & Bioelectronics, 21:1887-1892, 2006.
Wang, Electrochemical Glucose Biosensors, Chem. Rev., 108:814-825, 2008.
Wang, In Vivo Glucose Monitoring: Towards 'Sense and Act' Feedback-Loop Individualized Medical Systems, Talanta, 75:636-641, 2008.
Wang, J. et al., "Bismuth-coated carbon electrodes for anodic stripping voltammetry" Anal.Chem. 72, 2000, pp. 3218-3222.

Wang, J. et al., "Miniaturized glucose sensors based on electrochemical codeposition of rhodium and glucose oxidase onto carbon-fiber electrodes", Anal.Chem. 64, 1992, pp. 456-459.
Wang, J., "Portable electrochemical systems", Trends in Anal. Chem. 2002, vol. 21, No. 4, pp. 226-232.
Wang, Oxygen-Rich Oxidase Enzyme Electrodes for Operation in Oxygent-Free Solutions, J. Am. Chem. Soc., 1998, 120, pp. 1048-1050.
Wang, Nanomaterial-Based Amplified Transduction of Biomolecular Interactions, Small, 1:1036-1043, 2005.
Waugh Jr., W. L. et al., "Terrorism as Disaster", Handbooks of Disaster Research, Springer, 2007, pp. 388-404.
Whiting, D. R. et al., "IDF Diabetes Atlas: Global estimates of theprevalence of diabetes for 2011 and 2030", Diabetes Res. Clin. Pract. 2011, 94, pp. 311-321.
Win et al., Higher-Order Cellular Information Processing with Synthetic RNA Devices, Science, 322:456-460, 2008.
Windmiller, J. R., et al., "Electrochemical sensing b ased on printable temporary transfer tattoos", Chem. Commun. 2012, 48, pp. 6794-6796.
Windmiller, J. R., et al., "Wearable Electrochemical Sensors and Biosensors: A Review", Electroanal. 2013, 25, No. 1, pp. 29-46.
Windmiller, J.R. et al., "Bioelectronic system for the control and readout of enzyme logic gates", Sensor. Actuat. B 155, 2011, pp. 206-213.
Xiao et al., 'Plugging into enzymes': Nanowiring of redox-enzymes by a gold nanoparticle, Science, 1877-1881, 2003.
Xu et al., Polymer actuator valves toward controlled drug delivery application, Biosensors Bioelectronics, 21:2094-2099, 2006.
Yang, Y. L. et al., "Thick-film textile-based amperometric sensors and biosensors" Analyst 135, 2010, pp. 1230-1234.
Zhang, H.-X. et al., "Electrochemical Sensor for Detecting Ultratrace Nitroaromatic Compounds Using Mesoporous Si02-Modified Electrode", Analytical Chemistry, Mar. 15, 2006, vol. 78, No. 6, pp. 1967-1971.
Zhou, J., et al., "Bioelectrocatalytic system coupled with enzyme-based biocomputing ensembles performing boolean logic operations: Approaching "Smart" physiologically controlled biointerfaces," ACS Applied Materials & Interfaces, vol. 1, No. 1, 2009, p. 144-149.
Zhou, J., et al., "Enzyme-based NAND and NOR logic gates with modular design," J. Phys. Chem. B,. vol. 113, 2009, p. 16065-16070.
Zink et al., Effects of Ethanol on Brain Lactate in Experimental Traumatic Brain Injury with Hemorrhagic Shock, Brain Res., 837:1-7, 1999.
Zong et al., L-Arginine Bearing an Anthrylmethyl Group: Fluorescent Molecular NAND Logic Gate With H+ and ATP as Inputs, Tetrahedron Lett., 48:3891-3894, 2007.
Gittard, et al., "Fabrication of Polymer Microneedles Using a Two-Photon Polymerization and Micromolding Process", J. Diabetes Sci. Technol., 2009, 3, pp. 304-311.
Jeon, et al., "Electrically Actuatable Smart Nanoporous Membrane for Pulsatile Drug Release", Nano Lett., 2011, 11, pp. 1284-1288.
Windmiller, et al., "Microneedle array-based carbon paste amperometric sensors and biosensors", Analyst, 2011, pp. 1846-1851.
Wang, et al., "Remote electrochemical sensor for monitoring TNT in natural waters", Anal. Chim. Acta 361, (1998) pp. 85-91.
International Search Report and Written Opinion for PCT Application No. PCT/US2011/037068; dated Dec. 21, 2011; 13 pages.

\* cited by examiner

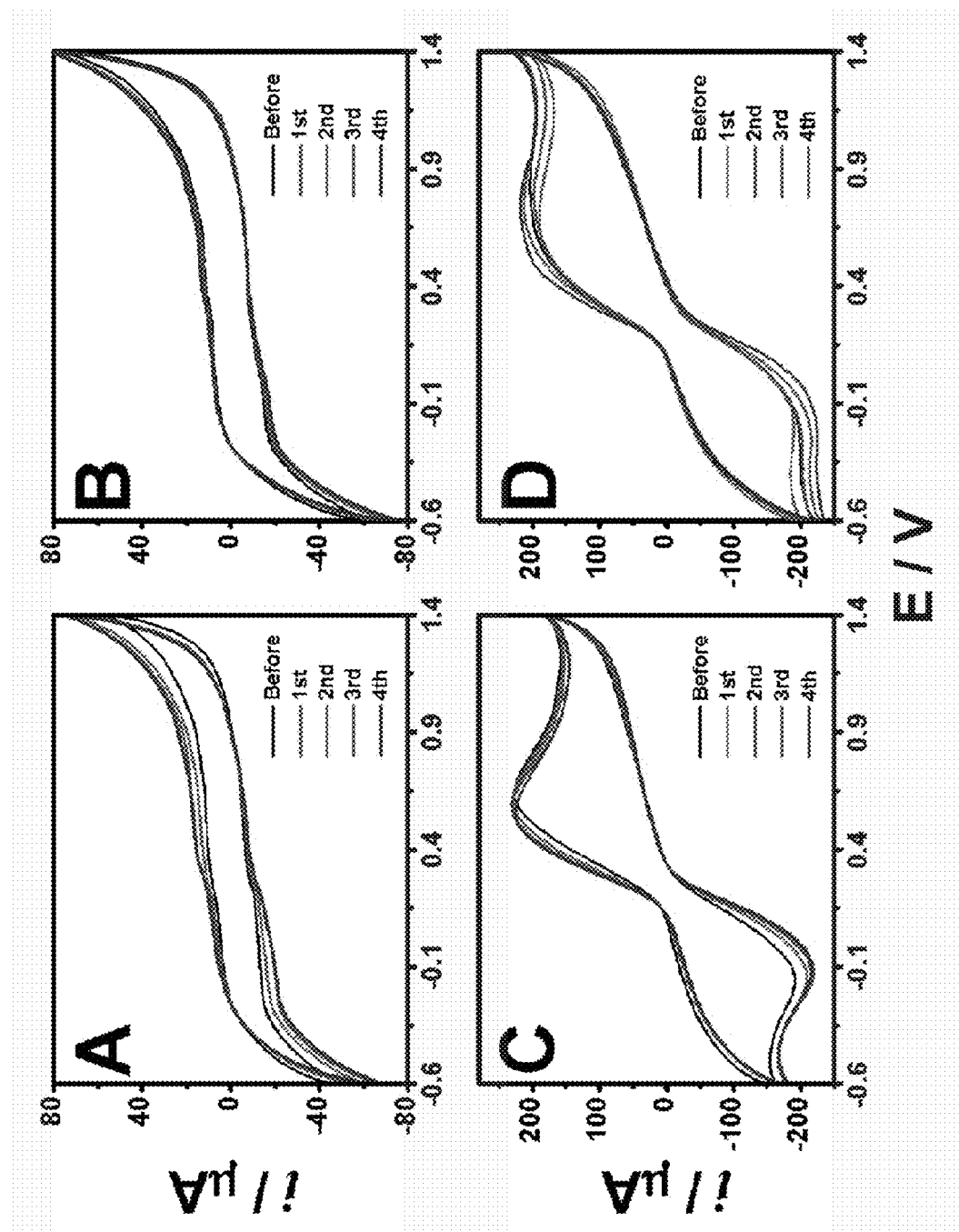
FIGS. 3A, 3B, 3C, and 3D

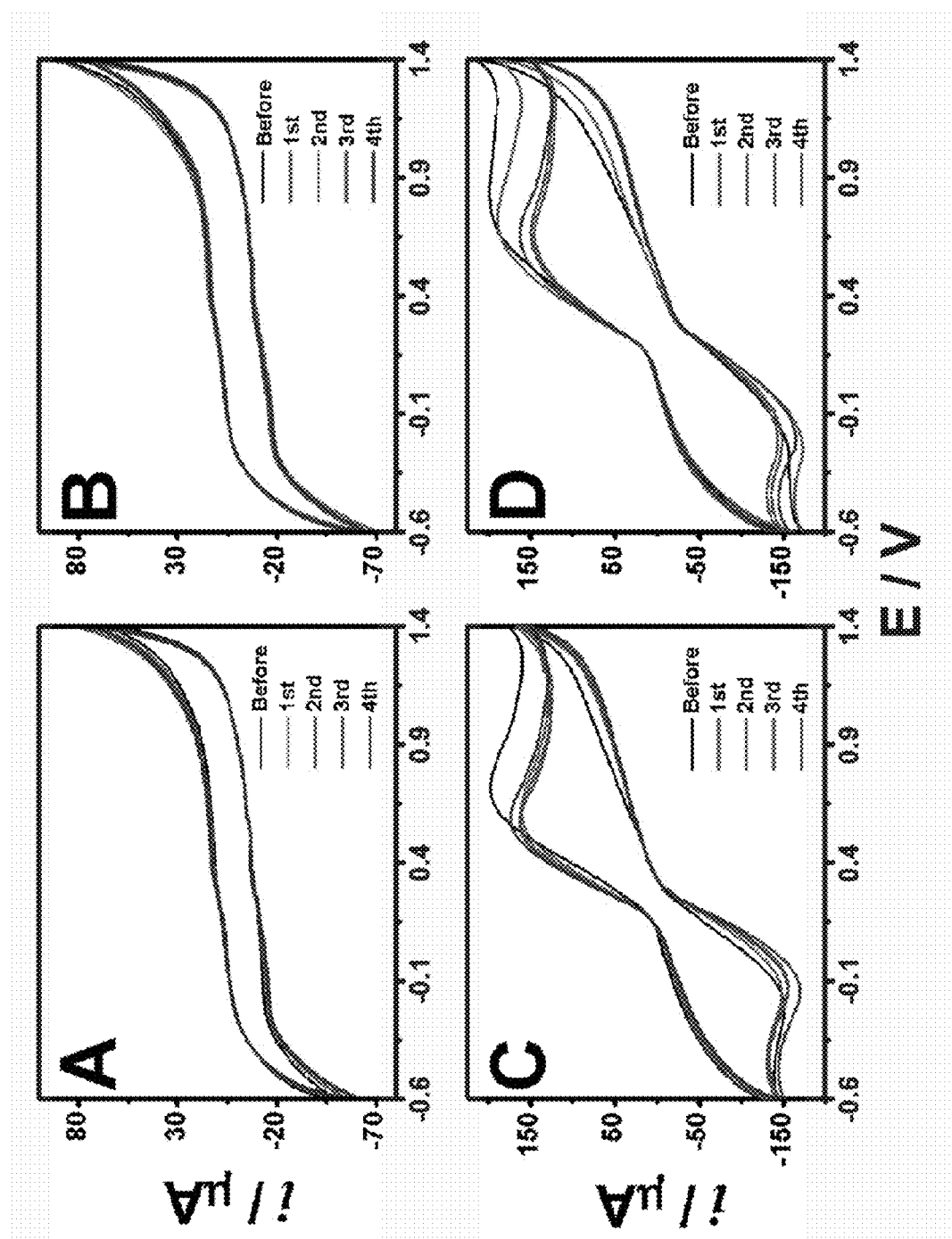
FIGS. 4A, 4B, 4C, and 4D

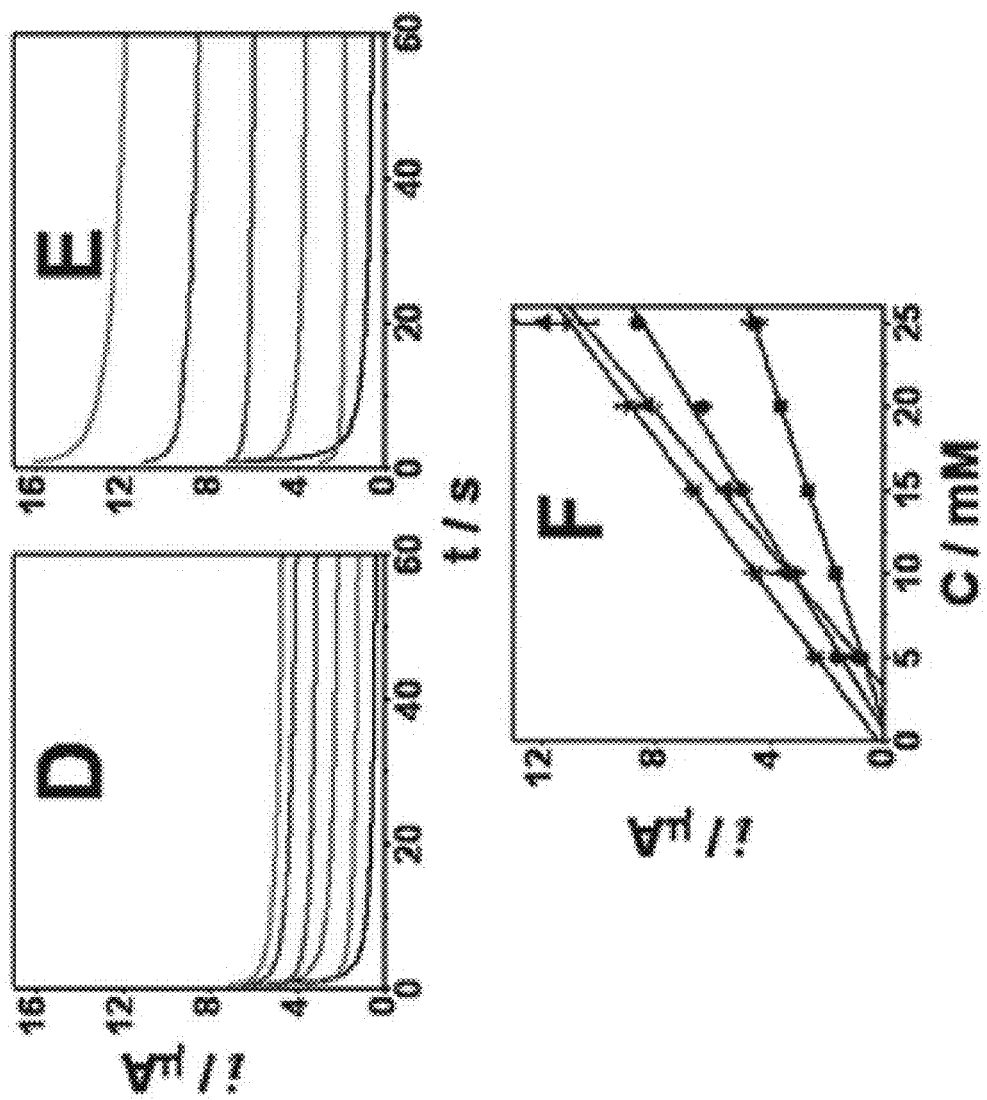
FIGS. 5D, 5E, and 5F

Microscopic images (top-view) of the printed carbon electrodes on (A) MERONA (B) COVINGTON textile substrates, as well as on a plastic Mylar substrate (C).

Screen-Printed Sensors on the Goretex based Fabric
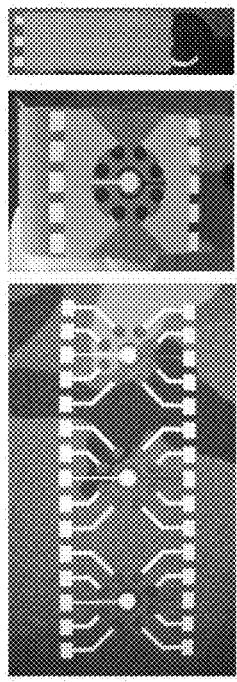
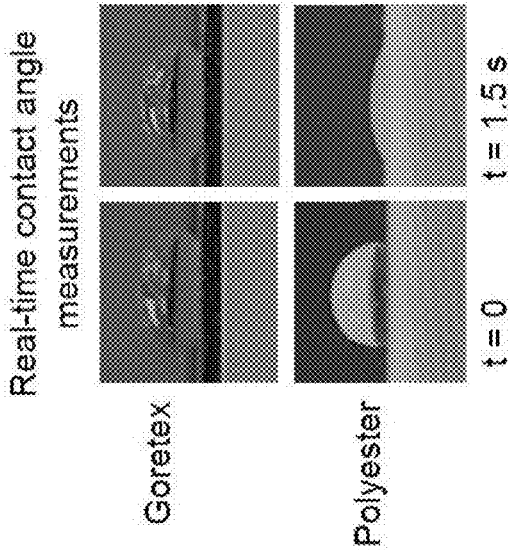
Real-time contact angle measurements
FESEM images
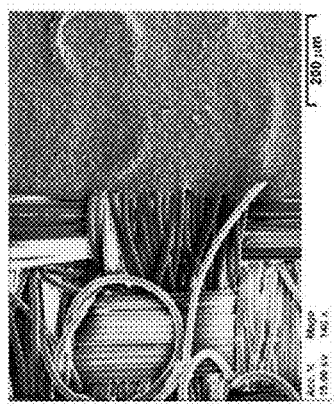
Screen Printed Carbon electrode on Goretex
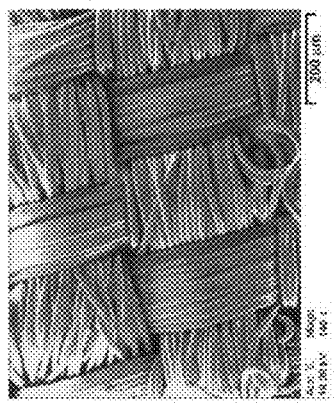
Goretex
FIG. 8

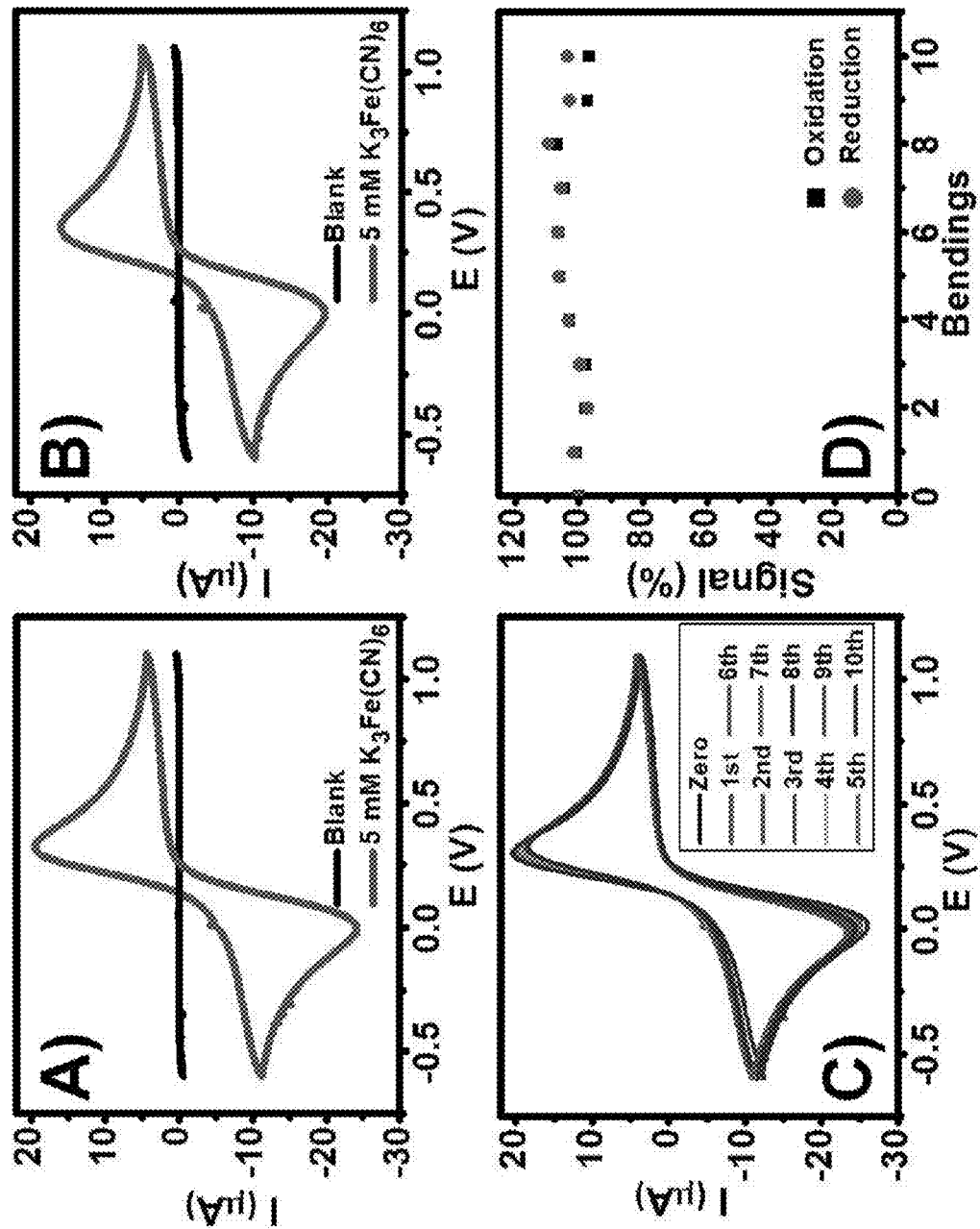
FIGS. 19A, 19B, 19C, and 19D

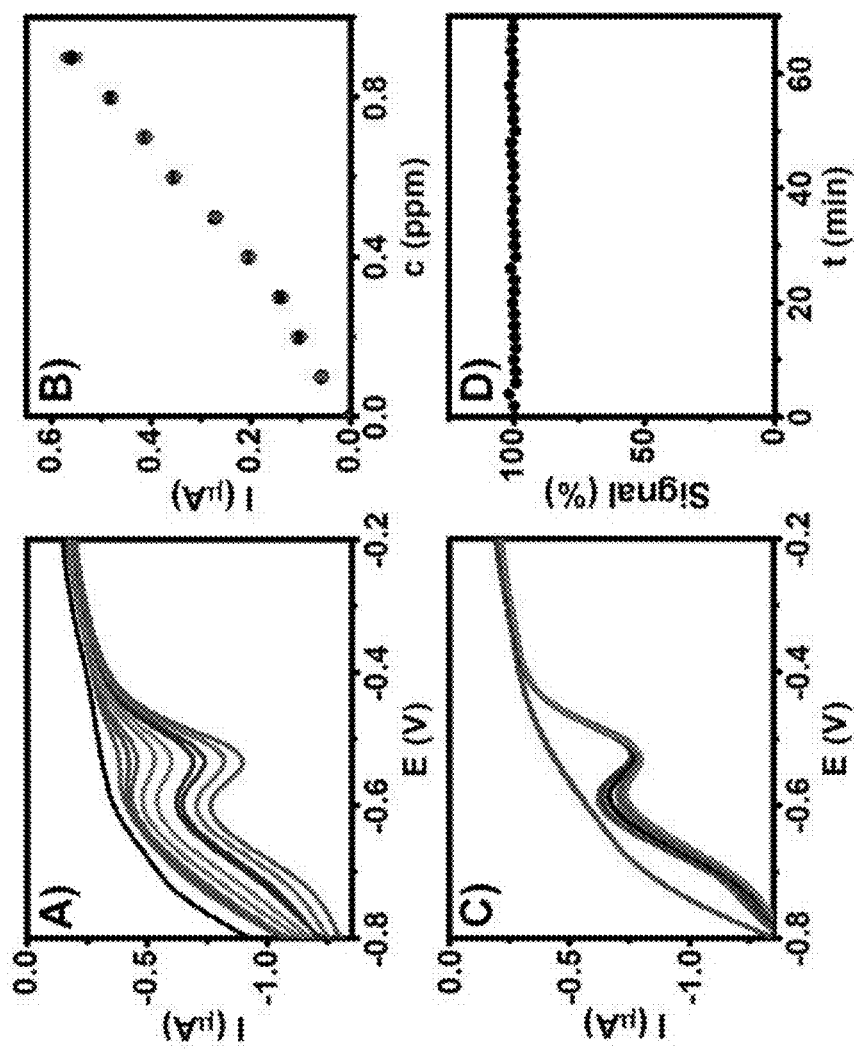
FIGS. 22A, 22B, 22C, and 22D

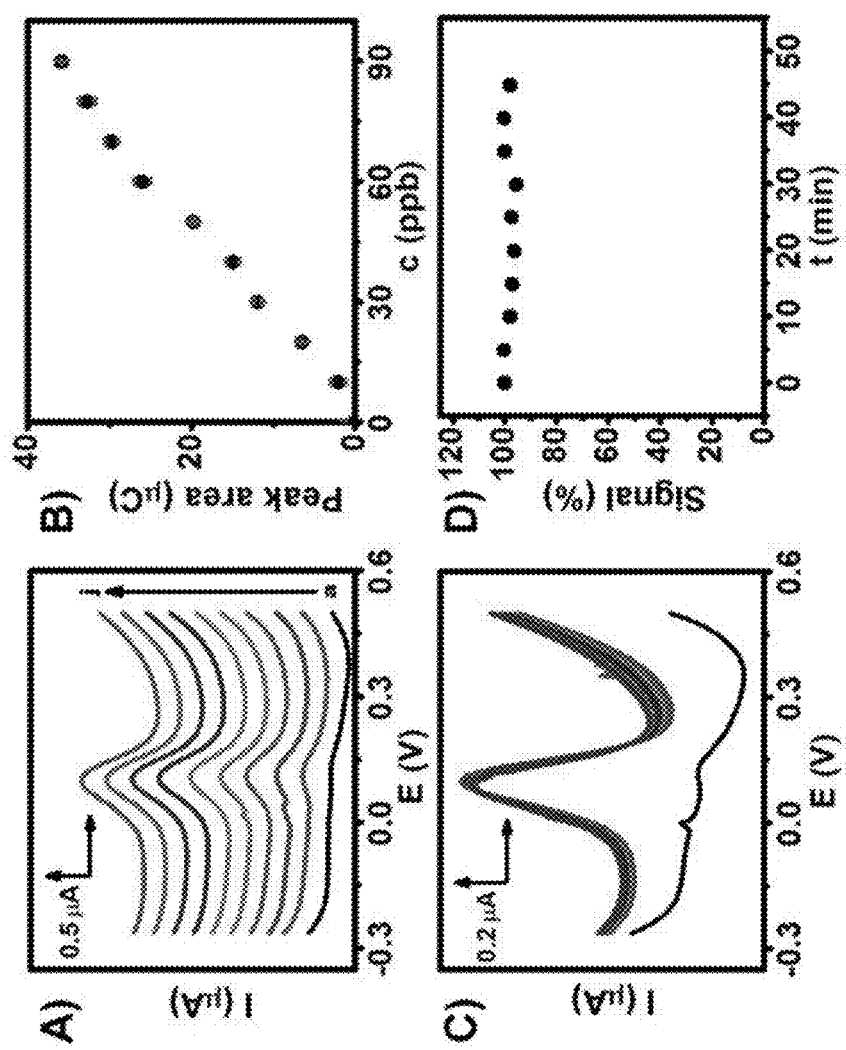
FIGS. 23A, 23B, 23C, and 23D

TEXTILE-BASED PRINTABLE ELECTRODES FOR ELECTROCHEMICAL SENSING

CROSS-REFERENCE TO RELATED PATENT APPLICATIONS

This application claims the benefit of priority from U.S. Provisional Patent Application Ser. No. 61/353,581, entitled "TEXTILE-BASED PRINTABLE ELECTRODES FOR ELECTROCHEMICAL SENSING," filed on Jun. 10, 2010, and U.S. Patent Application Ser. No. 61/354,157, entitled "TEXTILE-BASED PRINTABLE ELECTRODES FOR ELECTROCHEMICAL SENSING," filed on Jun. 11, 2010, both of which are incorporated by reference in the present patent application.

STATEMENT REGARDING FEDERALLY SPONSORED RESEARCH OR DEVELOPMENT

This invention was made with government support under Grant No. N00014-08-1-1202 awarded by the Office of Naval Research. The government has certain rights in the invention.

BACKGROUND

This application relates to devices and techniques that use electrochemical technologies, including sensors printable on textile.

Various healthcare monitoring systems are available for home-based or personal management of healthcare. Efforts in this direction commonly incorporate physical sensors into clothing for monitoring of vital signs. Little attention has been given to wearable chemical sensors despite the fact that electrochemical sensing devices are ideally suited for meeting the requirements of on-body physiological monitoring.

SUMMARY

Techniques and systems and apparatus are disclosed for implementing textile-based screen-printed amperometric sensors.

The subject matter described in this specification potentially can provide one or more of the following advantages. For example, the described techniques, systems and apparatus can be used to implement direct screen printing of amperometric and potentiometric sensors onto clothing and the favorable electrochemical behavior of such textile-based sensors. The described textile-based printed sensors can survive large deformations and to display an attractive current signals to various biomolecules and chemicals. Printed electrodes can be compatible with clothing substrates. Additionally, the disclosed textile-based screen-printed (thick-film) electrochemical sensors can offer great promise for wide range of future commercial applications, relevant to healthcare/personalized medicine, sport, military, security or environmental applications including detection of toxic gases and chemical agents (e.g. nerve agents) and explosive threat sensing. The latter has been demonstrated for TNT and DNT in liquid and gas phase detected by chemical sensors printed on Gore-Tex. The described techniques, apparatus and systems can provide clothing-integrated support electronics, display, power and communication functions.

In one exemplary aspect, a chemical sensor incorporated into textile or clothing is disclosed. The chemical sensor comprises at least one of an amperometric sensor and a potentiometric sensor.

In another aspect, a method of sensing a chemical using a textile-incorporated sensor is disclosed.

In yet another aspect, a method of incorporating a chemical sensor into textile is disclosed. An ink formulation is selected based on a type of textile and a type of chemical to be sensed. A viscosity of the ink formulation is selected for mechanical robustness when the ink formulation is applied to the textile. The ink is printed onto the textile.

In yet another aspect, a chemical sensor incorporated into specific clothing elements including at least one of an undergarment waistband, a bra strap, a cuff a sock, a wristband, an armband, a headband, and a collar for optima on-body contact is disclosed.

In yet another aspect, a textile-integrated chemical sensor system includes a wearable textile material, a chemical sensor incorporated onto the textile material and electronic equipment for displaying and communicating results of sensing by the chemical sensor.

In yet another aspect, a textile-integrated chemical sensor is configured to perform at least one of the following operations: sweat monitoring for alcohol levels, performance/stress/exertion levels, incontinence products, wearable heart-rate, blood-pressure, other healthcare-related monitoring, detection of toxic gases and chemical agents, and explosive threat sensing.

In yet another aspect, a method of producing an explosive detection product comprises patterning an electrochemical sensor onto fabrics such that the electrochemical sensor is capable of detecting gas or liquid phase explosive chemicals.

In yet another aspect, a process of fabricating a product for underwater sensing of chemicals includes printing an electrode on a wearable material and printing a catalyst-containing ink onto the electrode.

In yet another aspect, a wearable garment product includes a substrate comprising a garment material, an electrode printed on the substrate and a catalyst-containing ink printed onto the electrode.

BRIEF DESCRIPTION OF THE DRAWINGS

FIGS. 3A, 3B, 3C and 3D show effect of repetitive bending of sensor printed on underwear upon the cyclic voltammetric background (pH 7 phosphate-buffer, 0.1M) response (FIG. 3A, FIG. 3B) and the response for 5 mM ferrocyanide (FIG. 3C, FIG. 3D), bending time, 5 s; bending angle, 180° (inward); release time, 10 s; scan rate, 0.1 V/s. Underwear brand: MERONA (FIG. 3A, FIG. 3C) and COVINGTON (FIG. 3B, FIG. 3D).

FIGS. 4A, 4B, 4C and 4D show effects of repetitive stretching on the cyclic voltammograms of MERONA—(FIG. 4A, FIG. 4C) and COVINGTON—(FIG. 4B, FIG. 4D) based electrodes for the background phosphate buffer (FIG. 4A, FIG. 4B) and 5 mM ferrocyanide (FIG. 4C, FIG. 4D); stretching time, 5 s; release time, 10 s; stretching load was applied to whole electrode in horizontal direction with a strain of 1.53. Other conditions, as in FIGS. 3A-D.

FIGS. 5A, 5B, 5C, 5D, 5E and 5F show chronoamperometric response of the MERONA-based electrodes to ferrocyanide (FIG. 5A, FIG. 5B) and hydrogen peroxide (FIG. 5D, FIG. 5E) solutions before (FIG. 5A, FIG. 5D) and after 2 stretching steps (FIG. 5B, FIG. 5E). FIG. 5C and FIG. 5F show the corresponding calibration plots before stretching (square), and after the first (cycle) second (triangle) stretching. Stretching time, 5 s. Release time, 10 s. Average Strain, 1.53.

(FIG. 6A) Linear scan voltammograms recorded at MERONA-based electrodes for increasing levels of NADH in 20 µM steps, along with the resulting calibration plot (inset). Chronoamperometric curves of increasing NADH concentrations (in 0.1 mM steps) of before (FIG. 6B) and after 2 stretching (FIG. 6C) steps. Stretching time, 5 s. Release time, 10 s. Strain, 1.53.

FIG. 8 shows an example of sensors screen-printed on a Gore-Tex based fabric.

(FIG. 13A) GORE-TEX, (FIG. 13B) 100% polyester, and (FIG. 13C) 100% cotton fabrics. Scan rate, 100 mV s−1 for i and ii, 300 mV s−1 for iii and iv.

(FIG. 15A) and TNT (FIG. 15B) in 0-50 µg/mL (i→v) and corresponding calibration plots (right). Increasing potential step, 4 mV; Amplitude, 25 mV; Frequency, 20 Hz. Current in calibration plots are sampled at −0.86 (FIG. 15A) and −0.75 V (FIG. 15B).

FIG. 18A shows screen printed electrodes (SPE) on an underwater garment. The three-electrode configuration comprises an Ag/AgCl reference electrode as well as a carbon working and counter electrodes printed directly onto neoprene. Center: Two different SPE designs on neoprene. FIG. 18B shows a three electrode configuration equivalent to (FIG. 18A) comprising an additional insulator layer (blue); FIG. 18C Array of 4 silver electrodes (the feature width of each contact line is ~195 µm, the pitch between adjacent electrodes is ~280 µm, and the diameter of the active area of each electrode is ~440 µm). FIG. 18D Scanning electrode micrograph illustrating the working electrode area on a neoprene substrate (42×, 5 kV).

FIGS. 19A, 19B, 19C and 19D show the following. Cyclic voltammograms for 5 mM ferricyanide at SPE on flexible neoprene (FIG. 19A) and rigid alumina (FIG. 19B) substrates. (FIG. 19C) Voltammogram illustrating the effect of ten repeated bending operations. (FIG. 19D) Relative currents obtained for the redox peaks of 5 mM ferricyanide extracted from the repetitive bending data presented in FIG. 19C). Scan rate, 50 mV/s.

FIG. 28a shows phenol, FIG. 20B shows 4-chlorophenol, and FIG. 20C shows catechol curves. The insets show the corresponding calibration curves. FIG. 20D shows the stability of the signal over time with respect to the initial measurement at t=0 min (100%) for (i) 10 µM 4-chlorophenol and (ii) 2 µM phenol.

FIGS. 22A, 22B, 22C and 22D show square-wave voltammograms for TNT in seawater recorded at the neoprene SPE. FIG. 22A shows response for increasing levels of TNT from 100 to 900 ppb (Frequency, 20 Hz; step amplitude, 25 mV; step increment, 4 mV). FIG. 22B shows a calibration curve corresponding to FIG. 22A. FIG. 22C shows stability of the sensor with 500 ppb TNT over a period of one hour (n=30). FIG. 22D shows stability of the signal over time with respect to the initial measurement at t=0 min (100%). Also shown are the corresponding voltammograms for the unspiked seawater.

FIGS. 23A, 23B, 23C and 23D are as follows. FIG. 23A depicts Square-wave (SW) stripping voltammograms for trace copper in untreated seawater at the Au-modified neoprene SPE. FIG. 23B shows a response to increasing copper concentrations in 10 ppb steps. Deposition for 2 min at −1.0V (vs Ag/AgCl) under quiescent conditions followed by SW scan from −0.25 to 0.50 V (fSTEP=10 Hz, 25 mV step amplitude, 4 mV step potential). FIG. 23C shows a calibration curve corresponding to the stripping peak area vs. the copper concentration (average of three repetitive measurements). FIG. 23D is a graphical representation of the stability of the system with 100 ppb copper over a 50 minutes period. Stability of the signal over time is depicted with respect to the initial measurement at t=0 min (100%).

Like reference symbols and designations in the various drawings indicate like elements.

DETAILED DESCRIPTION

Figure 1A:
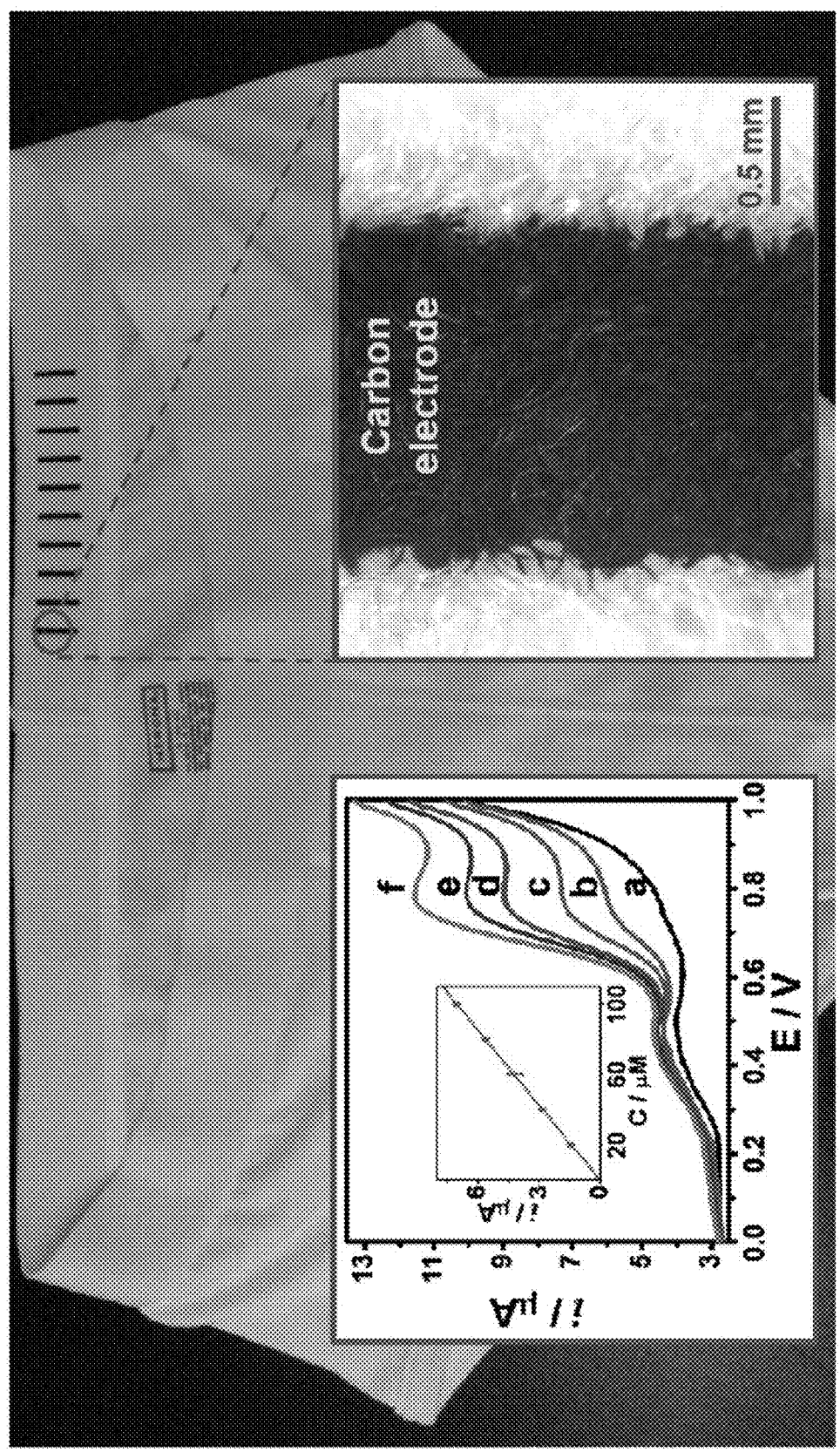
FIGS. 1A and 1B are images of the screen-printed carbon electrodes on the underwear (MERONA Ultimate Briefs brand) (Background) along with the morphology of a single electrode (Right inset) and linear-scan voltammetric response for increasing NADH concentrations over the 0-100 µM range (Left inset).

The techniques, apparatus and systems described in this application can be used to implement textile-based, screen-printed sensors such as amperometric sensors.

Disclosed are thick-film amperometric and potentiometric sensors that are screen-printed directly on textiles and exhibit electrochemical and mechanical properties which enable their use in clothing-integrated healthcare, sports, military, security, and related applications. Early proof of concept has been accomplished with carbon electrodes printed on elastic waistbands of underwear: these tested favorably in the laboratory for electrochemical performance (sensing of NADH and hydrogen peroxide which are products of numerous biocatalytic reactions, and potassium ferrocyanide, a common redox marker and mediator) under various conditions of deformation (folding, stretching, sticking). Even better results were more recently obtained with electrodes printed on Gore-Tex. Hydrophobic textiles like Gore-Tex lead to reproducible results because they are more robust to constant exposure to liquids of the electrode/textile interface. The described techniques can provide printing protocols and ink formulations and viscosities tailored for specific substrate textile materials to optimize printing quality and electrochemical/mechanical sensor performance. In one embodiment elastic-band-based sensors include a chemically-selective layer (e.g., permselective coating or enzyme layer) and are used for direct sweat monitoring. For example, dehydrogenase- and oxidase-based enzyme sensors for ethanol and lactate, respectively, are implemented to monitor alcohol consumption in drivers or performance/stress of soldiers/athletes. Other personal and health care applications include incontinence products with printed sensors, and wearable health monitoring systems (e.g., heart-rate, blood-pressure sensing). Military/security/environment applications include detection of toxic gases and chemical agents (e.g., nerve agents) and explosive threat sensing which has been demonstrated for TNT and DNT in liquid and gas phase detected by chemical sensors printed on Gore-Tex. The described techniques, apparatus and systems can also include clothing-integrated supporting electronic, display, power and communication functions.

In one aspect, the incorporation of amperometric sensors into clothing through direct screen-printing onto the textile substrate is described. Particular attention is given to electrochemical sensors printed directly on the elastic waist of underwear that offers tight direct contact with the skin. The textile-based printed carbon electrodes have a well-defined appearance with relatively smoothed conductor edges and no apparent defects or cracks. Convenient voltammetric and chronoamperometric measurements of 0-3 mM ferrocyanide, 0-25 mM hydrogen peroxide, and 0-100 μM NADH have been documented. The favorable electrochemical behavior is maintained under folding or stretching stress, relevant to the deformation of clothing. The electrochemical performance and tolerance to mechanical stress are influenced by the physical characteristics of the textile substrate. The results indicate the potential of textile-based screen-printed amperometric sensors for future healthcare, sport or military applications. Such future applications would benefit from tailoring the ink composition and printing conditions to meet the specific requirements of the textile substrate.

In another aspect, incorporation of chem-/biosensing devices into textiles through screen-printing technology is described. Specific attention is given in the present document to the high-fidelity detection of explosive agents employing a fabric-based sensor. Common fabrics and commercially-available textile materials are evaluated, and the waterproof fabric GORE-TEX® is found to be the optimal substrate/platform for the liquid- and gas-phase monitoring of explosive materials in the field. The GORE-TEX® fabric-based printed electrodes exhibit high-fidelity sensing abilities for 2,4-dinitrotoluene (DNT) and 2,4,6-trinitrotoluene (TNT) explosive agents. 0-50 μg/mL levels of both DNT and TNT in the solution-phase are detected using square-wave voltammetry. Repeated tests of these explosive agents on the printed electrodes, furthermore, has confirmed the analytical repeatability of the sensors under typical wear. The GORE-TEX® fabric-based sensor is also shown to be able to detect the vapor generated from 60 mg of DNT powder in a sealed 30 mL container. The results indicate the potential of textile-based screen-printed sensors for future security and military applications. Such future applications would benefit from the integration of the appropriate miniaturized electronic control and readout, enabling true field-based utility.

In yet another aspect, wearable screen-printed electrochemical sensors on underwater garments comprised of the synthetic rubber neoprene are disclosed. These wearable sensors are able to determine the presence of environmental pollutants and security threats in marine environments. Owing to its unique elastic and superhydrophobic morphology, neoprene is an attractive substrate for thick-film electrochemical sensors for aquatic environments and offers high-resolution printing with no apparent defects. The neoprene-based sensor was evaluated for the voltammetric detection of trace heavy metal contaminants and nitroaromatic explosives in seawater samples. We also describe the first example of enzyme (tyrosinase) immobilization on a wearable substrate towards amperometric biosensing of phenolic contaminants in seawater. Furthermore, the integration of a miniaturized potentiostat directly on the underwater garment is demonstrated. The wearable sensor-potentiostat microsystem provides a visual indication and alert if the levels of harmful contaminants have exceeded a pre-defined threshold. The concept discussed here is well-suited for integration into dry- and wetsuits worn by divers and recreational surfers/swimmers, thereby providing them with the ability to continuously assess their surroundings for environmental contaminants and security hazards.

The described techniques, apparatus and systems can address the shift in focus on healthcare shifts from centralized hospital-based treatment to home-based management by providing reliable, wearable healthcare monitoring systems. Such on-body (non-invasive or minimally-invasive) physiological monitoring devices may also be of considerable interest for defense or sport applications. Integrating sensors and biosensors directly into clothing should thus can have major advantages for future healthcare and soldier monitoring systems. However, the successful realization of such textile-based biomedical sensors many need to include proper attention to the effect of the fabric morphology and of the continuous deformation of such clothing (associated with the body movement and the wearer's daily activity) upon the sensor performance. The growing interest in on-body physiological monitoring devices reflects also the tremendous recent attention to flexible electronics3 and wearable electronics. Such integration of electronics into clothing opens up numerous opportunities in a variety of fields. Compared to wearable entertainment systems, on-body healthcare monitoring devices should be highly robust and durable in connection with the wearer's daily activity. Early efforts in this direction have integrated physical sensors into clothing for monitoring continuously vital signs such as blood pressure or heart rate. Yet, little attention—focusing primarily on ion-selective potentiometric sensors—has been given to wearable chemical sensors. Such activity involved integrating materials, such as conducting polymers or carbon nanotubes, into the fabric.

In another aspect, the present specification describes the fabrication of thick-film amperometric sensors and biosensors directly onto clothing structures and assesses the influence of the clothing deformation upon the performance of such textile-based electrochemical sensors. Electrochemical sensing devices have played a leading role in the move towards point-of-care diagnostics and are ideally suited for meeting the requirements of on-body physiological monitoring. The screen-printing (thick-film) microfabrication technology has been widely used for over two decades for the large-scale mass production of electrochemical sensor strips. Effective screen-printed electrochemical sensors have been fabricated on various flexible substrates ranging from Kapton® to Mylar®, with the sensor bending displaying minimal effect on the analytical performance. Screen-printing technology was also used recently for fabricating electrodes on paper-based microfluidic devices. Similarly, the screen-printing process has been widely used for creating various logos and images on clothing (particularly T-shirts) and more recently for creating flexible printed circuits. Capacitive sensors were recently screen-printed on clothing and used for monitoring respiration.

Unlike conventional screen-printed strip electrodes, textile-based thick-film sensors rely on porous substrates and must survive large deformations. In the following sections we will describe the preparation and characterization of textile-based amperometric sensors (e.g., FIGS. 1A and 1B), illustrate their favorable electrochemical behavior and examine the influence of the clothing stretching and folding upon their sensing performance. To our knowledge, this is the first example of textile-based screen-printed amperometric sensors and of studying the role of the clothing deformation upon the resulting performance. The elastic waistband of common underwear has been selected as model clothing owing to its tight contact and direct exposure with the skin, and hence for its potential for direct sweat monitoring. While the present study aims at characterizing the behavior of the textile-based screen-printed electrode transducers (particularly in connection to the clothing deformation), future efforts will focus on such on-body sensing in connection to relevant chemically selective layers, towards textile-based healthcare and soldier monitoring systems.

The described techniques, apparatus and systems can address the desire to obtain greater information regarding the health and surroundings of individuals. For example, advanced electrochemical sensors for medical, environmental, industrial, and security applications can be implemented. Of the possible paradigms available, the integration of sensing devices with textiles is one of the most promising platforms for the realization of wearable sensor devices. Fabrics present many unique opportunities and advantages that can be exploited for various applications and are especially suited to handle the rigors of field-based use where durability and light-weight are core requirements. Such sensor devices are well-positioned to enable "wear and forget" functionality, thereby permitting the wearer to go about their routine and only receive alerts during situations that require the user's attention or intervention.

In addition to monitoring personal health, the described techniques, apparatus and systems can be used to implement wearable sensors that monitor the wearer's local environment in order to identify particularly hazardous conditions. Such textile-based electrochemical sensors can be implemented by making careful selection of the fabrics/textiles on which the sensing reaction occurs. Particular attention should be given to both the physical (i.e. morphology) and chemical (i.e. composition) properties of the fabrics. The optimal textile candidate would possess inert properties and yield stable operation for extended periods of time under normal and heavy wear. Additionally, liquid-phase measurements require the utilization of water-proof fabrics, which would serve as excellent platforms for facilitating chemical reactions in vitro.

Homemade explosives are, by far, the most common means to inflict death and destruction in terrorist attacks. Common constituents of homemade explosives include urea nitrate, triacetone triperoxide (TATP), hexamethylene triperoxide diamine (HMTD), 2,4-dinitrotoluene (DNT), and 2,4,6-trinitrotoluene (TNT), among others. Due to the innate ability of DNT and TNT to withstand impact and friction, these compounds have witnessed wide use in explosives as a consequence of the reduced risk of accidental detonation during manufacture and handling. Additional desirable properties of these explosive materials are their stability, ease of mixture with other explosives, and water insolubility, making them especially useful for wet environments.

Whereas previous studies of chemical sensing on textiles was intended for the physiological monitoring of the wearer (i.e. sensing on the interior waistband of undergarments), the described techniques, apparatus and systems can be used to provide textile-based chemical monitoring of explosives that the wearer may be exposed to in their environment. This application requires a dense, hydrophobic outer surface with desirable morphology such that conventional screen-printing technologies can be leveraged. Therefore, in one aspect, described is a characterization of the behavior of textile-based screen-printed electrodes as applied to explosive sensing in the liquid- and gas-phases, particularly in connection with the properties of the fabric substrate. The fabrics that can be used include cotton, polyester, and GORE-TEX®, a widely used constituent of outdoor garments. GORE-TEX® fabric, a textile known for its exceptional breathable and water-proof properties, is shown to be a promising substrate for the fabrication of explosive sensors. Additionally, the described, techniques, systems and apparatus can address the integration of an electronic backbone with the electrodes and immobilization of enzymes in order to realize true lab-on-a-textile functionality. Moreover, the described techniques, apparatus and systems can target the detection of additional chemical agents of importance in security applications.

With reference at least to FIGS. 1A, 1B, 2A, 2B, 2C, 3A, 3B, 3C, 3D, 4A, 4B, 4C, 4D, 5A, 5B, 5C, 5D, 5E, 5F, 6A, 6B, 6C, 7A, 7B, 8, 9A, 9B and 10, certain devices and techniques are now described.

Materials and Methods

Chemicals and Materials

Potassium ferrocyanide was obtained from Fisher Scientific (Fair Lawn, N.J.). —Nicotinamide adenine dinucleotide, reduced dipotassium salt (NADH) and hydrogen peroxide (H2O2) were purchased from Sigma-Aldrich (St. Louis, Mo.) and were stored in a refrigerator before use. Deionized water (>18 M cm), from a NANOpure Diamond system (Thermo Scientific Barnstead, Waltham, Mass.), was used to prepare all solutions. Electrochemical measurements were carried out in a 0.1 M phosphate buffer (pH 7.0). Two brands of underwear, MERONA® Ultimate Briefs and COVINGTON® Briefs, were purchased from local department stores.

Preparation of Sensing Electrodes

Figure 1B:
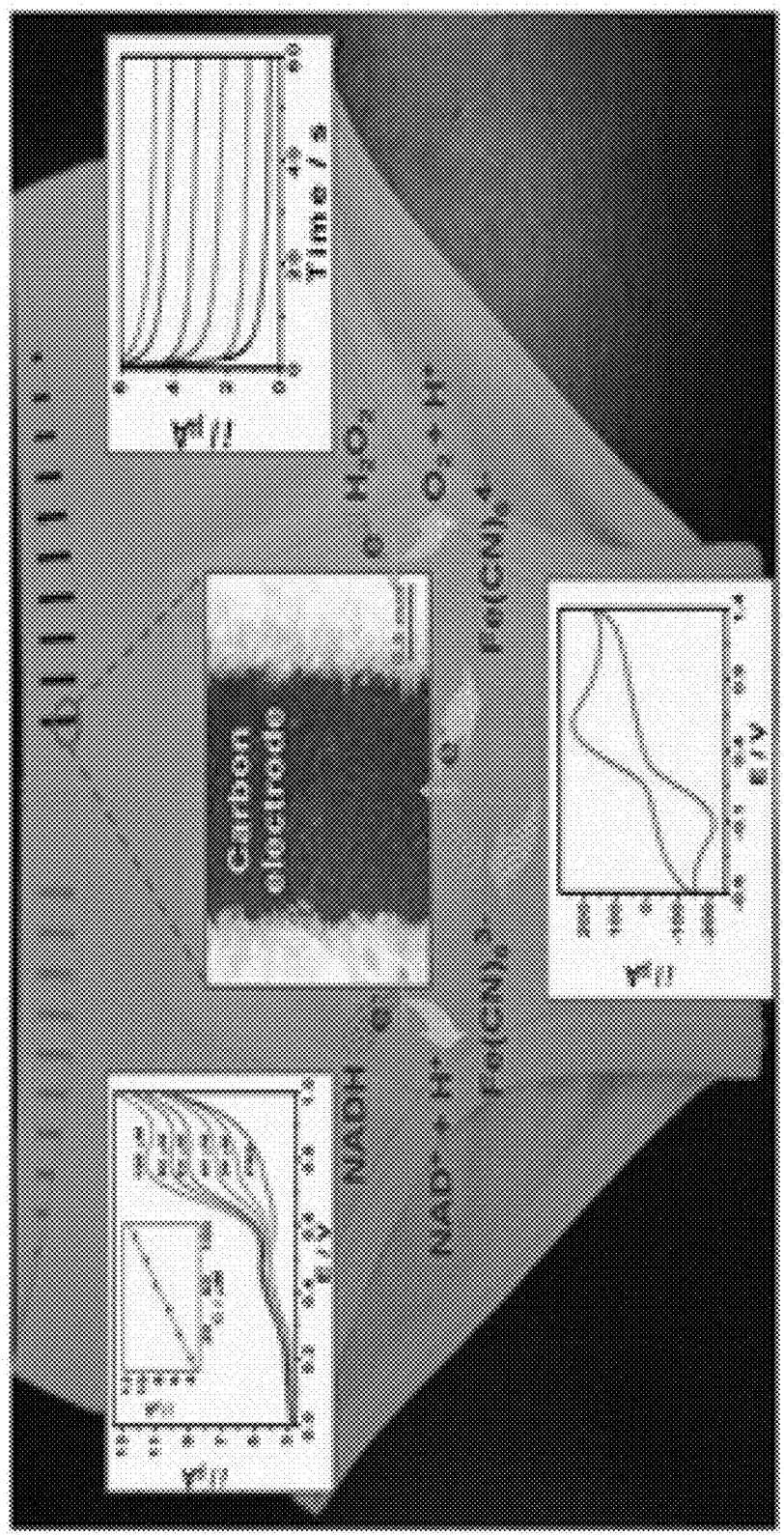

A semi-automatic screen-printer (Model TF 100; MPM, Franklin, Mass.) was used to print ca. 75 m-thick carbon electrodes. Carbon-based ink (E3449; Ercon, Wareham, Mass.) was printed through a patterned stencil forming a 10 rectangular carbon electrode array (each of 1.5 mm×15 mm) onto the inner side of the elastic band of the underwear (see FIGS. 1A and 1B). Subsequent to the printing process, the patterned waistband was cured for 20 min at 120° C. All tests and electrochemical measurements were carried out after cutting the waistband into 6×20 mm strips containing the individual 1.5 mm×15 mm working electrodes. A magnified image of a typical textile-based printed carbon electrode is shown in FIG. 1A (right inset). FIGS. 1A and 1B are images of the screen-printed carbon electrodes on the underwear (MERONA Ultimate Briefs brand) (background) along with the morphology of a single electrode (right inset) and linear-scan voltammetric response for increasing NADH concentrations over the 0-100 M range (left inset).

Apparatus and Measurements

To understand the bending effect upon the electrochemical/sensing behavior of electrode, the bending was only applied on the 6 mm-long electrode section exposed to the test solution (3 mm away from the bottom of the carbon electrode). Bending was applied with inward 180° for 5 s. Multiple bending were separated with 10 sec release intervals. Stretching of the electrode was carried out in the horizontal direction (using an average strain of 1.53 as was measured with a ruler). Each stretch was held for 5 s, along with an intermittent 10 s release. Adhesion tests were conducted using a 3M scotch-tape (Magic, Scotch, 3M St. Paul, Minn.), pressed down onto the electrodes and removed quickly. The morphology of the electrode was examined (after the bending or stretching) by the optical microscope (SZ-45-PS, CALTEX Scientific Inc., Irvine, Calif.). The resistance of the textile-based carbon electrode was measured using a digital multimeter (Elenco LCM-1950; Elenco Electronics, Wheeling, Ill.) with probing at 6 mm apart.

All electrochemical measurements were performed at room temperature using a 620A Electrochemical Analyzers (CH Instruments, Austin, Tex.). A typical three-electrode cell (5 mL beaker) was used, along with a 0.25 mm diameter platinum wire counter electrode and a Ag/AgCl reference electrode (CHI111, CH Instruments). The textile-based printed carbon working electrode was immersed into the test solution (by dipping 6 mm of its length). The Ag/AgCl and Pt reference and counter electrodes, respectively, completed the three-electrode cell. To avoid background contributions from the alligator clip connector (to the textile-based electrode), its surface was precoated manually with the carbon ink that was cured for 20 min at 120° C. Cyclic voltammetry (CV) or chronoamperometry was used to evaluate the effect of the surface bending and stretching on the performance of the textile-based electrode. To ensure consistent wetting (reproducible electrode exposure), due to absorption of the test solution by the textile, all electrochemical measurements were carried out at a fixed time (60 sec) after immersing the electrode in the sample. Chronoamperometric currents were sampled 60th sec after the potential step.

Results and Discussion

Figures 2A, 2B, 2C:
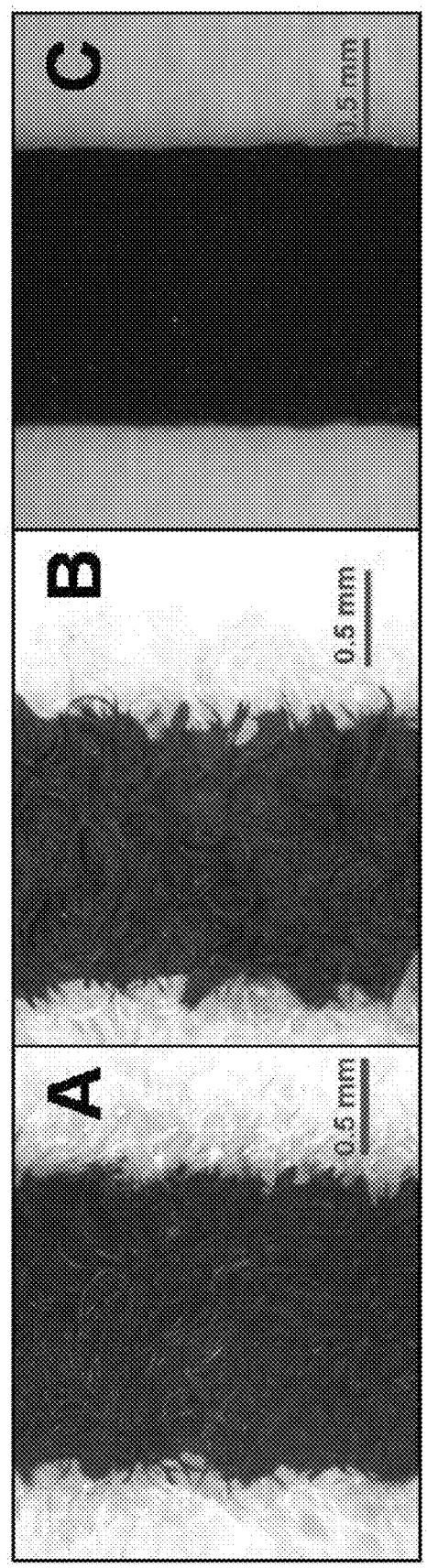
FIGS. 2A, 2B and 2C are top-view microscopic images of the printed carbon electrodes on MERONA—(FIG. 2A, FIG. 2D) or COVINGTON (FIG. 2B) textile substrates, as well as on a plastic Mylar substrate (FIG. 2C).

We employed common screen-printing protocols in connection with the textile substrate. Printing and curing conditions, recommended by the ink manufacturer for printing on traditional alumina or polymeric substrates, were used for printing the carbon electrodes on the elastic band of the underwear substrates (FIGS. 1A and 1B). The resulting electrodes were mechanically strong and possess good adhesion to the textile substrate, with no apparent peeling or cracking FIGS. 2A, 2B, and 2C are top-view microscopic images of the printed carbon electrodes on MERONA (FIG. 2A) or COVINGTON (FIG. 2B) textile substrates, as well as on a plastic Mylar substrate (FIG. 2C). FIGS. 2A, 2B, and 2C compare microscopic images of carbon electrodes printed on different underwear brands (FIGS. 2A and 2B) to those of a carbon strip fabricated under the same conditions using a conventional plastic (Mylar) substrate (FIG. 2C). The textile-based printed sensing electrodes (line width, 1.5 mm) have a well-defined appearance with a continuous conducting surface, relatively smooth conductor edges and no apparent defects or cracks. The electrode surface is characterized by a microporous fibrous structure, reflecting the morphology of the substrate, with microfibers of relatively uniform dimensions and distribution. In contrast, the electrode printed on the traditional (Mylar) substrate (FIG. 2C) displays a higher printing resolution (with smoother edges) and a flat, highly dense (less porous) surface of interconnected granules. The higher roughness of the textile-based sensor reflects the porosity of the underwear substrates and the ink penetration into the fabric. Similar observations were reported for the textile-based printing of silver lines for electrical circuits 16. Note also the different topographies and edge resolution of the MERONA- and COVINGTON-based electrodes that reflect the different porosities of these fabric brands (with the MERONA substrate characterized with a higher thread count and smoother and denser surface). While the textile substrates lead to decreased conductor edge resolution (compared to the conventional plastic substrate), line widths of smaller than 250 m are still expected based on the printing resolution of FIG. 2A. Tailoring the ink composition to specific textile substrates should lead to enhanced printing quality and resolution. A preliminary Scotch-tape-based adhesion peel test, conducted to evaluate the adhesion of printed electrodes on the textile substrate, indicated a satisfactory electrode adhesion to both underwear brands without notable damage or lift-off during five removals of the tape. These adhesion data are encouraging considering that denser and flat substrates commonly yield strong adhesion.

Folding or stretching of clothing, associated with normal daily activities of the wearer, may affect the microstructure and morphology of the textile-based sensor and hence its performance. The influence of such mechanical stress thus requires a detailed evaluation. The textile-based printed electrodes were thus subjected to successive bending and stretching steps and the influence of this mechanical stress upon the surface topography and electrochemical performance was examined.

Previous investigation has shown that bending of electrodes printed on plastic substrates has a negligible effect upon their electrochemical signal. Since electrodes printed on textiles have different microstructures and adhesion properties, we examined the influence of such mechanical stress upon their performance. FIGS. 3A-D are data graphs showing the effect of repetitive bending of sensor printed on underwear upon the cyclic voltammetric background (pH 7 phosphate-buffer, 0.1M) response (FIG. 3A, FIG. 3B) and the response for 5 mM ferrocyanide (FIG. 3C, FIG. 3D). Bending time is 5 s; bending angle is 180° (inward); release time is 10 s; and scan rate is 0.1 V/s. The underwear brand for FIGS. 3A and 3C is MERONA and COVINGTON for FIGS. 3B and 3D. Thus, FIGS. 3A, 3B, 3C, and 3D illustrate the influence of the bending-induced mechanical stress upon the electrochemical response of the textile-based screen printed electrodes. It displays cyclic voltammograms for the phosphate-buffer background (FIGS. 3A and 3B) and potassium ferrocyanide (FIGS. 3C and 3D) solutions in connection to repetitive (5 sec) bending steps. The maximum possible inward bending of the printed electrodes (a 180° inward folding) was selected for illustrating the most severe mechanical stress (i.e., maximum possible clothing deformation). For both underwear-based sensors, such repetitive and extreme bending steps have a negligible effect upon the background response, with the exception of a slightly decreased current using the MERONA-brand substrate (FIG. 3A). Similarly, both textile-based electrodes display defined CV response for ferrocyanide (FIGS. 3C and 3D), with the MERONA substrate exhibiting a smaller $\Delta Ep$ of 650 mV (vs. 750 mV for the COVINGTON brand). The peak potentials and currents are only slightly affected by the repetitive bending steps, although a slightly larger irreproducibility in the current intensities is observed for the COVINGTON brand. Note, however, that both textile substrates offer quite similar CV peak currents as well as background signals. The bending stress also yielded minimal changes in the electrode resistance. The reproducible data (in connection to the severe mechanical stress) reflect also the overall reproducibility of the experimental protocol, including consistent wetting of the electrode.

Textile stretching represents another mechanical stress associated with daily activity and clothing deformation. In comparison to bending, stretching is more likely to damage the textile-based printed electrode. FIGS. 4A, 4B, 4C, and 4D show the effects of repetitive stretching on the cyclic voltammograms of MERONA (A, C) and COVINGTON (FIGS. 4B and 4D) based electrodes for the background phosphate buffer (FIGS. 4A and 4B) and 5 mM ferrocyanide (FIGS. 4C and 4D). The stretching time is 5 s and the release time is 10 s. Stretching load was applied to the whole electrode in the horizontal direction with a strain of 1.53. Other conditions are as in FIGS. 3A, 3B, 3C, and 3D. Thus, FIGS. 4A, 4B, 4C, and 4D illustrate the influence of repetitive stretching of the textile-based printed electrodes upon their background (FIGS. 4A and 4B) and ferrocyanide (FIGS. 4C and 4D) cyclic voltammograms. Four repetitive stretchings in the horizontal direction (with a strain of 1.53) were carried out for assessing the influence of such mechanical stress. No apparent change in the background voltammograms is observed after such repetitive stretching of both textile-based electrodes (FIGS. 4A and 4B), indicating minimal change in the effective surface area. In contrast, the ferrocyanide oxidation peak currents and the anodic peak potentials of both electrodes decrease following their first stretching (FIGS. 4C and 4D). While the peak current of the MERONA-based electrodes remains stable upon successive stretching, the signal of the COVINGTON sensor decreases gradually between the 2nd and 4th stretching. No further change in the peak potentials is observed upon repetitive stretching. Overall, the cyclic voltammetric data of FIGS. 3A, 3B, 3C, and 3D and FIGS. 4A, 4B, 4C, and 4D indicate a favorable voltammetric response at both textile-based printed electrodes which is slightly affected by mechanical stress associated with the clothing deformation.

Optical imaging indicated no apparent bending—induced changes in the surface adhesion, electrode edges or the appearance of defects or cracks of both underwear-based carbon electrodes. The repetitive stretching action, in contrast, resulted in minimal degradation of the surface of the MERONA based sensor, and a more profound damage of the surface of the COVINGTON-based electrode. These changes are indicated also from measurements of the electrode resistance, which increased from 200 ohms to 5 and 20 kohms upon 3 repetitive stretching of the MERONA and COVINGTON electrodes, respectively. Such observations are in agreement with the voltammetric data of FIGS. 4A, 4B, 4C, and 4D. The MERONA substrate offered also higher reproducibility and was thus used for all subsequent analytical work.

Figures 5A, 5B, 5C:
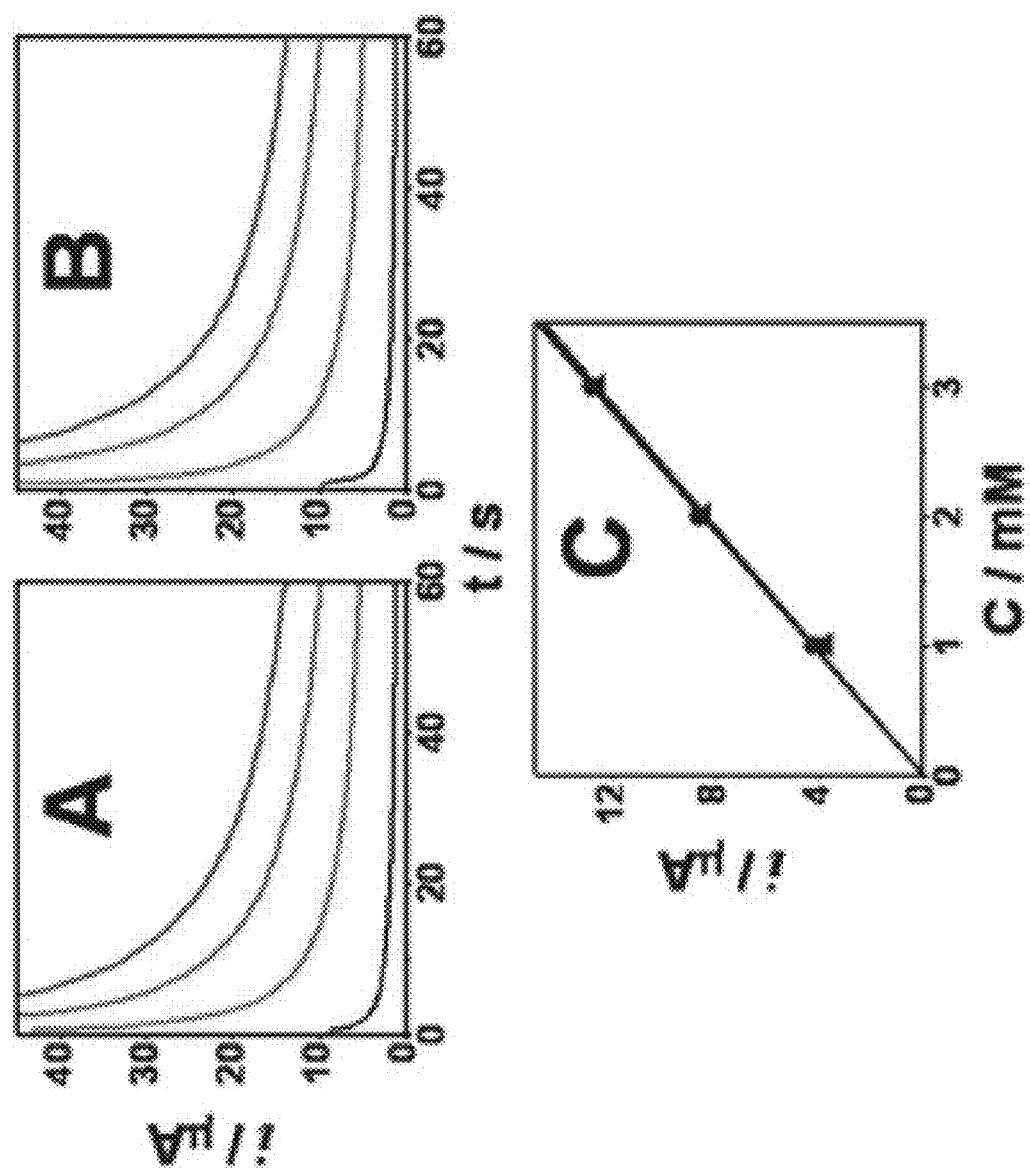

Chronoamperometric experiments, commonly used for enzyme-based electrochemical sensing, were subsequently carried out in connection to relevant compounds (NADH or hydrogen peroxide—which are the detectable products of numerous biocatalytic reactions—as well as potassium ferrocyanide as a common redox marker and mediator). The influence of stretching-induced mechanical stress upon the chronoamperometric response of ferrocyanide and hydrogen peroxide is examined in FIGS. 5A-F. FIGS. 5A, 5B, 5D, and 5E show chronoamperometric response of the MERONA-based electrodes to ferrocyanide (FIGS. 5A and 5B) and hydrogen peroxide (FIGS. 5D and 5E) solutions before (FIGS. 5A and 5D) and after 2 stretching steps (FIGS. 5B and 5E). FIGS. 5C and 5F show corresponding calibration plots before stretching (square), and after the first (cycle) second (triangle) stretching. The stretching time is 5 s. The release time is 10 s. The average strain is 1.53. The response for increasing ferrocyanide concentrations (1-3 mM) was not affected by two stretching steps (FIG. 5A vs. FIG. 5B). Identical calibration plots are thus observed in FIG. 5C. In contrast, the response for hydrogen peroxide (5-25 mM) increases dramatically following such stretching (FIG. 5D vs. FIG. 5E). Such stretching-induced signal enhancement results also in defined calibration plots (FIG. 5F). The sensitivity increases from 0.176 $\mu AmM^{-1}$ (before the stretch) to 0.338 and 0.451 $\mu A.mM^{-1}$ (after the first and second stretches, respectively) (FIG. 5F). Based on the data of FIG. 5 it seems that stretching of the textile substrate increases the microstructure of the printed electrodes to enhance the mass transport of the small peroxide molecules (but not of the larger ferrocyanide species). Note that our early background CV response (FIG. 4A) indicates that such stretching has a negligible effect upon the surface area of the MERONA-based printed electrode. Notice also the small error bars in connection to 3 successive stretching.

Figures 6A, 6B, 6C, 6D:
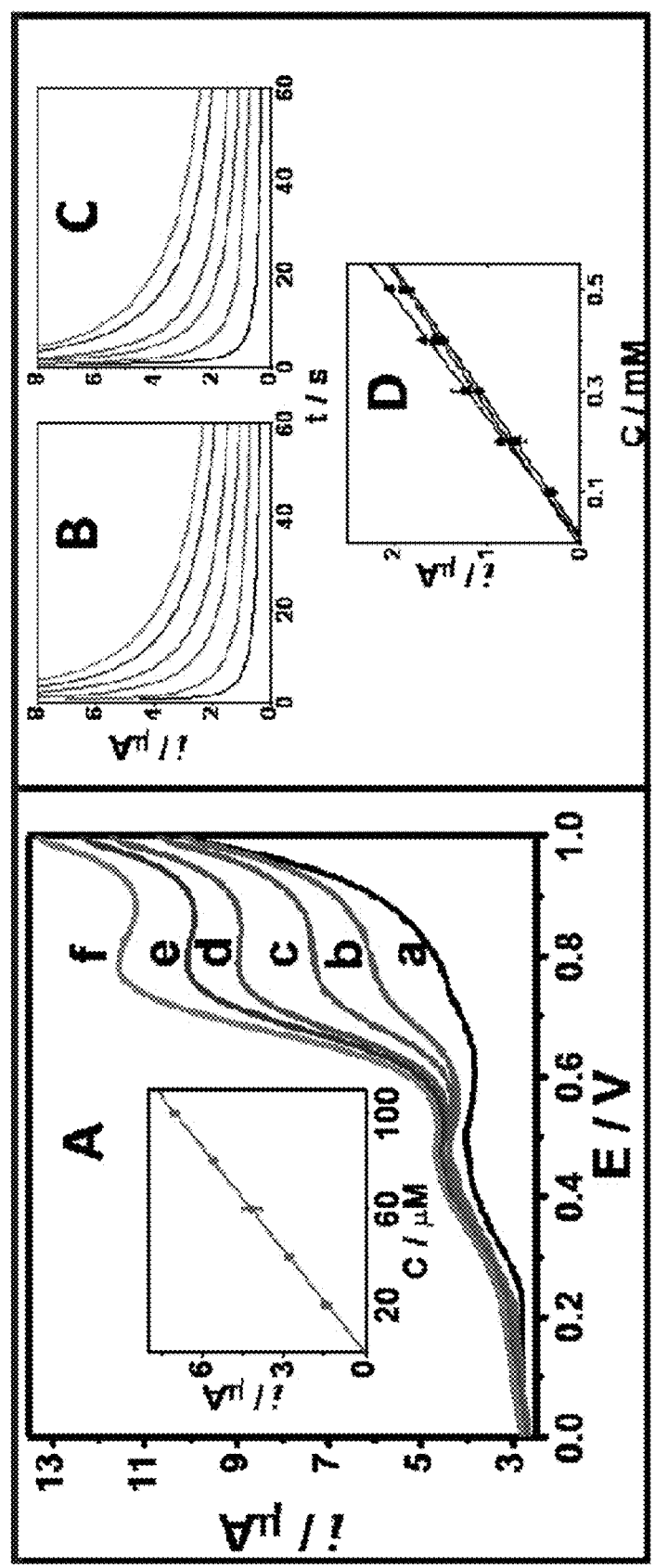
FIGS. 6A, 6B and 6C show.
FIG. 6D shows corresponding calibration curves associated to before stretching (square), and after the first (cycle) and the second (triangle) stretching steps. Scan rate, 0.1 V/s. Other conditions, as in FIGS. 3A-3D.

This textile-based screen-printed electrode was subsequently examined for voltammetric and amperometric detection of NADH. FIG. 6A shows linear scan voltammograms recorded at MERONA-based electrodes for increasing levels of NADH in 20 μM steps, along with the resulting calibration plot (inset). FIGS. 6B and 6C show chronoamperometric curves of increasing NADH concentrations (in 0.1 mM steps) of before (FIG. 6B) and after 2 stretching (FIG. 6C) steps. The stretching time is 5 s. The release time is 10 s. The strain is 1.53. FIG. 6D shows corresponding calibration curves associated to before stretching (square), and after the first (cycle) and the second (triangle) stretching steps. The scan rate is 0.1 V/s. Other conditions are as shown in FIG. 3. Thus, FIG. 6A displays linear scan voltammograms for NADH solutions of increasing concentrations in 20 μM steps over the 20-100 μM range (b-f). Well defined voltammetric peaks are observed for these micromolar NADH concentrations (Ep=0.80V), along with a low background current (a). Such voltammograms result in a well-defined linear calibration plot (shown in the inset), with a sensitivity of 0.07 μA.μM-1. We also evaluated the influence of the mechanical stress of the printed textile electrodes upon the NADH response. FIGS. 6B and 6C compare chronoamperograms for increasing NADH concentrations (100-500 μM) before and after, respectively, stretching of the textile electrodes. Similar to the ferrocyanide signals of FIGS. 5A and 5B, the stretching has a minimal effect upon the NADH response (FIG. 6B vs. 6C) and upon the overall sensitivity (FIG. 6D). These data support again that the stretching action influences primarily the mass transport of small molecules (e.g., hydrogen peroxide). Notice also (from the error bars) the high reproducibility of these data; these correspond to relative standard deviations ranging from 0.5 to 9.5%. Overall, the present textile-based printed electrode demonstrates convenient electrochemical measurements of 0-3 mM ferrocyanide, 0-25 mM H2O2, and low concentration of NADH (0-100 μM). Such attractive behavior indicates great promise for a wide range of biosensing applications in connection to the incorporation of an appropriate enzymatic layer.

Applications

We have illustrated the direct screen printing of amperometric carbon sensors onto clothing and the favorable electrochemical behavior of such textile-based sensors. Convenient measurements of hydrogen peroxide and NADH have been documented. Mechanical stress studies, relevant to the wearer daily activity, have indicated that textile-based printed sensors survive large deformations. Both bending and stretching of the textile substrate have minimal detrimental effect upon the electrochemical measurements, and in some instances (e.g., for measurements of hydrogen peroxide) even lead to enhanced signals. The overall electrochemical behavior is influenced by the physical characteristics of the textile substrate. Specific future applications would thus require tailoring of the printing protocol and ink formulation and viscosity for the specific substrate material. Since the performance of textile-based electrochemical sensors is directly related to the printing quality, it is useful that the printing protocol and ink formulation be tailored for the specific substrate material. Such tailoring would require a better understanding of the compatibility of different textiles with various conducting inks and of their correlation to the mechanical and electrical properties of the resulting electrodes, and should lead to the identification of the more favorable textile-ink combination. The nature and comfort of the elastic-band based sensors, and their tight contact with the skin, should be particularly attractive for direct sweat monitoring. Future efforts in this direction will also include the incorporation of chemically selective layer (e.g., permselective coating or enzyme layer) and assessment of the role of the clothing deformation upon the performance and stability of such layer towards textile-based healthcare and soldier monitoring systems. Particularly attractive will be dehydrogenase and oxidase based enzyme sensors for ethanol and lactate, respectively, in connection to monitoring alcohol consumption in drivers or performance/stress of soldiers/athletes. Unlike glucose sweat levels, the concentration of alcohol or lactate in sweat has a significant clinical relevance. The large surface area of clothing could be used for integrating the necessary supporting electronic, display, power and communication functions (without external devices) and hence for communicating relevant health parameters. While clothing-integrated electrochemical sensors hold considerable promise for future healthcare, military or sport applications, such non-invasive textile-based sensing requires proper attention to key challenges of sample delivery to the electrode surface and of sensor calibration and interconnection.

Figure 7A:
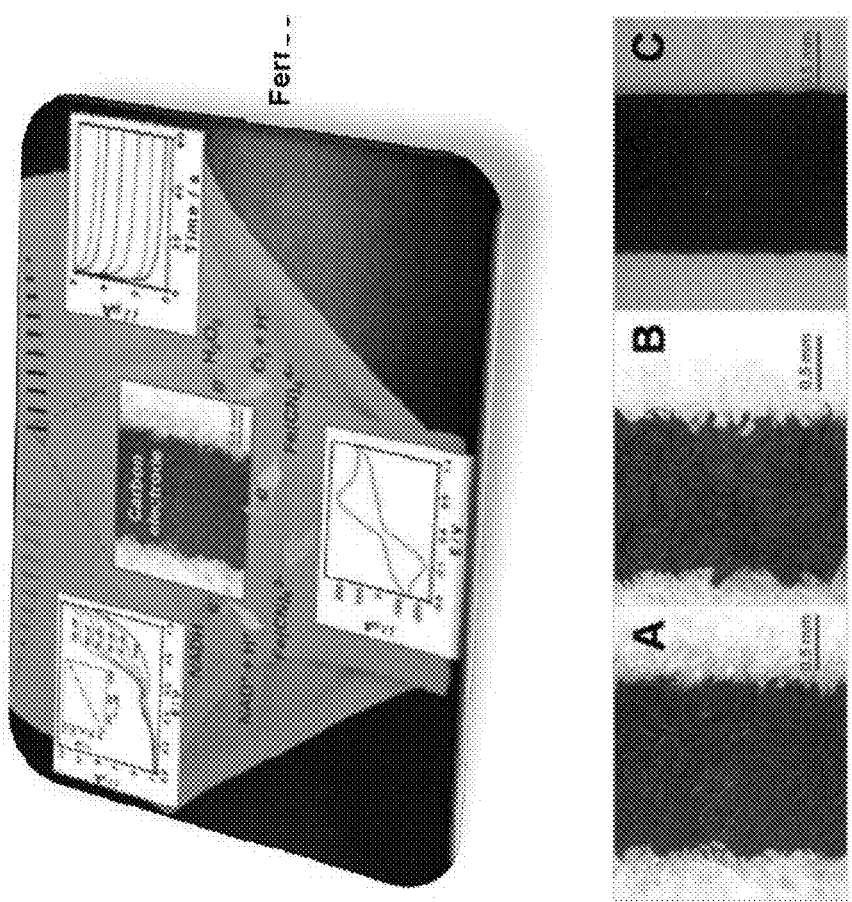
FIG. 7A shows exemplary screen-printed carbon sensors on underwear.
Figure 7B:
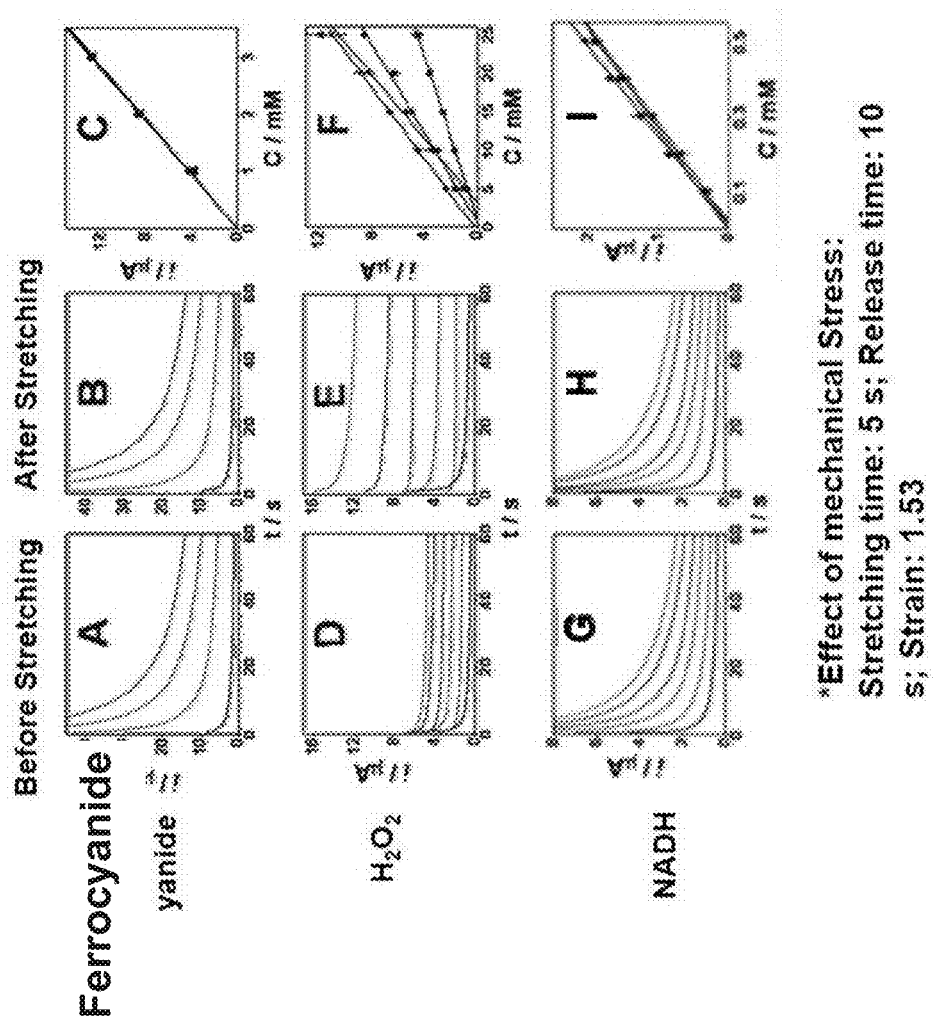
FIG. 7B shows an exemplary effect of mechanical stress.

FIG. 7A shows exemplary screen-printed carbon sensors on underwear. FIG. 7B shows an exemplary effect of mechanical stress.

FIG. 8 shows an example of sensors screen-printed on a Gor-Tex (GORE-TEX®) based fabric.

Figure 9A:
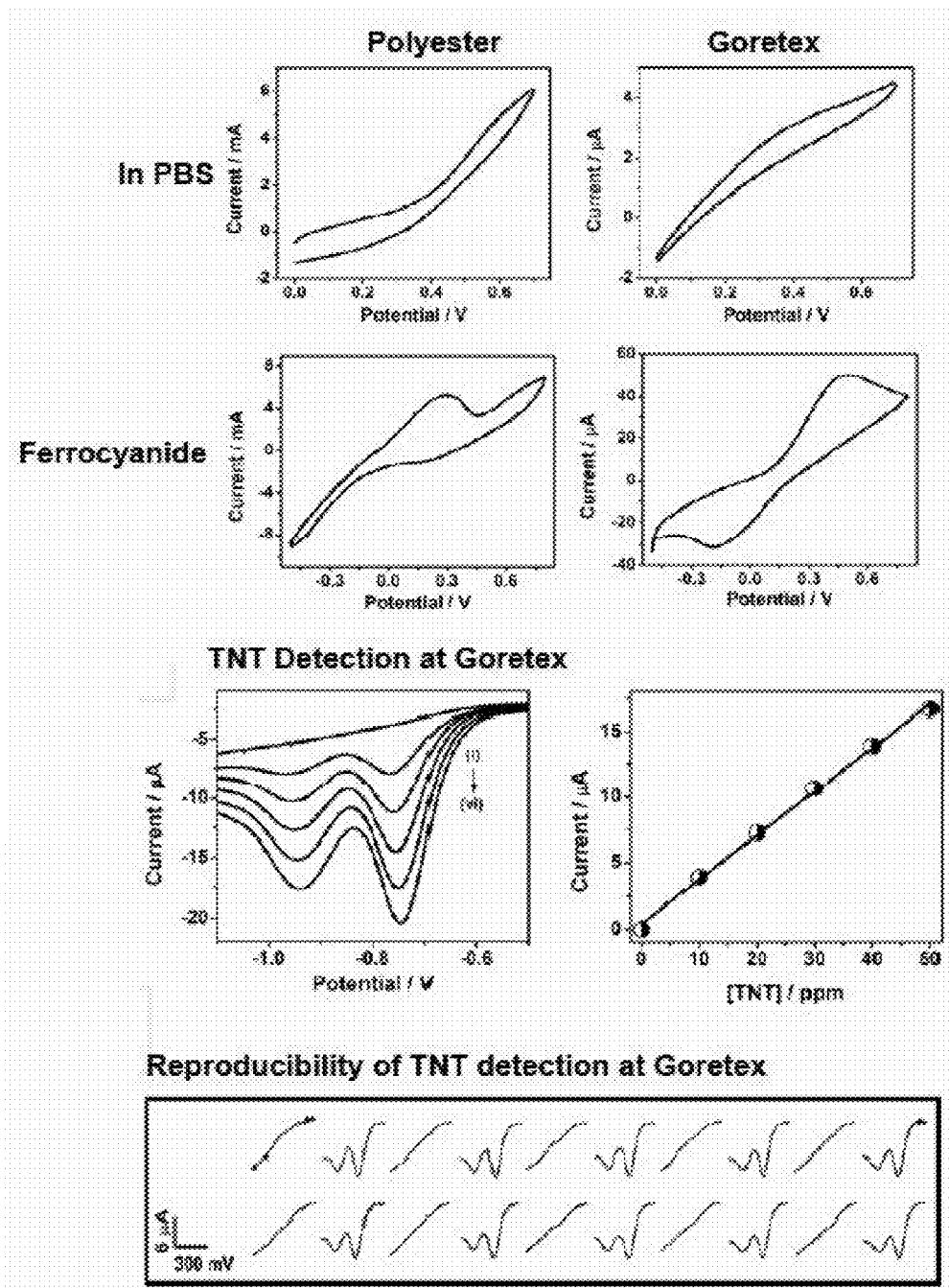
FIGS. 9A and 9B show data associated with screen-printed sensors on polyester and Gore-Tex, including an effect of bending on the electrocatalytic activity.
Figure 9B:
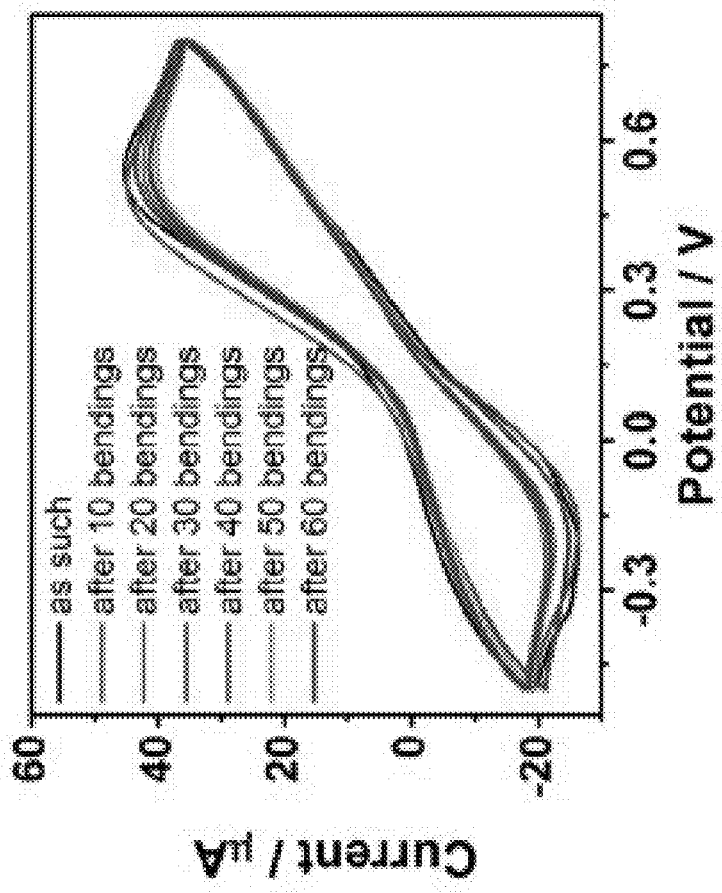

FIGS. 9A and 9B show data associated with screen-printed sensors on polyester and Gor-Tex, including an effect of bending on the electrocatalytic activity.

Figure 10:
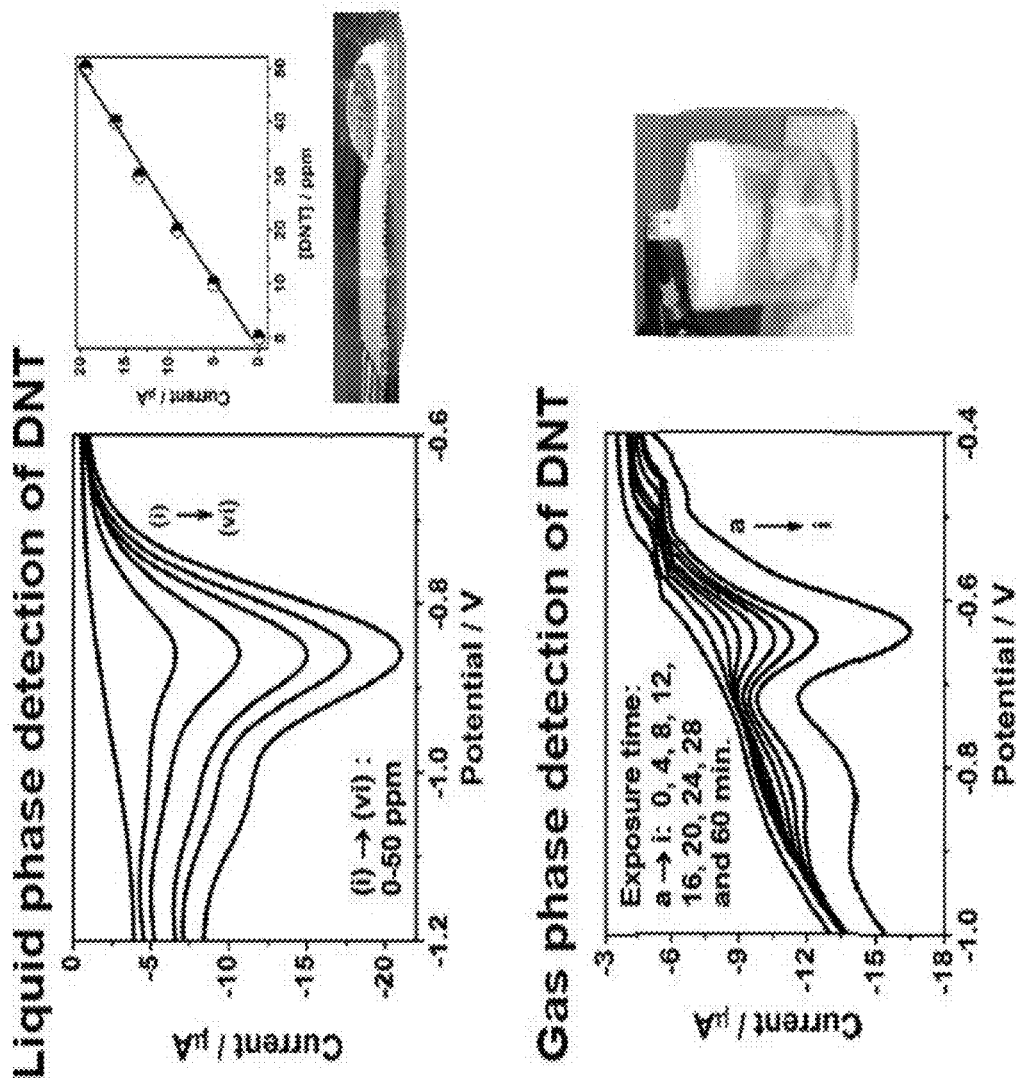
FIG. 10 shows liquid phase detection of DNT and gas phase detection of DNT using screen-printed sensors.

FIG. 10 shows liquid phase detection of dinitrotoluene DNT and gas phase detection of DNT using screen-printed sensors.

With reference to at least FIGS. 11A, 11B, 12A, 12B, 13A, 13B, 13C, 14, 15A, 15B, 16A, 16B, and 17, certain devices and techniques are disclosed below.

For some disclosed techniques, potassium ferrocyanide and acetonitrile were obtained from Fisher Scientific (Fair Lawn, N.J.) and used without further purification. Potassium phosphate (both monobasic and dibasic), 2,4-dinitrotoluene (DNT), potassium chloride, and agarose I-A were purchased from Sigma-Aldrich (St. Louis, Mo.). 2,4,6-trinitrotoluene (TNT) solution (1000 μg/mL in acetonitrile) was obtained from Cerilliant, Round Rock, Tex. Deionized water (>18 MΩ-cm) from a NANOpure Diamond system (Thermo Scientific Barnstead, Waltham, Mass.) was used to prepare all solutions. 50 mM potassium phosphate buffer (pH 7.4) was employed in all the electrochemical measurements. GORE-TEX (registered trademark of W. L. Gore & Associates, Inc., Flagstaff, Ariz.) fabric (3-ply Nylon woodland camouflage) was purchased from Rockywoods (Loveland, Colo.). 100% Polyester and 100% cotton fabrics were cut from garments that were purchased from the local department store.

Preparation of Sensing Electrodes

Figures 11A, 11B:
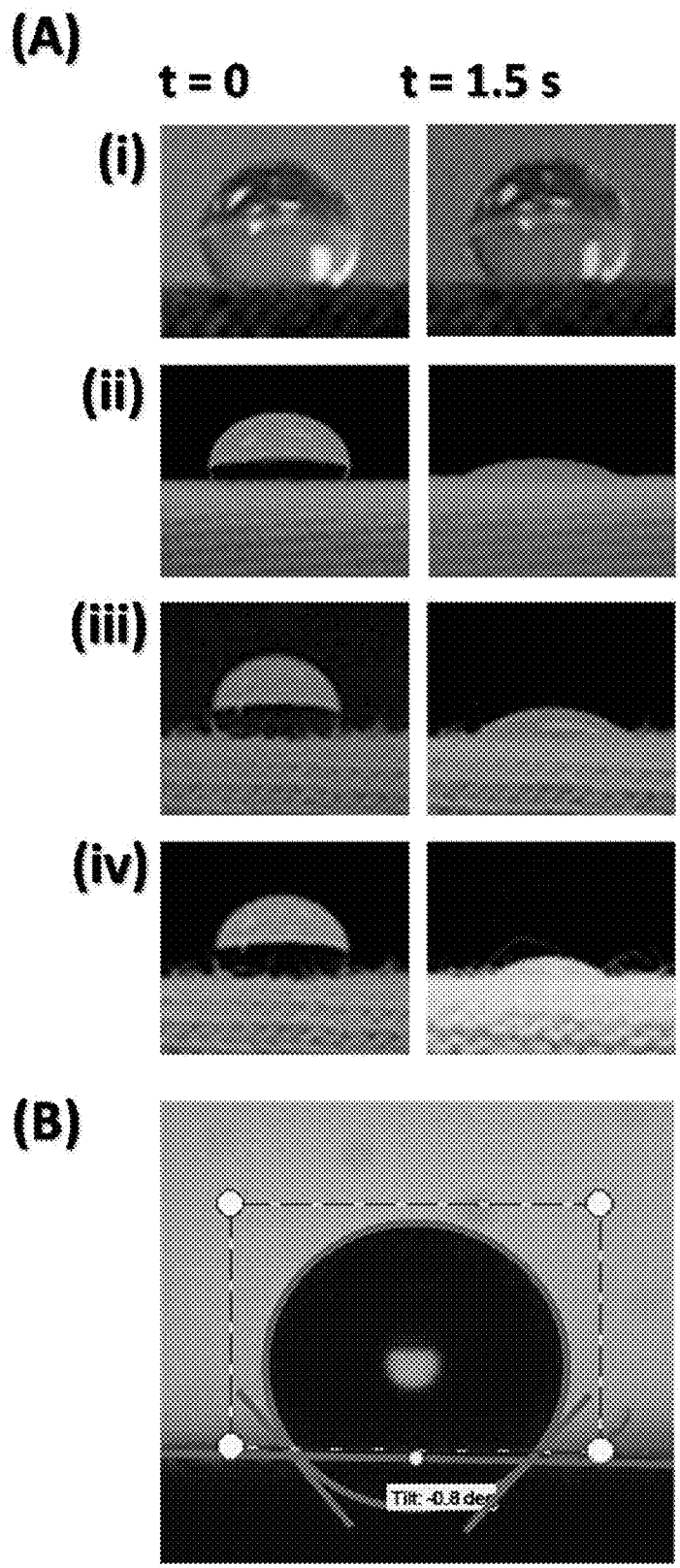
FIG. 11A shows dynamic optical contact angle measurements performed at t=0 s (left) and t=1.5 (right) on (i) GORE-TEX, (ii) 100% polyester, (iii) 100% cotton, and (iv) 35% cotton+65% polyester fabrics.
FIG. 11B shows static contact angle measurement performed on GORE-TEX fabric.

Fabrics were pre-heated at 130° C. for 1 hr before the printing process. A semi-automatic screen-printer (Model TF 100, MPM, Franklin, Mass.) was employed to deposit a silver/silver chloride ink (E2414, Ercon, Wareham, Mass.) and carbon ink (E3449, Ercon, Wareham, Mass.) through a patterned stencil that formed the conductive traces and sensing electrodes, respectively. Blue insulating ink (E6165, Ercon, Wareham, Mass.) was subsequently printed to define the electroactive area of the electrodes. Afterward, the patterned electrode was cured at 125° C. for 30 min, thereby forming the fabric-based sensing electrodes. All tests and electrochemical measurements were performed after cutting the fabric into 10×34 mm strips containing the three-electrode set. A magnified image of a typical GORE-TEX® fabric-based sensor is shown in the right of FIG. 11A.

For the preparation of the fabric-based sensor employed in the vapor-phase detection investigation, a polyester film coated with pressure-sensitive adhesive (ARcare 8259, Adhesives Research, Inc., Glen Rock, Pa.) with a 7 mm diameter opening was applied on the surface of the GORE-TEX® fabric-based sensor (fabrication outlined above) to create a cavity for casting the solid electrolyte. A hydrogel electrolyte was prepared by dissolving 100 mg agarose into 5 ml 0.5 M potassium chloride solution under stirring. The mixture was then brought to a boil (around 200° C.) and remained at this temperature for 5-10 minutes under continuous stirring until the agarose dissolved completely. Subsequently, the gel solution was cooled to 65° C. and kept at this temperature (with stirring applied) for the further use. The solid electrolyte of the sensor was casted by dipping the fabric-based sensor into the agarose solution and promptly removing the sensor, allowing the agarose to solidify on the electrode surface at room temperature.

Apparatus and Measurements

All electrochemical measurements were performed at room temperature using a CH Instruments 1232A Electrochemical Analyzer (Austin, Tex.). For the liquid-phase measurements, a 60 µL sample was deposited on the surface of the electrodes. Both cyclic voltammetry (CV) and square-wave voltammetry (SWV) were used to evaluate the performance of the fabric-based sensors with the experimental parameters indicated in the individual figures. To investigate the wetting properties of the fabrics under study, the CV recording was initiated immediately upon the application of sample drop onto the electrode surface. The five initial cycles of the CV were sampled for comparison. The steady-state CV was also recorded until the traces roughly overlapped for two consecutive cycles. Gas-phase measurements were performed by inserting the GORE-TEX® fabric-based sensor into a 30 mL glass jar containing 60 mg DNT powder for 30 min. SWVs were sampled successively with increasing exposure time (namely the time period after the sensor's insertion into the jar containing DNT).

To understand the effect of bending upon the electrochemical/sensing abilities of the electrode, the bending operation was performed by the same individual and only applied on the electroactive section of electrodes. Each bending experiment consisted of the application of an inward 180° bend with a 1 mm bend radius for 1 s. Multiple bending was separated with 1 sec release intervals. The morphology of the fabric-based sensor was examined using a field emission scanning electron microscope (Philips XL30, Amsterdam, and The Netherlands). All specimens were coated with chromium prior to analysis using a sputtering instrument (Energy Beam Sciences Emitech K575X, East Granby, Conn.). A charging current of 130 mA was applied for 30 s to deposit ~15 nm of chromium on the sample surface. Contact angle measurements were performed using Goniometers (CAM 100) from KSV Instruments Ltd.

Results and Discussion

Screen-printing technology has previously been leveraged to fabricate electrochemical electrodes on the elastic waistband of undergarments, in connection with the detection of several bio-electroactive substances such as hydrogen peroxide ($H2O2$) and reduced β-Nicotinamide adenine dinucleotide (NADH). Although such electrodes exhibited satisfactory mechanical properties and adhesion to the textile substrate, the textile absorbed the sample solution entirely due to its hydrophilic nature, which is anticipated to deteriorate the sensing ability of the sensor over time. A fabric possessing a densely-woven structure or, alternatively, water-repellant properties, would serve as an excellent candidate for use as the substrate to enable robust operation.

We evaluated two varieties of widely-available fabric materials, 100% polyester, 100% cotton, and GORE-TEX, a completely waterproof and breathable fabric intended for outerwear. The hydrophobility/hydrophobicity of each fabric was evaluated by a contact angle measurement, performed in air. FIG. 11A compares images captured in real-time contact angle measurements on (i) GORE-TEX, (ii) 100% polyester, (iii) 100% cotton, and (iv) 35% cotton+65% polyester at 0 (left) and 1.5 s (right) following the deposition of the droplet on the fabric's surface. From an inspection of the contact angle measurement shown in FIG. 11B, the GORE-TEX fabric exhibited the greatest hydrophobicity among all the textiles under study with a 130° contact angle, thereby demonstrating its super-hydrophobic properties. At an elapsed time of 1.5 s, the GORE-TEX surface did not wet, whereas the droplets were almost entirely absorbed by the other three fabrics: 100% polyester, 100% cotton, and 35% cotton+65% polyester blend. It is important to note that the resistance to wetting observed on the GORE-TEX fabric corresponds to the waterproof property claimed by the manufacturer. As the wetting rate exhibited by the other three fabrics was quite rapid (more than 80% of the sample volume was absorbed within 1.5 s), the effect of this absorption upon the electrochemical behavior required further evaluation.

Figures 12A, 12B:
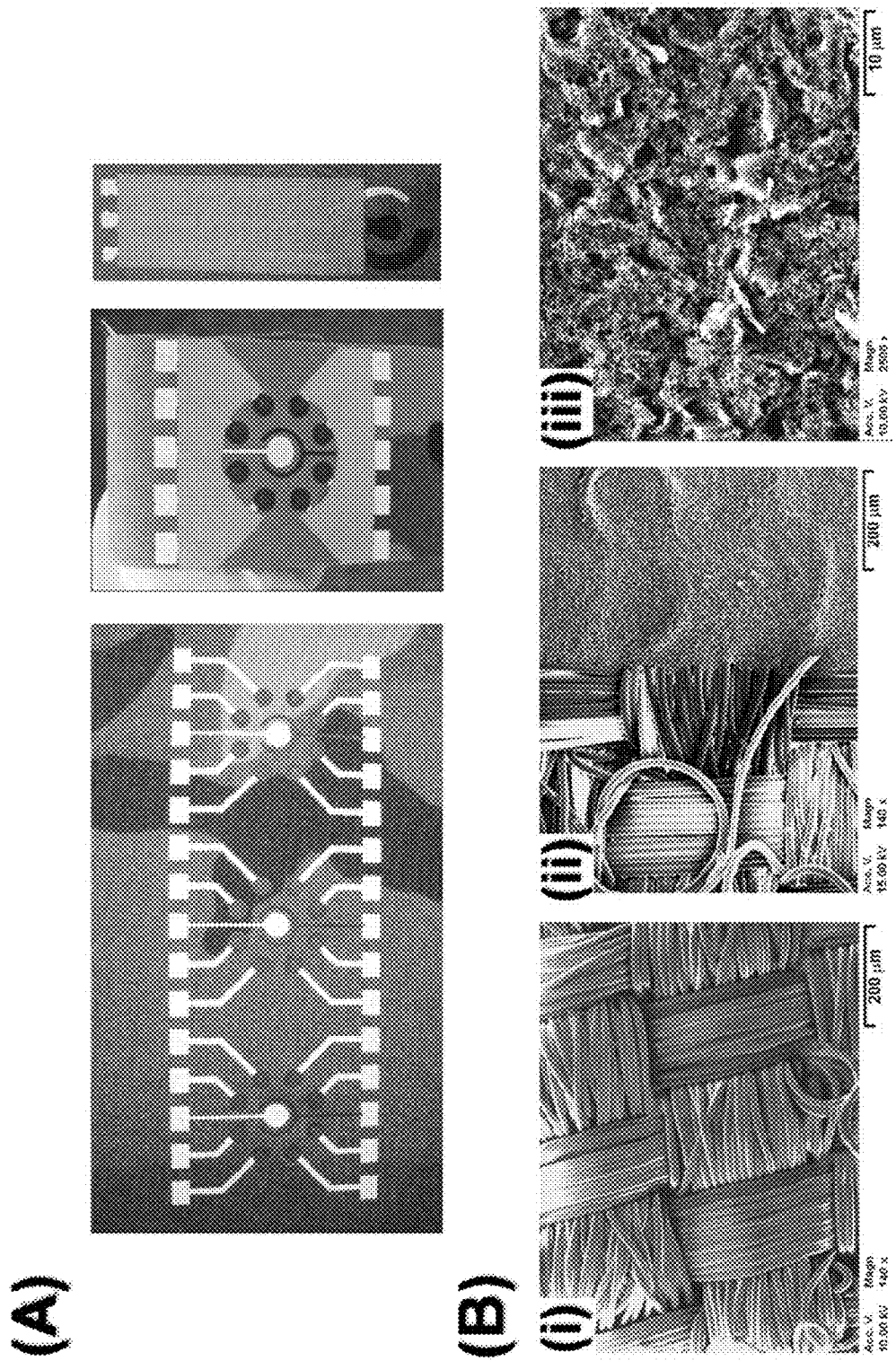
FIG. 12A shows optical images of various sensor patterns printed on the GORE-TEX fabric. (Left) Integrated eight-electrode sensing device with silver conductive traces and carbon electrode; (Middle) further insulated by blue insulating ink; (Right) single unit of three-electrode sensing device.
FIG. 12B shows SEM images of (i) top view of GORE-TEX fabric, (ii) printed carbon electrode on GORE-TEX fabric and (iii) magnified portion of carbon electrode.

The GORE-TEX fabric-based sensor is depicted in FIG. 12A. FIG. 12A (left) shows an array of sensors, each of which possesses eight carbon sensing electrodes, as well as one counter (carbon) electrode and one reference (Ag/AgCl) electrode. Each sensor was insulated by printing an insulting ink around the active electrode area, thereby forming the complete GORE-TEX fabric-based electrode array (FIG. 12A middle). In addition, a three-electrode design is patterned on the GORE-TEX substrate (FIG. 12A right), which is used for the remainder of this study. Micrographs of the surface morphology, the boundary of the printed carbon electrode, and a close-up of the carbon electrode surface on the GORE-TEX substrate are shown in FIG. 12B (i, ii, and iii), respectively. FIG. 12B(i) depicts the woven nylon protective layer employed in typical GORE-TEX fabric. Note that the carbon electrode printed on the woven nylon fabric possessed a well-defined boundary as opposed to printed electrodes on other fabrics where the fiber structure in the polyester and cotton fabrics are less organized that hampered the well-deposition of carbon electrode onto. A further magnified image of the carbon electrode is shown in FIG. 12B(iii) and illustrates the surface morphology in greater detail.

Figures 13A, 13B, 13C:
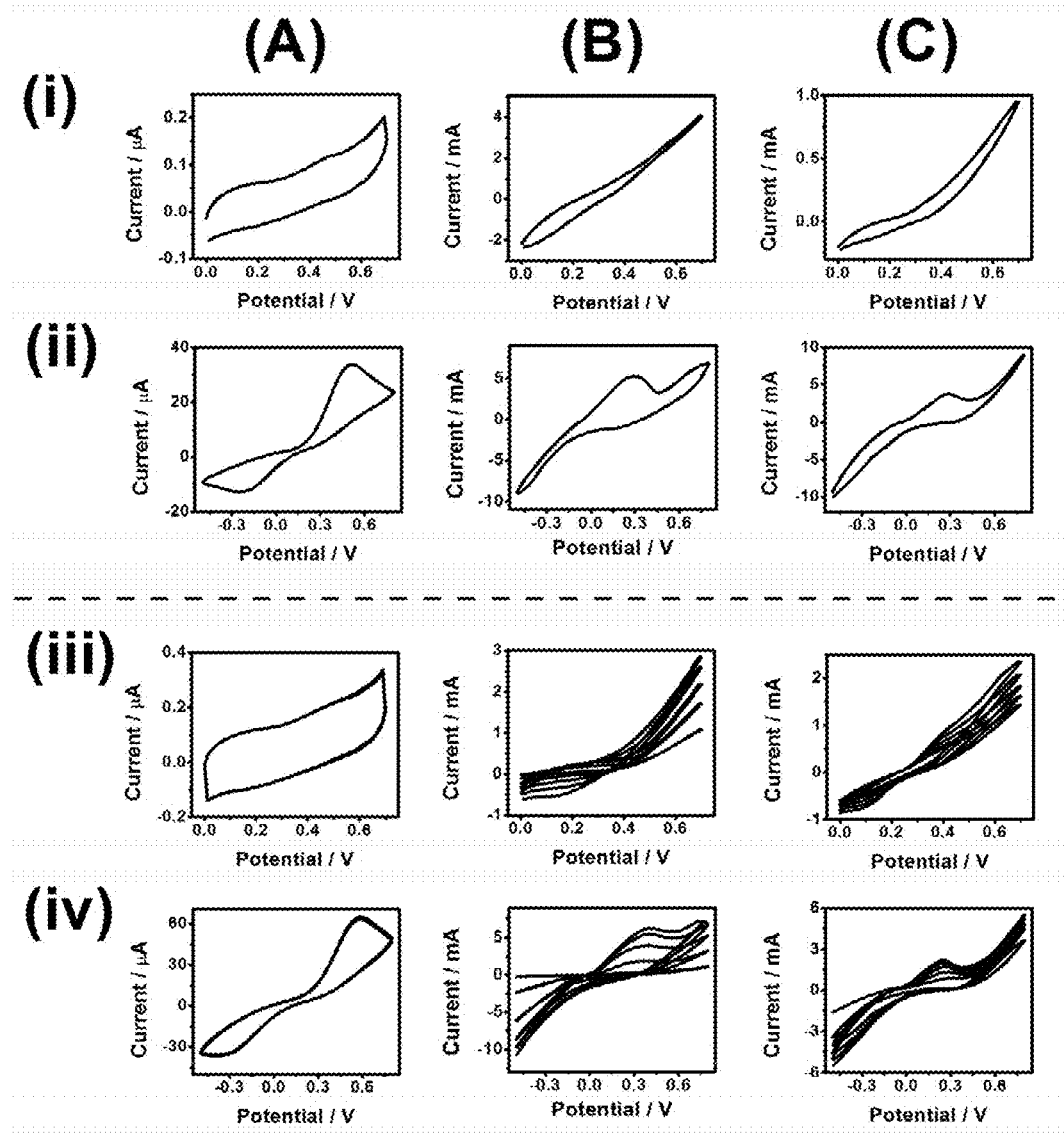
FIGS. 13A, 13B and 13C show cyclic voltammograms of various fabrics-based sensing devices in steady state (i, ii) and five initial scanning cycles (iii, iv) in (i, iii) 50 mM phosphate buffer (pH 7.4) and (ii, iv) 10 mM potassium ferrocyanide.

To further characterize the effect of wetting upon the electrochemical sensing performance, cyclic voltrammetry was performed using various fabric-based electrodes. FIGS. 13A, 13B and 13C show the dynamic and steady-state cyclic voltammograms (CVs) recorded using the GORE-TEX (A), 100% polyester (B), and 100% cotton (C) fabric-based electrodes in both phosphate buffer (i and iii) and 10 mM potassium ferrocyanide solution (ii and iv). To examine the dynamic transition of wetting condition, CV experiments were conducted with a relatively high scan rate (300 mV/s) (iii and iv). With respect to the background measurements (phosphate buffer), the GORE-TEX fabric-based electrode exhibited minimal deviation among scanning cycles. As the number of scanning cycles increased, a significant increase in the recorded current was observed for both the 100% polyester and 100% cotton fabric-based electrodes (particularly at potentials greater than 0.4 V). This can be ascribed to an increase in the active electrode area owing to the wetting effect. The wetting transition is also confirmed by observation whereby the entire fabric-based electrode strip was eventually wetted by the sample solution. Similar behavior also occurred in the ferrocyanide solution (iv) where the GORE-TEX fabric-based electrode possesses consistent CVs between subsequent cycles. On the other hand, continually increasing current was observed in both 100% polyester and 100% cotton fabric-based electrodes over the duration of the experiment. It is key to note that the GORE-TEX fabric-based electrode yielded comparable redox properties as traditional carbon electrodes. However, only oxidation peaks at 0.4 and 0.24 V are recognizable in the 100% polyester and 100% cotton fabrics, respectively, whereas the reduction peaks are more obscure. Steady-state CVs were also obtained using these three varieties of fabric-based electrodes. As can be deduced from the figures, the results were in agreement with the redox behavior of the fabric-based electrodes discussed above, hence indicating the superior electrochemical properties of the GORE-TEX fabric-based electrode (FIG. 13A-ii).

Figure 14:
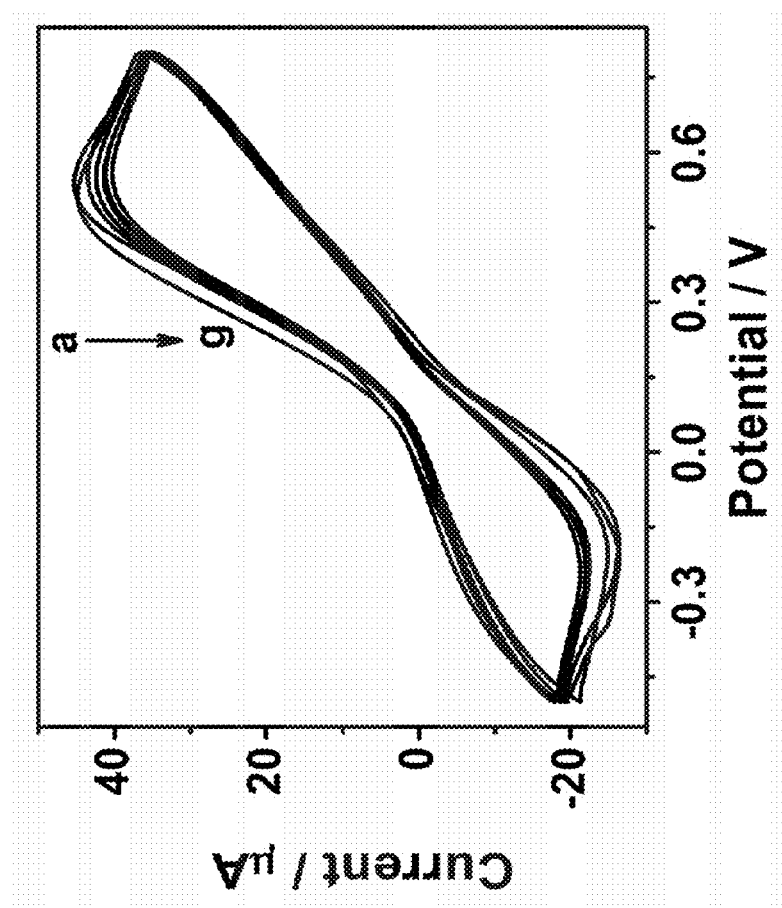
FIG. 14 shows effects of repetitive bending on the cyclic voltammograms of GORE-TEX fabric-based sensor in 10 mM potassium ferrocyanide. Ten bending operations were conducted between either two consecutive cyclic voltammetric experiments. Bending time, 1 s; release time, 1 s. Bending was applied at inward 180° with 1 mm bending radius. Scan rate=100 mV/s.

Although GORE-TEX-based textiles are known to be less stretchable and more robust than other fabrics, normal wear and upkeep may affect the microstructure and morphology of the GORE-TEX fabric-based sensor and hence its performance. The influence of such mechanical stress thus requires a detailed examination. The GORE-TEX fabric-based printed electrodes were thus subjected to successive bending operations and the influence of this mechanical stress upon the electrochemical performance was examined. Employing 10 mM potassium ferrocyanide as the analyte, cyclic voltammograms were recorded under repeated bending of the fabric substrate (increments of 10 bending operations up to 60). As can be seen in FIG. 14, repeated bending of the substrate did not modify the voltammetric response of the sensor.

Figures 15A, 15B:
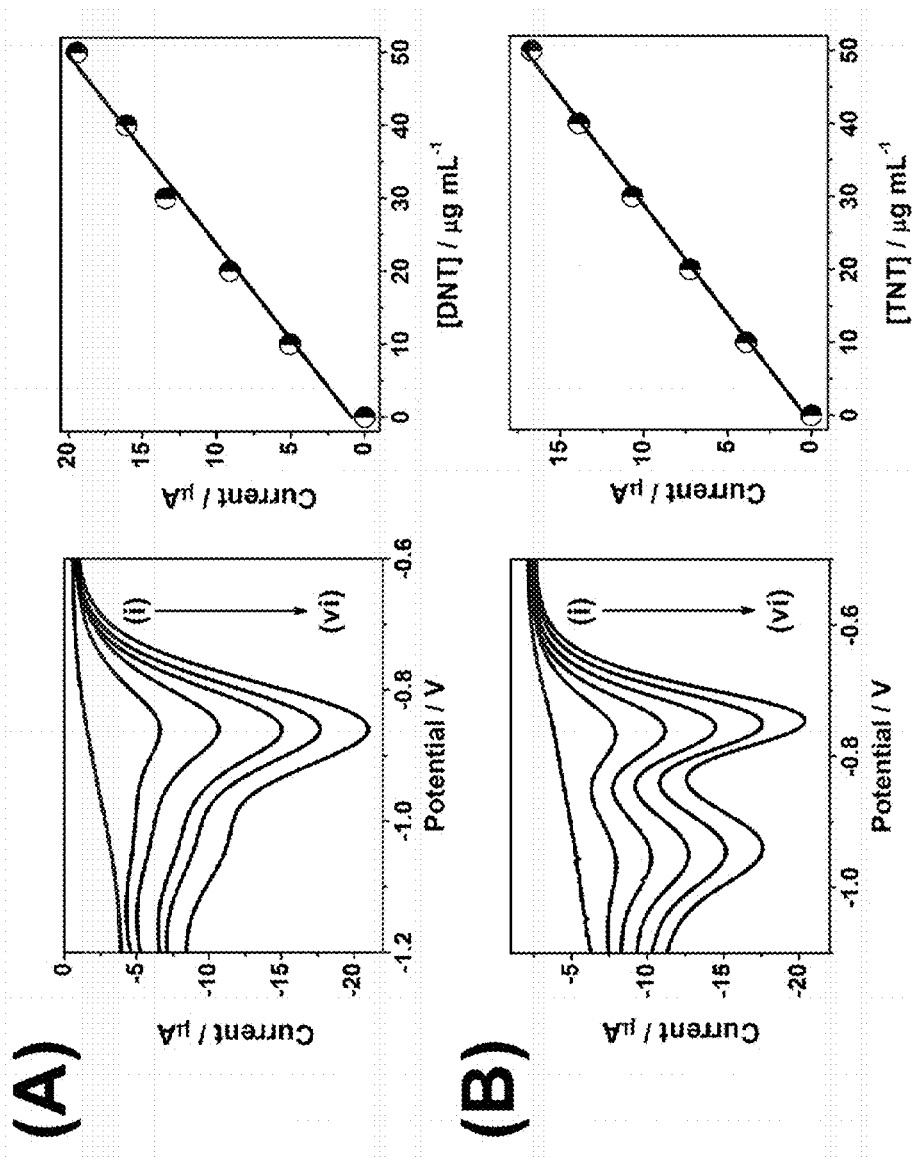
FIGS. 15A and 15B show Square Wave Voltammograms (left) of GORE-TEX fabric-based sensors to DNT.

Textile-based sensors that enable the sensitive detection of explosive agents are expected to be an effective and easily-deployable tool, particularly in security and military applications. In assessing the levels of DNT and TNT, the performance of the GORE-TEX fabric-based sensor was evaluated by employing a hypothetical analytical procedure that one could perform in the field (ie. placing a drop of a liquid under test on a fabric-based sensor). FIGS. 15A and 15B illustrate the square-wave voltammograms (SWVs) (potential step: 14 mV, pulse amplitude: 25 mV, pulse frequency: 20 Hz) of the GORE-TEX fabric-based sensors for DNT (FIG. 15A) and TNT (FIG. 15B) employing 0 to 50 µg/mL of analyte. In direct comparison with reported results in the literature, the GORE-TEX fabric-based sensor exhibited a well-defined peak at −0.86 V for DNT and two peaks (at −0.75 and −0.95 V) for TNT. These results indicate that the fabric-based electrodes possess comparable sensing abilities as conventional solid-state electrodes and printed electrodes on solid substrates. Calibration curves were plotted correlating the current signals at −0.86 (FIG. 15A) and −0.75 V (FIG. 15B) and demonstrate that exceptional linearity (given r-square higher than 0.99) can be obtained for the sensitive detection of DNT (0.38 µA. mL. µg-1) and TNT (0.33 µA. mL. µg-1).

Figures 16A, 16B:
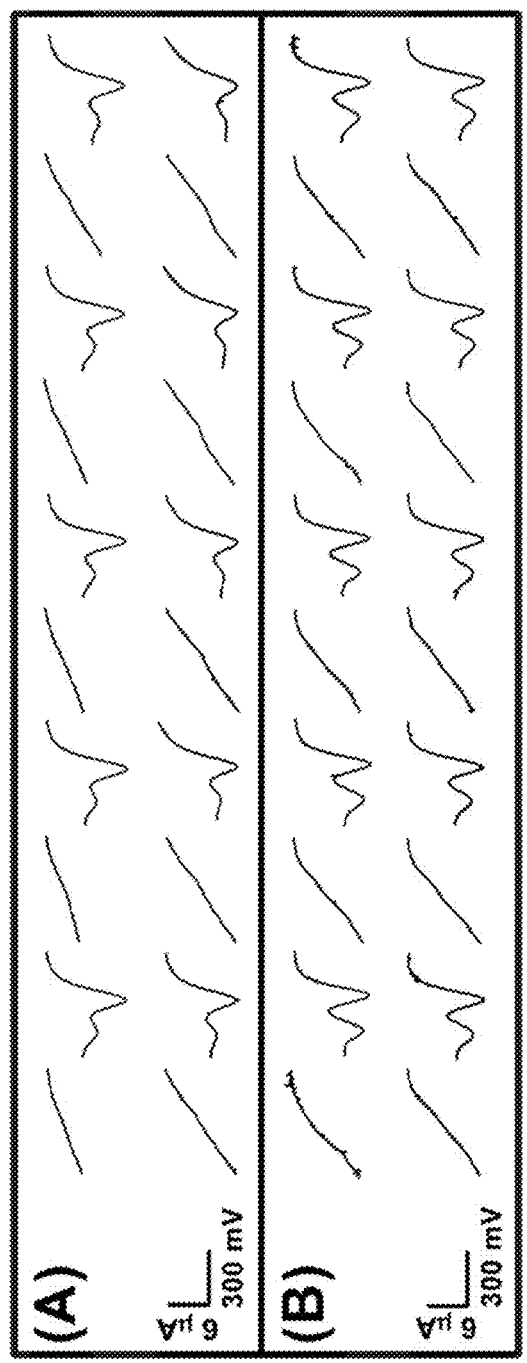
FIGS. 16A and 16B show response of the GORE-TEX fabric-based sensors to alternating blank/DNT (FIG. 16A) and blank/TNT (FIG. 16B) samples with analyte levels at 20 µg/mL using square wave voltammetry. Scanned potential: −0.6→−1.2 V (A) and −0.5→−1.1 V (FIG. 16B); SWV parameters, as in FIG. 15A. The surface was rinsed with the blank buffer solution following each explosive measurement.
Figure 17:
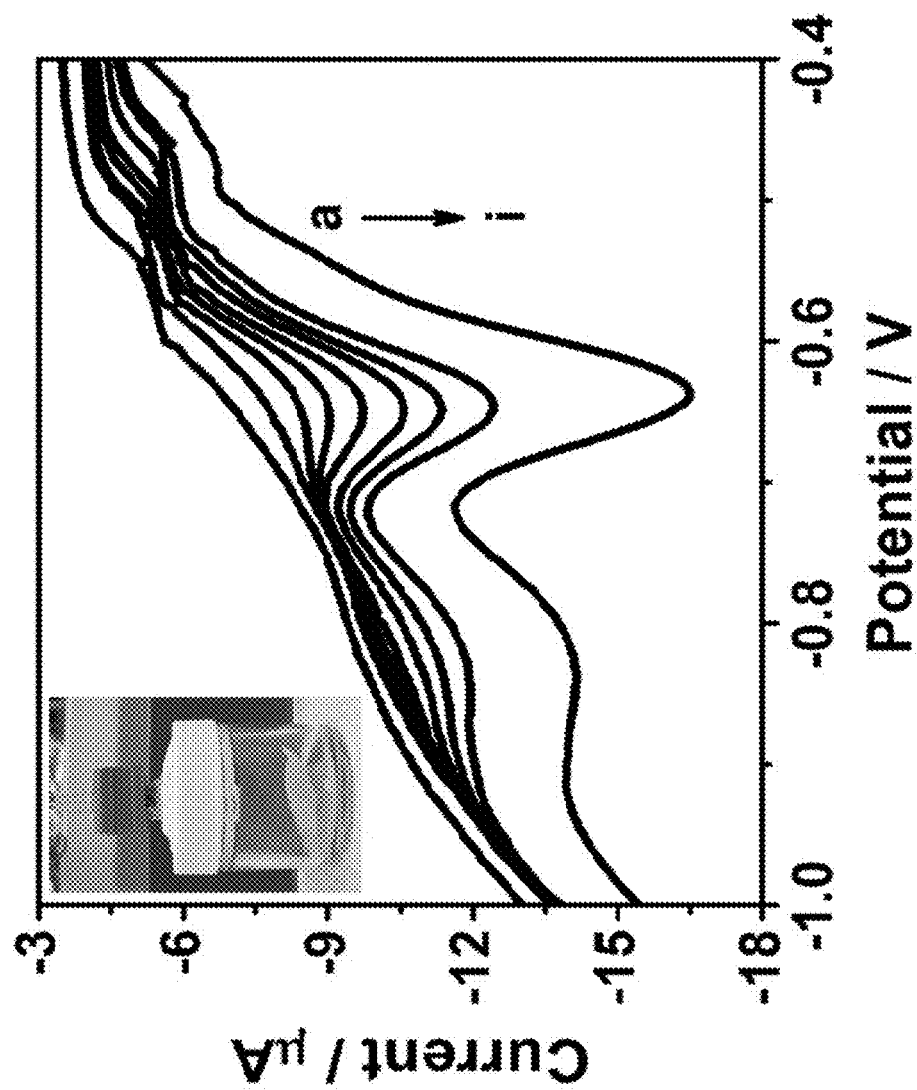
FIG. 17 shows vapor-phase detection of DNT using the GORE-TEX fabric-based sensors at various exposure durations after placing the analyte: a→i: 0, 4, 8, 12, 16, 20, 24, 28, and 60 min. Scanned potential, −0.4 to −1.0 V; SWV parameters, as in FIG. 15. Inset: Image for testing apparatus.

The repeatability of the GORE-TEX fabric-based sensor was subsequently examined. The investigation consisted of depositing 60 µL of 20 µg/mL DNT/TNT solution onto the GORE-TEX fabric-based sensor, recording the sensor's response, and then replacing the test sample with phosphate buffer and measuring its response in the same manner. This cycle was then repeated an additional nine iterations and the sensor response was recorded in each experiment for a scanned potential of −0.6 to 1.2 V (FIG. 15A) and −0.5 to 1.1V (FIG. 15B) for DNT and TNT, respectively. The SWV (potential step: 4 mV, pulse amplitude: 25 mV, pulse frequency: 20 Hz) results are shown in FIGS. 16A and 16B. This fabric-based sensor demonstrated well-defined response towards the detection of DNT and TNT, showing minimal decay in the 10th evaluation of DNT. These results indicate the potential of the GORE-TEX fabric-based sensor to detect explosives in a repetitive fashion. Unlike disposable electrode strips, the fabric-based sensor must be able to yield operation over extended periods with minimal deterioration of the sensor performance even under multiple sampling operations.

Gaseous detection of explosives is expected to meet the growing security demands for remote explosive sensing. The GORE-TEX fabric-based sensor was further modified with a hydrogel electrolyte in order to facilitate the detection of DNT vapor. DNT powder was stored in a sealed glass jar for 30 min to mimic a hypothetical situation where an explosive agent is concealed and transported within baggage. FIGS. 16A and 16B show the detection of DNT vapors using the GORE-TEX fabric-based sensor at increasing exposure durations using SWV (4 mV potential step scanned from −0.4 to −1.0 V, 25 mV pulse amplitude, 20 Hz pulse repetition frequency). As can be seen from the figures, the characteristic reduction peak at −0.63V vs Ag/AgCl increases as the exposure time increases from 0 to 60 min. As such, allowing proper exposure duration, the high-fidelity detection of DNT vapors was achieved using the printed GORE-TEX fabric-based electrodes.

Applications

We have illustrated the direct patterning of an electrochemical sensor onto various fabrics using conventional screen-printing methods. Moreover, we have characterized the electrochemical sensing properties of such textile-based printed electrodes and have demonstrated the robust and reliable detection of the explosive agents DNT and TNT using these devices. Cotton, polyester, and GORE-TEX fabrics were compared in order to determine a suitable textile substrate for the monitoring of chemical agents that a wearer in the field may be exposed to. Employing analytical and electrochemical techniques to characterize the performance of the various textile materials, the GORE-TEX fabric was determined to be an excellent substrate material for supporting screen-printed electrodes and was characterized by its high degree of hydrophobicity, minimal sample absorption, excellent printing quality, and preservation of electrochemical activity against repeated bending operations. Future efforts in this direction will also include the incorporation of the necessary supporting electronic devices, real-time information display, and alert functionality. Further assessment of the durability and reliability of the GORE-TEX substrate for extended periods of use will lead to the development of field-deployable security and soldier monitoring systems integrated into conventional garments.

The ability to detect in real time the presence of environmental contaminants and security threats within marine environments represents a major challenge to oceanographers, navies, local water-quality agencies and recreational surfers/divers throughout the globe. Conventional water quality analytical techniques mandate that the water sample be isolated and transported to the laboratory to undergo analysis, which is costly, labor-intensive and time-consuming. To this end, electrochemical devices have been developed that enable real-time monitoring of seawater towards potential hazards such as explosive residues or toxic metals. These devices include flow detectors for on-line shipboard monitoring and submersible sensors for remote detection. New hand-held analyzers have also been developed for underwater surveillance by divers. The latter, however, is not compatible with military or recreation activities (e.g., surfing, diving) that commonly require "hands-free" operations. A 'built-in' wearable sensor system that facilitates such marine operations while providing the user with a real-time assessment of their surroundings would thus be preferred.

Here we describe wearable electrochemical sensors on underwater garments comprised of the synthetic rubber neoprene. Neoprene, which was synthesized from chloroprene since 1931 by DuPont is a commonly used synthetic rubber for dry- and wetsuits. While dense neoprene seals the openings of diving suits, foamed neoprene serves as an exceptional thermal insulator that encapsulates most of the wearer's body. Its basic polymer, polychloroprene, is produced via emulsion polymerization before it is transferred into a foam-like material that consists of air bubbles and polymer arranged in a comb-like network. Neoprene can be tailored to the desired application, ranging from nylon overlays intended to increase wearer comfort, to varying degrees of thickness to compensate for pressure and temperature variance at greater diving depths and/or cooler waters. This, along with the elastic and superhydrophobic morphology of neoprene, makes underwater garments highly compatible with the thick-film (screen-printing) fabrication process and for sensing operation in marine environments. Thick-film microfabrication has been widely used for mass production of highly reproducible electrochemical sensors (e.g., glucose strips for diabetics). This process has recently been applied for printing electrochemical sensors on common textiles but not in connection to underwater garments. The integration of sensors directly onto underwater garments, such as those described in this paper, would provide the wearers with the ability to continuously assess their surroundings.

The potential of neoprene-based printed electrochemical electrodes as wearable sensors is demonstrated below for a wide range of marine monitoring scenarios. These results indicate the promise of such devices to allow the wearer (surfer/diver) to continuously assess their surroundings for potential contaminants or hazard without being preoccupied with the transport and operation of cumbersome analytical equipment. Following characterization of its surface morphology, the role of mechanical stress, and the redox activity towards ferricyanide, the analytical performance of the new neoprene-based electrochemical sensor was evaluated for trace voltammetric measurements of heavy metals such as copper and of nitroaromatic explosives such as 2,4,6-trinitrotoluene (TNT) in untreated seawater. In addition, the enzyme tyrosinase (Tyr) was incorporated within the sensor ink in order to facilitate the detection of phenolic pollutants in seawater. This represents the first example of electrochemical biosensing on textiles with printable enzyme containing inks. Subsequently, the new wearable biosensor was integrated with an encapsulated potentiostat capable of providing the wearer with a visual indication when the level of a target hazard or contaminant (e.g., phenols) has exceeded a pre-defined threshold. Under such operation, the wearer would be alerted to relocate to cleaner environments, in-line with water quality and related health standards for recreational divers and surfers. The concept can be extended to other important threat-assessment and environmental-monitoring applications in marine environments.

Materials and Methods

Preparation of Reagents

Tyrosinase from mushroom (Tyr, E.C. 1.14.18.1), Nafion (5% w/w solution), catechol, 4-chlorophenol, phenol, gold atomic absorption standard solution (1014 µg/mL Au in 5% HCl), copper atomic absorption standard solution (1000 µg/mL Cu in 2% HNO3), potassium chloride, potassium phosphate monobasic, and potassium phosphate dibasic were obtained from Sigma Aldrich (St. Louis, Mo.). Potassium ferricyanide was purchased from Fisher Scientific (Pittsburgh, Pa.) and the 2,4,6-trinitrotoluene (TNT) solution (1000 mg/mL in acetonitrile) was obtained from Cerilliant (Round Rock, Tex.). All compounds were used as supplied without further purification or modification. Ultrapure deionized water (18.2 MΩ·cm) was employed for the preparation of the reagents. All electrochemical measurements were conducted using seawater samples (pH ~8) collected from the shores of La Jolla, Calif.

Fabrication of the Screen-Printed Electrodes

A neoprene sheet (4 mm thickness) was purchased from Foamorder Inc. (San Francisco, Calif.) and cut to size (10 cm×10 cm) to enable the patterning of a set of 30 identical three-electrode sensors. Stencil patterns were custom-designed using AutoCAD (Autodesk Inc., San Rafael, Calif.) and outsourced for fabrication on stainless steel masks. A Speedline Technologies (Franklin, Mass.) screen printer (MPM-SPM model TF-100), was used to fabricate all layers of the sensor. An Ag/AgCl-based ink (E2414) from electrode patterns. Ercon Inc. (Wareham, Mass.) was employed to define the conductive underlayer as well as the reference electrode and printed directly onto the neoprene substrate. A carbon-based ink (Acheson E440B) from Henkel Corp. (Madison Heights, Mich.) was then overlaid on the conductor to define the working and counter electrode geometry. Finally, an insulator ink (Ercon E6165) was printed over the Ag/AgCl and carbon layers to insulate all except the contact pads and the upper segment of the electrodes. Subsequent to the printing process, the patterned substrate was cured in a temperature-controlled convection oven (SalvisLab Thermocenter) at 100° C. for 30 min and cut into 10 mm×34 mm test strips. Each printed three-electrode assembly consisted of a circular carbon working electrode (geometrical area: 3 mm2) inscribed in a hemispherical carbon counter electrode (area: 10 mm2) and a Ag/AgCl reference electrode (area: 2 mm2); e.g., FIGS. 18A and 18B.

For trace copper detection, the carbon working electrode of the SPE was modified via the electrodeposition of gold at an applied potential of 0.0 V vs Ag/AgCl for 20 min. The plating solution employed for these experiments consisted of a phosphate buffer, pH 7.0, containing 50 ppm gold.

Preparation of the biocatalytic layer of the Neoprene-based enzyme electrodes may be performed as follows. In order to quantify phenols, tyrosinase (Tyr) was mixed into the carbon ink (5% w/w) and the enzyme-containing ink was printed onto the surface of the working electrodes of cured SPEs. The amount of enzyme in the bioactive layer was approximately 200 U per electrode. After the printing process, the Tyr-ink layers were dried at room temperature for one hour. The electrodes were subsequently stored at 4° C. overnight. Following this procedure, 1 µL of aqueous Nafion solution (0.25% v/v) was dispensed on the working enzyme electrode. Finally, the electrodes were kept overnight at 4° C. prior to use.

Procedure

Measurements of phenolic compounds, TNT and copper were performed using chronamperometry, square-wave voltammetry and square-wave stripping voltammetry, respectively. Copper deposition was performed for 2 min at −1.0V vs Ag/AgCl under quiescent conditions, followed by a square-wave stripping voltammetric scan from −0.25 to 0.50 V, and a 2 min 'cleaning' at this final potential. Cyclic voltammetry (CV) was used for the initial characterization of the electrochemical behaviour.

Instrumentation

A CH Instruments (Austin, Tex.) Model 620 electrochemical analyzer was employed for all the electrochemical measurements. Voltammetric and chronoamperometric studies were performed to evaluate the electrochemical behavior of the neoprene SPEs. The morphology of the neoprene-based printed working electrode was examined using a field emission scanning electron microscope (SEM) (Philips XL30, Amsterdam, The Netherlands). All of the specimens were coated with chromium prior to SEM analysis using a sputtering instrument (Energy Beam Sciences Emitech K575X, East Granby, Conn.). A current of 130 mA was applied for 30 s to deposit ~10 nm of chromium on the sample surface. Contact angle measurements were performed with a precision goniometer (KSV CAM100, Helsinki, Finland). All experiments were performed in seawater at room temperature (T=22° C.).

A miniaturized 19 mm×19 mm PCB-mounted CMOS potentiostat containing a 3V Li-ion coin-cell battery was encapsulated in a watertight compartment and integrated into a wetsuit for water quality evaluation. In addition to the custom-designed three-electrode potentiostat, the PCB-mounted sensor was comprised of an integrator, voltage amplifier, adjustable comparator, digital logic, and LED-based readout and is described in further detail in the literature.19 The output potential of the potentiostat was established at −0.30 V (vs REF) and the device was operated in free-running chronoamperometric mode.

Results and discussion—Characterization of the morphology and polarity of the printable electrodes on the rubber substrate are as follows.

Figures 18A, 18B, 18C, 18D:
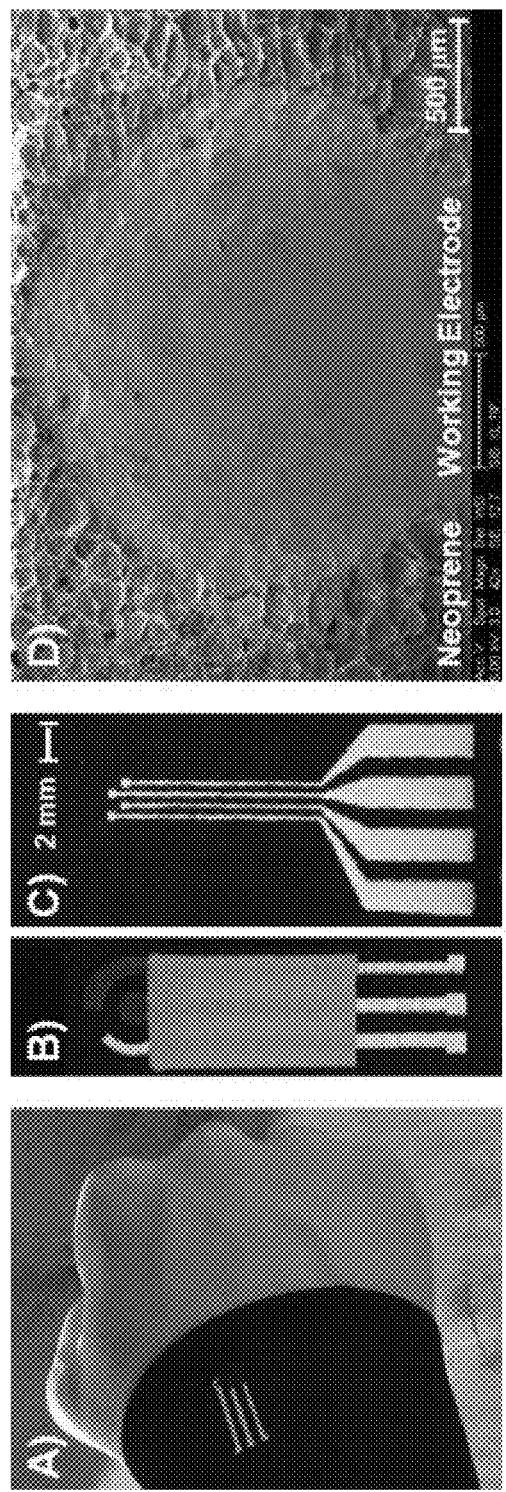
FIGS. 18A, 18B, 18C and 18D are as follows.

The use of the neoprene substrate offers high-resolution printing of electrochemical sensors, with smooth edges and no apparent defects. Various electrode configurations have been examined on various parts of commercially-available rubber wetsuits. For example, FIG. 18A displays a common three-electrode setup that was printed on the sleeve of such wetsuit. This configuration, comprising the carbon working and counter electrodes, along with an Ag/AgCl reference, was used throughout most of this study. A closer optical image of this printed electrode assembly, along with an insulating layer, is depicted in FIG. 18B.

As a detailed understanding of the physical properties of the substrate material is crucial for constructing high-fidelity wearable sensors, initial investigations were concerned with the characterization of the surface morphology and patterning resolution and quality of the printed electrodes. To this end, FIG. 18C shows a well-defined array of four electrodes printed with Ag/AgCl ink; the feature width of each contact line is ~195 μm, the pitch between adjacent electrodes is ~280 μm, and the diameter of the active area of each electrode is ~440 μm. Further insights into the surface morphology of the working electrode of the SPE on neoprene have been obtained from the SEM image (42× magnification) shown in FIG. 18D. The rubber area surrounding the working electrode consists of comb-like polymeric sub-units, which are characteristic of the neoprene substrate. The bare working electrode on neoprene exhibits an amorphous surface structure, defined by the micrometer-sized carbon flakes comprising the printed ink, along with defined boundaries. A similar morphology was observed for the carbon electrode printed on a rigid alumina-based SPE.

In order to confirm that the hydrophobic nature of the neoprene substrate did not change as a result of the screen printing process, contact angle measurements were performed (using seawater) on the bare neoprene substrate as well as on the printed carbon working electrode (not shown). The contact angle for the bare neoprene and for the carbon on neoprene were 138°±5 and 120°±5, respectively, indicating that the carbon coating exhibits slightly better wettability when compared with the bare neoprene substrate. Moreover, the superhydrophobic characteristic of the neoprene is maintained such that a constant electrode area can be maintained.

Electrochemical characterization of the SPE in response to mechanical deformation may be performed as follows. Following the morphology investigation, we characterized the electrochemical behavior of the neoprene SPE using the potassium ferricyanide redox marker. FIGS. 19A, 19B, 19C, and 19D show typical cyclic voltammograms (CV, 50 mV/s scan rate) for 5 mM ferricyanide as well as the blank solution (seawater) at the flexible neoprene SPE (FIG. 19A) and at a common rigid alumina-based SPE (FIG. 19B). These voltammograms indicate that the redox activity and the background response are not compromised by the neoprene substrate. The low background response indicates that the neoprene constituents do not contribute to the baseline. Both substrates yield two characteristic ferricyanide redox peaks, with similar peak potentials and separations. The oxidation peaks are located at 0.32 V and 0.35 V while the reduction peaks appear at 0.00 V and −0.02 V for the neoprene and alumina SPEs, respectively. As can be seen, the reversibility of the redox process is not affected by the neoprene substrate. Even though the geometric areas were identical for both SPE variants, the neoprene SPE displays higher anodic and cathodic peak currents which can be attributed to a slightly larger active area on the neoprene substrate.

Wearable underwater sensors are expected to be deformed during routine use. Accordingly, the influence of mechanical deformation upon the voltammetric response was investigated in further detail. FIGS. 19C and 19D illustrate the effect of repetitive 90° bending operations upon the CV response. Minimal changes in the peak potential and currents are observed as a result of the mechanical deformation. The relative standard deviation (RSD) values were found to be less than 4%, thus it can be concluded that the neoprene SPE is capable of withstanding repeated deformation without significant alteration of the electrochemical output signal. This is supported by consecutive resistance measurements that indicate that the conductivity of the trace did not deteriorate, although microcracks in the electrodes were observed during prolonged bending. More specifically, while the resistance at the reference electrode increased by as much as 10% throughout repeated mechanical deformation, the resistance of the counter and working electrode traces did not deviate by more than the measurement error. As a matter of fact, the trace resistance measured at the neoprene SPE, even following multiple bending operations, did not exceed the characteristic resistance of the traces at the common alumina-based SPE. Thus it can be concluded that the conductivity of the traces was maintained through repeated deformation.

Following the initial electrochemical characterization, the study focused on demonstrating the potential of the wearable sensing electrodes for relevant water-quality applications and using different model pollutants along with untreated seawater samples.

Biosensing of trace phenols may be performed as follows. Phenols represent a pervasive class of organic compounds that are produced on an industrial scale and typically enter aquatic environments from the run-off generated by industrial and agricultural processing. The inherent toxicity of phenolic compounds creates urgent needs for their in-situ monitoring in marine environments. The ability to continuously monitor the levels of such compounds would thus prove extremely valuable as an alert for recreational divers and surfers.

Figures 20A, 20B, 20C, 20D:
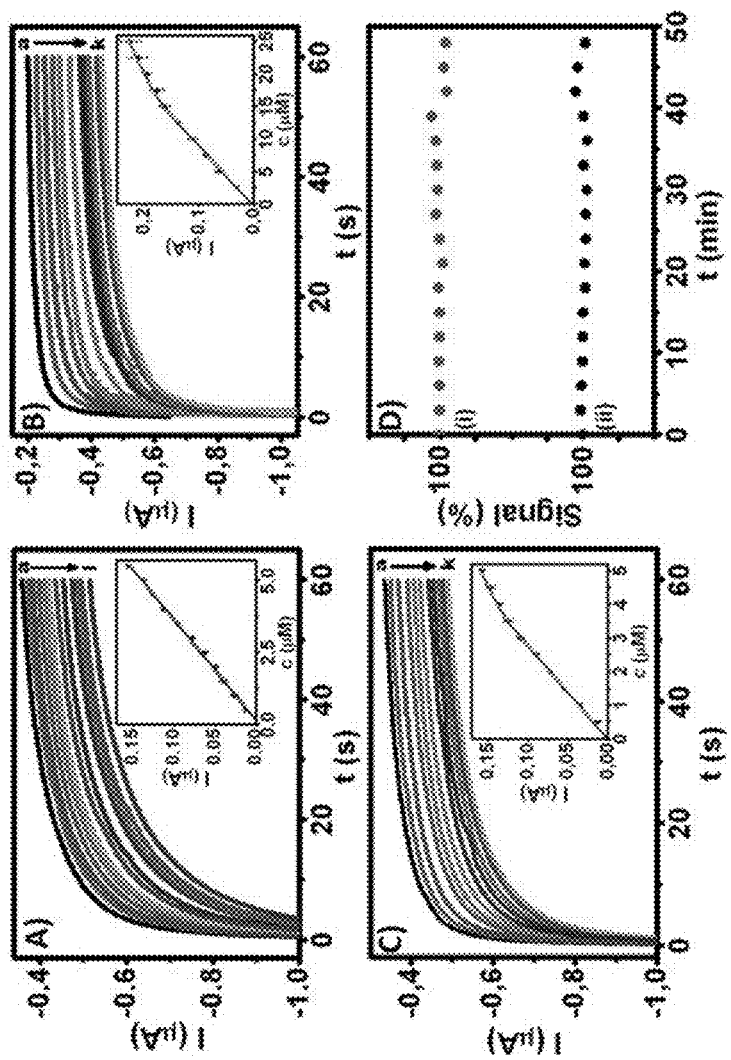
FIGS. 20A, 20B, 20C and 20D show chronoamperograms of the tyrosinase-modified neoprene SPE in the presence of various phenolic compounds (step potential: −0.3 V vs Ag/AgCl). Samples were incubated on the electrode surface for 2 min prior to measurement.

In order to facilitate the trace detection of phenolic contaminants, a tyrosinase-containing carbon ink was employed for printing the amperometric biosensor directly on the wearable neoprene substrate. The electrochemical response to micromolar changes of phenols (phenol, 4-chlorophenol, and catechol) was investigated using the neoprene-Tyr SPE biosensor. Such biosensing route relies on the specificity of the enzyme, that catalyzes the hydroxylation of phenols to allow a low-potential selective detection of the quinone products. In contrast, direct anodic measurements of phenols require high potentials and are vulnerable to potential interferences by co-existing oxidizable species. Chronoamperometric measurements of the quinone product were carried out by applying a reduction potential of $-0.30$ V vs Ag/AgCl. The corresponding chronoamperograms for increasing levels of phenol (0 µM to 5.5 µM in 0.5 µM increments), 4-chlorophenol (0 µM to 25 µM in 2.5 µM increments), and catechol (0 µM to 5 µM in 0.5 µM increments) are shown in FIGS. 20A, 20B, and 20C, respectively. Well defined current signals are observed for these low micromolar concentrations; the limits of detection (LOD, using the $\mu+3\sigma$ methodology) for phenol, 4-chlorophenol, and catechol are 0.25 µM, 0.43 µM, and 0.13 µM, respectively. The corresponding calibration plots are provided in the insets. As expected for biocatalytic reactions, the response for 4-chlorophenol and catechol increases linearly with the concentration at first and exhibits some curvature at elevated levels. A highly linear response is observed for phenol (FIG. 20A). The sensitivity was 28 nA/µM, 10 nA/µM, and 35 nA/µM for phenol, 4-chlorophenol and catechol, respectively (R2-values of 0.996, 0.996, and 0.997). The higher sensitivity towards catechol can be attributed to the single reaction step required for the enzymatic catalysis of catechol compared to the two-step reaction required for phenol and 4-chlorophenol. High stability is another important requirement for underwater marine monitoring. The response of the sensor was examined over a period of 50 minutes by performing 17 repetitive chronoamperograms (at three minute intervals). FIG. 20D examines the stability of the Tyr-SPE signal, relative to the first measurement (t=0 min), for 10 mM 4-chlorophenol (i) and 2 mM phenol (ii). These experiments yielded low RSD for each compound, ranging from 2.07% to 1.73%, respectively. Minor batch-to-batch variations (5-10%) could be readily mitigated via initial calibration in the seawater matrix.

Figures 21A, 21B:
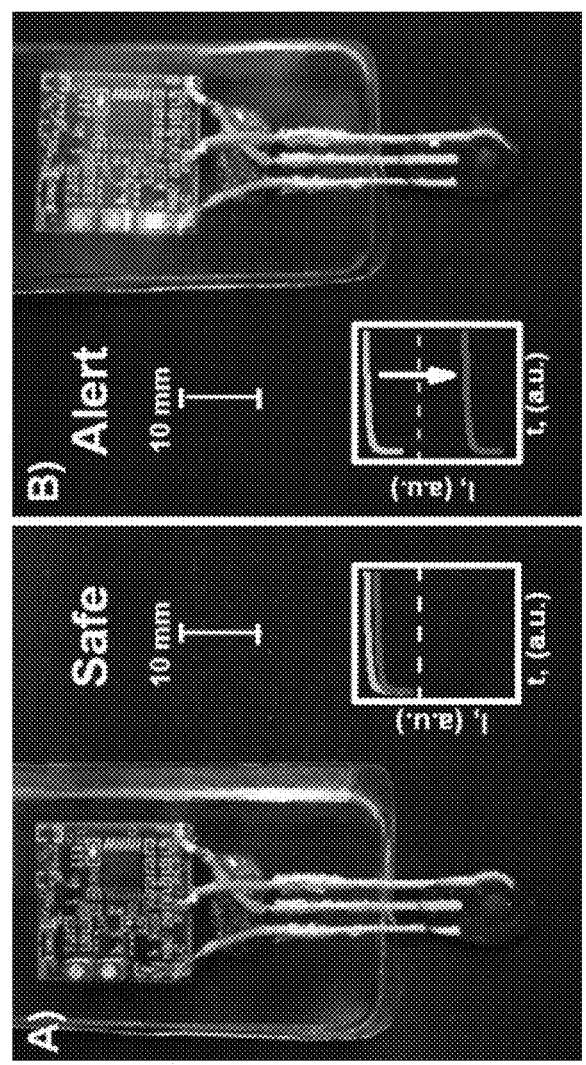
FIGS. 21A and 21B show sealed, battery-operated electrochemical microsensor with integrated potentiostat interfaced with a screen-printed three-electrode setup on the neoprene substrate. Safe environmental conditions are indicated in FIG. 21A, whereas the additional illumination of a red LED in FIG. 21B is indicative of a phenol content in sea water that exceeds a certain level (5.5 µM). Ew=−0.3 V vs Ag/AgCl, EThreshold=0.566 V. Insets show the outputs of the micropotentiostat block, illustrating the increased current magnitude caused by elevated phenol concentrations; a dashed line represents the threshold.

In order to provide a viable alternative to current sensing systems, an SPE sensor was printed on the sleeve of a neoprene wetsuit. The working electrode was modified with Tyr and the whole system was mated with an encapsulated (watertight) miniaturized potentiostat that was able to provide the wearer with a visual cue whether the level of phenolic compounds has exceeded a pre-defined threshold value. An image of the entire sensing system is shown in FIGS. 21A and 21B. In response to elevated levels of phenol (5.5 µM), the potentiostat-integrator-voltage amplifier analog system yielded an output potential of 0.797±0.012 V, while the absence of phenols (0 µM) yielded a potential of 0.335±0.008 V. Accordingly, by means of an adjustable voltage divider, the switching threshold for the comparator was established at 0.566 V, the arithmetic mean of the two extremes, and purely digital 'Safe'/'Hazard' analysis could be obtained. A 'Safe' (unpolluted) seawater environment is indicated by a green light, while in the case of hazardous levels of phenols, a red LED is illuminated (FIG. 21B). The output of the potentiostat block of the sensor (FIG. 21B inset) illustrates the increase in the current magnitude caused by elevated phenol concentrations; a dashed line represents the threshold.

Trace explosive detection may be performed as follows. As a consequence of war, military training, and the dumping of munitions, many marine areas are still polluted by dangerous remains of undetonated ordnance. In minesweeping missions, the detection of these explosive compounds could indicate the presence of naval mines or depth charges. Bearing in mind the abundance of dumped munitions and ordnance in the world.

These experiments were performed by applying rapid square-wave voltammetry. FIG. 22A displays representative voltammograms for untreated seawater sample containing increasing levels of TNT in 100 ppb steps. The well-defined voltammograms illustrate a reduction peak at $-0.54$ V vs Ag/AgCl and a smaller shoulder at $-0.74$ V. The peak at $-0.54$ V is attributed to the reduction of the nitro groups, while the minor bodies of water, there is a need to ascertain the presence of these hazards in aquatic environments. Underwater wearable sensors could monitor the electrochemical response of explosive agents in a continuous fashion and could alert the wearer of a potential threat. Accordingly, the neoprene-based electrochemical sensor was examined for voltammetric detection of the common model nitroaromatic explosive TNT. shoulder at $-0.74$ V is due to the reduction of the hydroxylamine product FIG. 22B displays the corresponding calibration curve that illustrates linearity from 100 to 900 ppb of TNT (peak current at $-0.54$ V vs TNT concentration; R2=0.990). The high sensitivity (S=6.5 nA/ppb) and the low LOD of 42 ppb (estimated from the 100 ppb TNT response) illustrate the highly-sensitive detection capability of the neoprene SPE towards trace explosives in marine environments. No apparent peaks are observed in the corresponding background voltammograms, reflecting the high selectivity of the sensor.

The stability of the wearable explosive sensor was evaluated by performing 30 repetitive measurements of 500 ppb TNT at 2 min intervals. As indicated from the resulting voltammograms of FIG. 22C, this prolonged one-hour experiment yielded a highly stable voltammetric response using seawater. FIG. 22D illustrates the stability of the peak current (at $-0.55$ V) with respect to the initial measurement at t=0 min (100%). The low RSD of 0.59% indicates a highly stable response, without apparent surface fouling.

Heavy metal monitoring may be performed as follows. Copper is an important constituent of antifouling paints utilized for maritime applications. The release of copper from such paints greatly contributes to the contamination of harbors and to marine environments, in general. Hence, a wearable sensor that can be adapted for underwater trace-metal monitoring should be attractive for detecting copper in aquatic environment.

To accomplish this goal, trace copper detection was performed using square-wave stripping voltammetry at the neoprene-based printed carbon sensor that was coated with a gold film. This represents the first example of using a wearable sensor for trace metal stripping-voltammetric measurements. A calibration curve was obtained through successive additions of copper into a cell containing untreated seawater. The copper was deposited on the electrode for 2 min at −1.00 V vs Ag/AgCl and was stripped from the electrode by scanning the potential to 0.50 V. FIG. 23A shows the voltammograms obtained at the Au-modified neoprene SPE for a seawater sample containing increasing concentrations of copper, while FIG. 23B depicts the resulting calibration curve for the integrated peak area vs copper concentration. Both experiments yielded well defined copper peaks, with no overlapping signals. A linear range from 10 to 90 ppb levels of copper is observed (R2=0.988), along with a sensitivity of 406 nC/ppb and an LOD of 13 ppb. The stripping copper response at the Au-modified neoprene SPE is also highly reproducible. FIGS. 23C and 23D display a series of ten successive measurements of 100 ppb copper in untreated seawater over a 50 minute period. A highly reproducible copper peak is observed throughout this operation (RSD=1.76%).

It will be appreciated that technologies for screen printed electrochemical sensors on underwater garments that are able to detect trace levels of marine pollutants and explosive threats in seawater have been disclosed. Wearable electrodes intended for in-situ water analysis should alleviate the cumbersome process of sample preparation and analysis, hence allowing the wearer to monitor its surroundings for contaminants or hazards while performing other tasks. By printing the sensors on synthetic rubber neoprene substrates, commonly used in underwater garments, the real-time voltammetric detection of trace levels of Cu and TNT has been attained. Moreover, the inclusion of an enzyme within the printed ink enabled the biosensing of micromolar levels of phenolic contaminants. The neoprene-based printed electrodes can tolerate severe mechanical deformations that may be encountered during routine underwater activity. Whenever needed, an initial calibration in the seawater sample could be used for addressing potential matrix effects (such as changes in the temperature or oxygen level). The integration of printable sensors on underwater garments such as dry and wetsuits holds considerable promise for numerous marine sensing applications where real-time analysis and sensor miniaturization are core requirements. The concept can be further extended to other important threat assessment and environmental monitoring applications in marine environments.

Figures 24, 25:
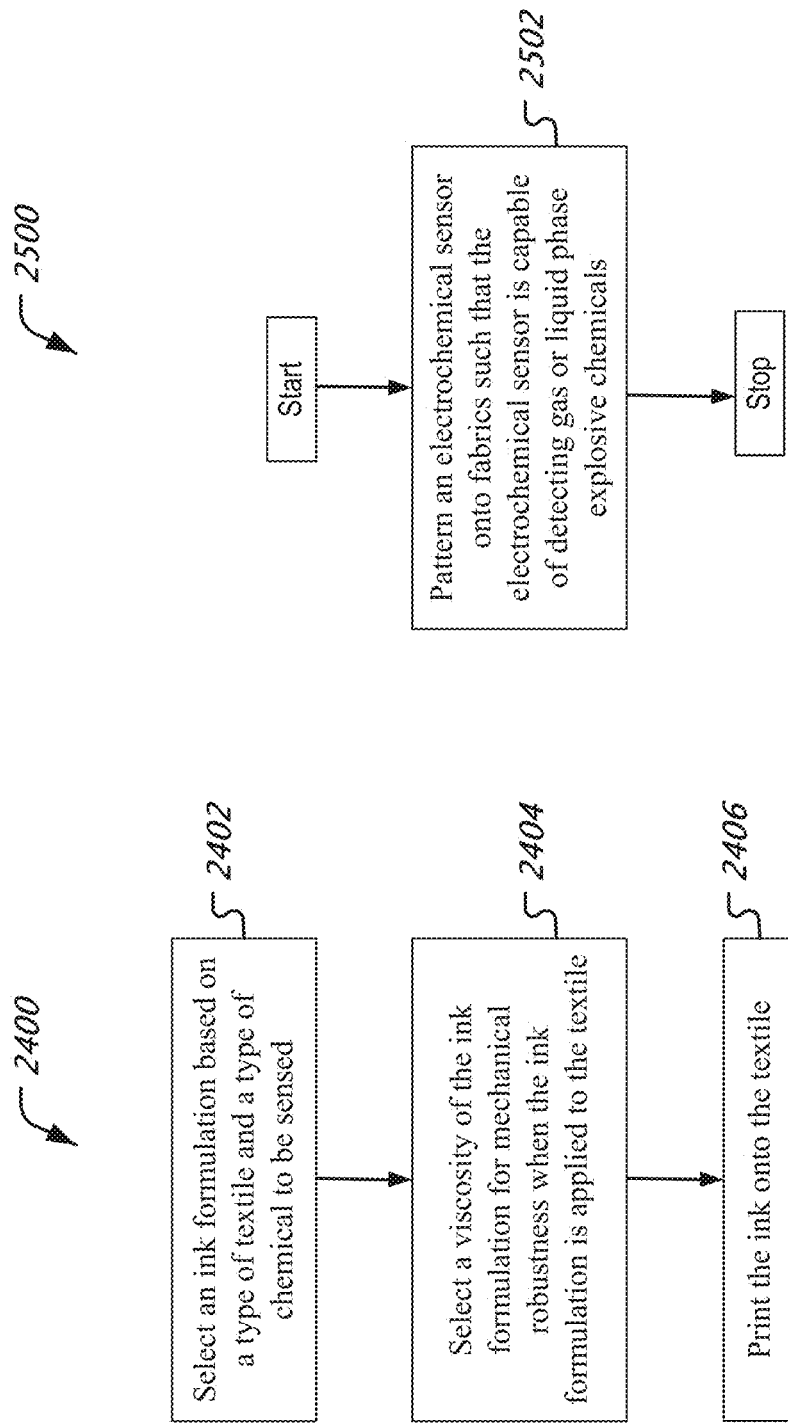
FIG. 24 is a flowchart representation of a process of incorporating a chemical sensor into a textile.
FIG. 25 is a flowchart representation of a process of producing an explosive detection product.

FIG. 24 is a flowchart representation of a process 2400 of incorporating a chemical sensor into a textile. At 2402, an ink formulation is selected based on a type of textile and a type of chemical to be sensed. Several selection techniques have been discussed previously in this document. At 2404, a viscosity of the ink formulation is selected to achieve mechanical robustness when the ink formulation is applied to the textile. The desired mechanical robustness may depend upon the desired application, e.g., rubbing against the body, folding during use and storage and whether used for underwater wearing, and so on. At 2406, the ink is printed onto the textile.

FIG. 25 is a flowchart representation of a process 2500 of producing an explosive detection product. At 2502, an electrochemical sensor is patterned onto fabrics such that the electrochemical sensor is capable of detecting gas or liquid phased explosive chemicals. In some embodiments the electrochemical sensor is characterized to provide a robust and reliable detection of an explosive nitro or nitrate compound. In some embodiments, the nitro or nitrate compound may be one of Hexamethylene triperoxide diamine (HMTD), triacetone triperoxide (TATP), tetryl, nitroglycerin, hexhydro-1,3,5-trinitro-1,3,5-s-trazine (RDX), 1,3,5,7-tetranitro-1,3,5,7-tetraazacyclo-octane (HMX), and 2,4,6,8,10,12-hexanitrohexaazaisowurtzitane (HNIW). As previously described, the fabrics may be one of cotton, polyester, neoprene or GORE-TEX.

Figure 26:
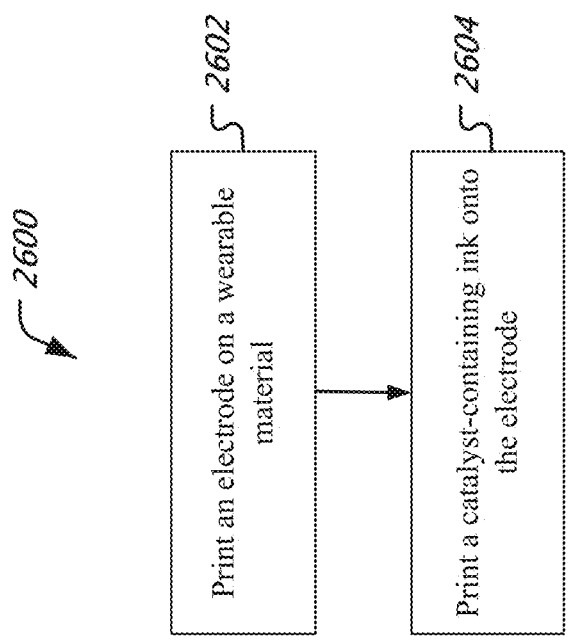
FIG. 26 is a flowchart representation of a process of fabricating a product for underwater sensing of chemicals.

FIG. 26 is a flowchart representation of a process 2600 of fabricating a product for underwater sensing of chemicals. At 2602, an electrode is printed on a wearable material. The wearable material may include, e.g., neoprene, as previously described. At 2604, an enzyme-containing ink is printed onto the electrode. In some embodiments, at least one of relevant reagents, substrates, co-substrates, co-factors, and immobilizers onto the electrode. It may be appreciated that such co-existing chemical species may help sustain the catalytic or biocatalytic reaction. In some embodiments, a conductive layer is directly printed on the wearable material and the conductive layer is overlayed with a carbon-based material to define geometry of the electrode. The electrode may further be cured prior to the operation. In some embodiments, during fabrication, the electrode may be allowed to dry for a certain duration after the printing of the enzyme-containing ink is performed.

It may be appreciated that the present document discloses a chemical sensor incorporated into textile or clothing. In some embodiments, the chemical sensor comprises one of an amperometric sensor and a potentiometric sensor. The chemical sensor may include at least one carbon based electrode to detect at least one of physiologically-relevant analyte and nitro- or nitrate-based explosive, in liquid or vapor phase. In some embodiments, the at least one carbon based electrode is for detecting at least one of nicotinamide adenine dinucleotide, NADH, hydrogen peroxide, potassium ferrocyanide, trinitrotoluene, TNT, and dinitrotoluene, DNT, in liquid or vapor phase. In some embodiments, the chemical sensor may further include a chemically selective layer such as a permselective coating or a catalytic layer. In some embodiments, the catalytic layer may include a biocatalyst. The biocatalyst may include an enzyme such as dehydrogenase- and oxidase-based enzymes for at least one of urea, glucose, ethanol and lactate sensing. In some embodiments, the catalytic layer comprises a metallic catalyst selected from the group nickel, bismuth, silver, gold, platinum, palladium, iridium, rhodium, osmium, and ruthenium for hydrogen peroxide and NADH sensing.

It will further be appreciated that a chemical sensor incorporated into specific clothing elements is disclosed. The specific clothing elements may include at least one of an undergarment waistband, a bra strap, a cuff, a sock, a wristband, an armband, a headband and a collar for optimal on-body contact.

It will further be appreciated that a wearable garment product is disclosed. The garment product includes a substrate comprising a wearable material, an electrode printed on the substrate and a catalyst-containing ink printed onto the electrode While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. An item of textile or clothing, comprising a chemical sensor incorporated into textile or clothing, the chemical sensor comprising at least one of an amperometric sensor or a potentiometric sensor; the chemical sensor being positioned on a portion of the item of textile or clothing that comes in direct body contact;
   at least one carbon based electrode to detect at least one of physiologically-relevant analyte and nitro- or nitrate-based explosive, in liquid or vapor phase; and
   flexible electronic equipment, integrated on a surface of the textile or clothing, to communicate results of sensing by the chemical sensor.

2. The chemical sensor of claim 1, wherein the at least one carbon based electrode is for detecting at least one of nicotinamide adenine dinucleotide, NADH, hydrogen peroxide, potassium ferrocyanide, trinitrotoluene, TNT, and dinitrotoluene, DNT, in liquid or vapor phase.

3. An item of textile or clothing comprising a chemical sensor incorporated into textile or clothing, the chemical sensor comprising at least one of an amperometric sensor and a potentiometric sensor; the sensor further comprising a chemically selective layer; wherein the chemically selective layer comprises a permselective coating or a catalytic layer; and wherein the chemical sensor is positioned on a portion of the item of textile or clothing that comes in direct body contact; and wherein the item of textile or clothing comprises flexible electronic equipment, integrated on a surface of the textile or clothing, to communicate results of sensing by the chemical sensor.

4. The chemical sensor of claim 3, wherein, when the chemically selective layer comprises the catalytic layer, the catalytic layer comprises a biocatalyst.

5. The chemical sensor of claim 4, wherein the biocatalyst comprises an enzyme.

6. The chemical sensor of claim 5, wherein the enzyme comprises dehydrogenase- and oxidase-based enzymes for at least one of urea, glucose, ethanol and lactate sensing.

7. The chemical sensor of claim 3, wherein, when the chemically selective layer comprises the catalytic layer, the catalytic layer comprises a metallic catalyst selected from the group nickel, bismuth, silver, gold, platinum, palladium, iridium, rhodium, osmium, and ruthenium for hydrogen peroxide and NADH sensing.

8. A textile-integrated chemical sensor system, comprising:
   a wearable textile material;
   a chemical sensor incorporated onto the textile material; and
   flexible electronic equipment, integrated on a surface of the wearable textile material, for displaying and communicating results of sensing by the chemical sensor;
   wherein at least one of the chemical sensors, support electronics, a display, power and communication functions are implemented in a custom integrated circuit chip.

9. A method of performing at least one of the following operations using a textile-integrated chemical sensor system, the operations including sweat monitoring for alcohol levels, monitoring of performance/stress/exertion levels, monitoring of incontinence products, wearable heart-rate, or blood-pressure, or monitoring of toxic gases or chemical agents,
   wherein the textile-integrated chemical sensor system comprises:
   a wearable textile material;
   a chemical sensor incorporated onto the textile material; and
   flexible electronic equipment, integrated on a surface of the wearable textile material, for displaying and communicating results of sensing by the chemical sensor;
   wherein at least one of the chemical sensors, support electronics, a display, power and communication functions are implemented in a custom integrated circuit chip.

* * * * *